(12) United States Patent
Corcoran et al.

(10) Patent No.: US 7,078,217 B2
(45) Date of Patent: Jul. 18, 2006

(54) AGGRECANASE MOLECULES

(75) Inventors: Christopher J. Corcoran, Arlington, MA (US); Michael J. Agostino, Andover, MA (US); Edward R. LaVallie, Harvard, MA (US); Carl R. Flannery, Acton, MA (US); Lisa A. Collins-Racie, Acton, MA (US)

(73) Assignee: Wyeth, Madison, NJ (US)

( * ) Notice: Subject to any disclaimer, the term of this patent is extended or adjusted under 35 U.S.C. 154(b) by 268 days.

(21) Appl. No.: 10/354,983

(22) Filed: Jan. 31, 2003

(65) Prior Publication Data

US 2004/0044194 A1  Mar. 4, 2004

Related U.S. Application Data

(60) Provisional application No. 60/353,680, filed on Jan. 31, 2002.

(51) Int. Cl.
*C12N 9/64* (2006.01)
*C12N 1/21* (2006.01)
*C07H 21/04* (2006.01)

(52) U.S. Cl. .................. 435/226; 435/252.3; 536/23.2
(58) Field of Classification Search ................ 435/226, 435/252.3; 536/23.2
See application file for complete search history.

(56) References Cited

U.S. PATENT DOCUMENTS

| 4,419,446 | A |  | 12/1983 | Howley et al. |  |
| 4,816,567 | A |  | 3/1989 | Cabilly et al. |  |
| 2003/0185828 | A1 | * | 10/2003 | Yamaji et al. | 424/146.1 |
| 2004/0018555 | A1 | * | 1/2004 | Anderson et al. | 435/7.1 |
| 2004/0053269 | A1 | * | 3/2004 | Todd et al. | 435/6 |

FOREIGN PATENT DOCUMENTS

| EP | 0 123 289 A2 | 10/1984 |
| EP | 0 155 476 A1 | 9/1985 |
| EP | 0 177 343 A1 | 9/1986 |
| WO | WO 86/00639 A1 | 1/1986 |
| WO | WO 01/83782 A2 | 11/2001 |
| WO | WO 02/50258 A1 | 6/2002 |

OTHER PUBLICATIONS

Strausberg et al. (Dec. 24, 2002) PNAS, vol. 99, pp. 16899-16903.*
GenBank accession AAH63283 (Dec. 3, 2003).*
GenBank accession BC063283 (Dec. 3, 2003).*
Abbaszade et al., "Cloning . . . ," JBC, vol. 274 (No. 33), p. 23443-23450, (Aug. 13, 1999).
Altschul et al., "Basic . . . ," J. Mol. Biol., vol. 215, p. 403-410, ( Oct. 5, 1990).
Ausubel et al., "Current Protocols in Molecular Biology," vol. I, John Wiley & Sons, Inc., N.Y., p. 6.3.1-6.3-6 , (1989).
Brandt and Mankin, "Pathogenesis . . . , " Textbook of Rheumatology, p. 1355-1373, (1993).
Clackson et al., "Making . . . ," Nature, vol. 352, p. 624-628, (Aug. 15, 1991).
Flannery et al., "Identification . . . ," JBC, vol. 267 (No. 2), p. 1008-1014, (Jan. 15, 1992).
Fosang et al., "Neutrofil . . . , " Biochem. J., vol. 304, p. 347-351, (Dec. 1, 1994).
Gething and Sambrook, "Cell-surface . . . ," Nature, vol. 293, p. 620-625, (Oct. 22, 1981).
Gossen and Bujard, "Tight . . . ," PNAS USA, vol. 89, p. 5547-5551, (Jun. 15, 1992).
Gough et al., "Structure . . .," EMBO J., vol. 4 (No. 3), p. 645-653, (Mar., 1985).
Hughes et al., "Monoclonal . . . ," Biochem. J., vol. 305, p. 799-804, (Feb. 1, 1995).

(Continued)

*Primary Examiner*—Elizabeth Slobodyansky
(74) *Attorney, Agent, or Firm*—Kirkpatrick & Lockhart Nicholson Graham LLP

(57) ABSTRACT

Novel aggrecanase proteins and the nucleotide sequences encoding them as well as processes for producing them are disclosed. Methods of identifying and developing inhibitors of the aggrecanase enzymes and antibodies to the enzymes for treatment of conditions characterized by the degradation of aggrecan are also disclosed.

4 Claims, 14 Drawing Sheets

OTHER PUBLICATIONS

Jang et al., "Initiation . . . , "J. of Virol., vol. 63 (No. 4), p. 1651-1660, (Apr. 1989).
Kaufman and Sharp, "Amplification . . . ," J. Mol. Biol., vol. 159, p. 601-621, (Aug. 25, 1982).
Kaufman et al., "Coamplification . . . ," Mol. and Cellular Bio., vol. 5 (No. 7), p. 1750-1759, (Jul., 1985).
Kaufman and Sharp, "Construction . . . ," Mol. and Cellular Bio., vol. 2 (No. 11), p. 1304-1319, (Nov., 1982).
Kaufman, "Identification . . . ," PNAS USA, vol. 82, p. 689-693, (Feb., 1985).
Kaufman et al., "Improved . . . ," Nuc. Acids Res., vol. 19 (No. 16), p. 4485-4490, ( Aug. 25, 1991).
Kohler and Milstein, "Continuous . . . ," Nature, vol. 256, p. 495-497, (Aug. 7, 1975).
Laemmli, "Cleavage . . . , " Nature, vol. 227, p. 680-685, (Aug. 15, 1970).
Littlefield, "Selection . . . ," Science, p. 709, (Aug. 14, 1964).
Lohmander et al., "The Structure . . . ," Arthritis & Rheumatism, vol. 36 (No. 9), p. 1214-1222, (Sep., 1993).
MacLean et al., "Costs . . . ," J. of Rheumatology, vol. 25 (No. 11), p. 2213-2218, (Nov., 1998).
Maniatis et al., Molecular Cloning: A Laboratory Manual, p. 387-389, (1982).
Marks et al., "By-passing . . . ," J. Mol. Biol., vol. 222, p. 581-597, (Dec. 5, 1991).
Mercuri et al., "Recombinant . . . ," JBC, vol. 274 (No. 45), p. 32387-32395, (Nov. 5, 1999).
Miller et al., "An Insect . . . ," Genetic Engineering, vol. 8, p. 277-298, (1986).
Morinaga et al., "Improvement . . . ," Bio/Technology, p. 636-639, (Jul., 1984).
Myers and Miller, "Optimal . . . ," CABIOS, vol. 4 (No. 1),p. 11-17, (Mar., 1988).
Needleman and Wunsch, "A General . . . ," J. Mol. Biol., vol. 48, p. 443-453, (Mar., 1970).v.
Oakley et al., "A Simplified . . . ," Analytical Biochemistry, vol. 105, p. 361-363, (Jul. 1, 1980).
Oi and Herzenberg, Selected Methods in Cellular Immunology, W. J. Freeman Co., San Francisco, CA, p. 351-372 (1980).
Okayama and Berg, "High-Efficiency . . . ," Mol. and Cellular Bio., vol. 2 (No. 2), p. 161-170, (Feb. 1982).
Sandy et al., "Catabolism . . . ," The J. of Bio. Chem., vol. 266 (No. 14), p. 8683-8685, (May 15,1991).
Sandy et al., "The Structure . . . ," J. Clin. Invest., vol. 89, p. 1512-1516, (May, 1992).
Taniguchi et al., "Expression . . . ," PNAS USA, vol. 77 (No. 9), p. 5230-33, (Sep., 1980).
Tortorella et al., "Purification . . .," Science, vol. 284, p. 1664-1666, (Jun. 4, 1999).
Towbin et al., "Electrophoretic . . .," PNAS USA, vol. 76 (No. 9), p. 4350-4354, (Sep., 1979).
Urlaub and Chasin, "Isolation . . . ," PNAS USA, vol. 77 (No. 7), p. 4216-4220, (Jul., 1980).
Wong et al., "Human . . .," Science, vol. 228 (No. 4701), p. 810-815, (May 17, 1985).

* cited by examiner

Full-length EST18 nucleotide sequence: SEQ ID NO: 1

```
ATGGAGTGCGCCCTCCTGCTCCGTGTGCCTCCCGCGGTTCGGCCCGCTGCGCCTGGCGGACTGGGGCG
CGTGGCCAAGGCGCTCCAGTCGATTGATTACGTCTTTGTCACGCGGTCGTGCTGCCTGCGCCTTAGCGACGCAGCAGCGCG
CCAGCGGATTAAATGATGATTACGTCTTTGTCACGCCAGTAGAGCTCAGCGGGTCATATATTTCACACGACATT
TTGCACAACGGCAGGAAAAAGCGATCGGCGCAGAATGCCAGAAGCTCCCTGCACTACCGATTTCAGCATTTGGACAGGA
ACTGCACTTAGAGAACTTAAGCCCCTCGGCGATTTTGAGCAGTCACTTGTCCAGTACTTGGAAAGATGGTGCTTCAG
AGACTCAGAGAACCCGAGGTGCAGCAATGCTTCTATCAGGGATTATCAGAAAATGAATCCTCATCTCGCCATTACCTCAGCTTCTGGCCCA
ACGTGTGCTGGCTTGTCAGTTTAATAAGGACACGAAAAAATGAATTCCCACGTACTGTACAAAAGGACAGCAGATCCAGTCGAGAG
GGAACACAACCACAGCTCCCCTGCGGGTCACCATCCGCGGAATTATCCTGGTTACTCCCCAAGTCACATTCTCCCAAGCCTCATA
ACCGTGGCTACCCCGGCTCTGCCAAGTTGCAAAAGCAGCATTTTTGTGGGCGACGCAAGAGATCAGCTGGAAATGTCACCACATACATTCTCACA
ACAGAGTATCACCATCTAAGGTTTGATGAATATGGGAGACTATTGGAAGTGACATAAACGTGGTTGTGTTTTTGTCAGTTCTG
ATGTGGAAACCCTCGTGCTGTGCAGAGAATTATTAAAGATGGAAGACCAGTCTCTGAATTTGATATTGTTCTTGAAGAATGAA
TCTGAACAAGAACCTGAGAGAATGGCAAGAGACATGATCATGCACCATCTTAACAAGTACCGAAGTGTACCATCAATGAGGACACAGG
CCCTCATTGGACACTCTAGGGTTTGCCCCCATCGCTCAAGGGCACAACTTTGGTATGATGAAGCAACCTGCA
CCATGTGACACTCTAGGGTTTGCCCTTCACCATCGCTCATGAGTGTCCCACACACTCAGTGAGTCAGGAATGGTATGATGGAGTGTTTTCATGGAGTGTCTTCTTGCAGCCGCCAG
ACTTGGCCCTTGCCTTCACCATCGCTCATGAGTCCCACACTCAGTGAGTCAGGAAACAATGGAGTGTTTTCATGGAGTGTCTTCTTGCAGCCGCCAG
GAAAGGCTGAAGCAATATCATGTCCCAGCACACCTCAGCGCGGGTGTCTAGTAGTGGATGAGCCAAGCAAAAGCCAAGTTATGCAGCC
TATCTCAAGAGAAATTCCTCAGCACAGATTATGATGCTGACACACAGTGTAAATGGCAATTTGGAGCAAAAGCCAAGTTATGCAGCC
GGACAAAACTACCAGAGACAGATATTTGCAAATCACTTTGGTGCACCAGTAGGCCGTGAGACCAAGTTTATGCCCCGCA
TTGGTTTTGTGAAGGACCGTTTGTGGCTTGGCTTGAGTATGTGGTGCAAGGCCAGTGCCGTAAAGTTTGGGAGCTCGGCCCCGGCC
GCAGAAGGACACCGGCCAGTGCGTCCCGCCTCGGTCCGGGCAAGTGTTCCGGACATGTGGTGGAGGAGTCAAGTTCCAGGAGA
CATCCACACGGCAATAACCCCAAGCCTCAGTTGGTGCCGTTCTAGCCTTTATCAGCCCTATTTATCAGCTGTGCAATATT
GACACTGTCAATAACCCCAAGCCTCAGTTGGTGCCGTTCTAGCCTTTATCAGCCCTATTTATCAGCTGTGCAATATT
```

FIG. 1A

```
AACCCTTGCAATGAAAATAGCTTGGATTTTCGGGCCCAACAGTGTGCAGAGAATATAACAGCAAACCTTTCCGTGGATGTGT
CTACCAGTGGAAACCCTATACAAAGTGGAAGAGGAAGATGATGCAAACTGTACTGCAAGGCTGAGAACTTTGAATTTT
TTTTGCAATGTCCGGCAAGTGAAAGATGAACTCCCTGCTCCCAAACAGATAATGATGTTTGTATTGACGGGTTTGT
GAACTAGTGGGATGTGATCATGAACTAGGCCTCTAAAGCAGTTTCAGATGCTTGTGGCGTTTGCAAAGGTGATAATTCAAC
TTGCAAGTTTTATAAAGGCCTGATCAAACCAGCATAAAGCAAATGAATATTATCCGGTGGTCATTCAAAAGTATTACCTC
CCCGAAGCATCGAAATCCAAGAGCTGCAGTGTTCCTCCAGTTACCCTCGAAGCCTCAGTACCACGCGCTCTTTCAACCG
ACCGGGGCTGGAGCATCGACTGGCCTGGGGCAGTTCCCCTTGGGAGTTCCCCCTCGCTGGTCTTTGAATATGACCTCTACCAAGGCAAAAATCCAGGA
CCCGGAACGTCTGTACGCGCCAGGGCCCAAAATGAAATGAATGAGACGCTGGTCTTTGAAATTCTGATGCAAGGCTATACCTGGAGTATC
TAGCTTGGAAGTATGCACTTCCCAAGGTCACTCCCTGTCTCCTGTGGTGAGGTTACATAAATGTAAAGGCCATTTGCTTGCGAGATCAAAATACTCA
GTGCAGTCAGAGTGCTCTCCGTCGTCTGCAGTGCAAAACCAAGCCAGTAGCAAGGCCAGCAAGATCTCAGGTCCAAGCTGTGTGCAA
AGTCAATTCCTCATTCTGCCAGTGAATGGAGTACATGTAGAGCAGTGTTGCATTCTCTCTGTCTCGAGAGACAGAGACACACACTGGTGGATCCGAGCGAGTGGCAA
ACTGGATGCCAGTGAATGGAGTACATGTAGACAGCCAGGCCAGGCAAGATCTCAGGTCCAAGCTGTGTGCAA
AAGAAGCCCTTCCAAAGGAGGAGCAGTGTTGCATTCTCTCTGTCTCGAGAGACAGAGACACCACACTGGTGAGCGAGTGGACCCTGAGCTGCAG
CAGCCATGCCCTGTGCCTGCAAGGGCTCTGCCAATGGAGCCTTTGGGACAAACGCTGGACTGCCCCAAGAACAACAGCCGGCTACACAGTGGTCGCTTCTTCGTGGAGCGAGTTCTGCAAC
GAGGGCTGTGTGGGTTTGGGTGTGCTTGGACAGATGCCCCAAGAACAACAGCCGGCTACACAGTGGTCGCTTCTTCGTGGAGCGAGTTCTGCAAC
CTGTGGTTTGGGTGTGCTAATATTAAGAAACCAAATCTGGACTTGCCGTGGCAGCAGTGCACAGTCCACCTCACCTGTGGGGAGTCCAGACCCGGTC
GAAGATGCCGTAATATTAAGAAACCAAATCTGGACTTGCCGTGGCAGCAGTGCACAGTCCACCTCACCTGTGGGGAGTCCAGACCCGGTC
TACAACATGGTAGCTGGATGGTATTCATTGCCGTGGCAGCAGTGCACAGTCCACCTCACCTGTGGGGAGTCCAGACCCGGTC
AGTCCACTGTGTTCAGCAGGCCTCCTCAAGTTGTCTGCTCCATCAGAGGATCCATCCGTAGATTTCTTCAACTGGTGTCACCTAGTTCCTCAG
CAAACTTCTGCAACCACAAGTTTTACGGAAAAAACAATGCTCAAGTCATGCACAAGGAAGATC
CATGGTGTCTCTGCAACCACAAGTTTTACGGAAAAAACAATGCTCAAGTCATGCACAAGGAAGATC
```

*FIG. 1B*

Full-length EST18 protein sequence: SEQ ID NO: 2

MECALLLACAFPAAGSGPPRGLAGLGRVAKALQLCCLCCASVAAALASDSSSGASGLNDDYVFVTPVEVDSAGSYISHDI
LHNGRKKRSAQNARSSLHYRFSAFGQELHLELKPSAILSSHFIVQVLGKDGASETQKPEVQQCFYQGFIRNDSSSSVAVS
TCAGLSGLIRTRKNEFLISPLPQLLAQEHNHSSPAGHHPHVLYKRTAEEKIQRYRGYPGSGRNYPGYSPSHIPHASQSRE
TEYHHRRLQKQHFCGRRKKYAPKPPTEDTYLRFDEYGSSGRPRRSAGKSQKGLNVETLVVADKKMVEKHGKGNVTTYILT
VMNMVSGLFKDGTIGSDINVVVSLILLEQEPGGLLINHHADQSLNSFCQWQSALIGKNGKRHDHAILLTGFDICSWKNE
PCDTLGFAPISGMCSKYRSCTINEDTGLGLAFTIAHESGHNFGMIHDGEGNPCRKAEGNIMSPTLTGNNGVFSWSSCSRQ
YLKKFLSTPQAGCLVDEPKQAGQYKYPDKLPGQIYDADTQCKWQFGAKAKLCSLGFVKDICKSLWCHRVGHRCETKFMPA
AEGTVCGLSMWCRQGQCVKFGELGPRPIHGQWSAWSKWSECSRTCGGGVKFQERHCNNPKPQYGGIFCPGSSRIYQLCNI
NPCNENSLDFRAQQCAEYNSKPFRGWFYQWKPYTKVEEEDRCKLYCKAENFEFFAMSGKVKDGTPCSPNRNDVCIDGVC
ELVGCDHELGSKAVSDACGVCKGDNSTCKFYKGLYLNQHKANEYYPVVIPAGARSIEIQELQVSSSYLAVRSLSQKYYL
TGGWSIDWPGEFPFAGTTFEYQRSFNRPERLYAPGPTNETLVFEILMQGKNPGIAWKYALPKVMNGTPPATKRPAYTWSI
VQSECSVSCGGGYINVKAICLRDQNTQVNSSFCSAKTKPVTEPKICNAFSCGRGVRKRELLCKGSAAETLPESQCTSLPRPELQ
KKPFQKEEAVLHSLCPVSTPTQVQACNSHACPPQWSLGPWSQCSRTCGRGVRKREMKCSEKGFQGKLITFPERRCRNIKKPNLDLEETCNRRACPAHPV
EGCVLGRCPKNSRLQWVASSWSECSATCGLGVRKREMKCSEKGFQGKLITFPERRCRNIKKPNLDLEETCNRRACPAHPV
YNMVAGWYSLPWQQCTVTCGGGVQTRSVHCVQQGRPSSSCLLHQKPPVLRACNTNFCPAPEKREDPSCVDFFNWCHLVPQ
HGVCNHKFYGKQCCKSCTRKI

```
ACGGGGTTTGTGAACTAGTGGGATGTGATCATGAACTAGGCTCTAAAGCAGTTTCAGATGCTTGTGGCGTTTGCAAAGGT
GATAATTCAACTTGCAAGTTTTATAAAGGCCTGTACCTCAACCAGCATAAAGCATAAATGAATATTATCCGGTGGTCATCAT
TCCAGCTGGCGCCCGAAGCATCGAAATCGAAATCCAGGAGCTGCAGTTTCCTCCAGTTACCTCGCAGTTCGAAGCCTCAGTCAAA
AGTATTACCTCACCGGCCCGGAACGTCTGTACGCGCCAGGGCCCACAAATGAGACGCTGGTCTTTGAAATTCTGATGCAAGCAA
TCTTTCAACCGGGATAGCTTGGAAGTATGCACTTCCCAAGGTCATGAATGGAACTCCACCAGCACAAAAGACCTGCCTATA
AATCCAGGAGTATCGTGCAGTCAGAGTGCTCGTCCGTTCTGCAATGGAGTTACATAAATGTAAAGGCCATTTGCTTGCGAGAT
CCTGGAGTATCGTGCAGTCAGAGTGCTCGTCCGTTCTGCAAAAACCAGTAACTGAGCCCAAATCTGCAACGCTTTCTC
CAAAATACTCAAGTCAATTCCTCATTCTGCCAGTGAATGCAGTACATGTAGTAGCAAGGCCTGCTGTGCTGGAGGCCAGAAAGATCC
CTGCCCGGCTTACTGGATGCCAGTGAATGCAGTACATGTAGTAGCAAGGCCTGCTGTGCTGGAGGCCAGAGCCGAAAGATCC
AGTGTGTGCAAAAGAAGCCCTTGCCTGTCCTCCACAAGGCCATGCAGTGTTGCATTCTGTCCTGGTCTCAGTGTTCCAAGACCTGTGGACGAGG
CAAGCCTGCAACAGCCATGCAACTCCCCTCGCAGAAACCCTGCCGCAAAGAACAGCCCGGCTACAGCCAGTGACCTCCCCAGAC
GGTGAGGAAGCGTGAACTCCTCTGCAGGCCTGTGTGCTTGGACGATGCCCCAAGAACAGCCCGGCTACAGCCAGTGGTCGCTTCTTCGTGGAGCGAG
CTGAGCTGCAGGAGGGCGTGTGTTGGGTGTGTGAGGAGGAGATGAAGTGCAGCAGCGAGAAGTGCAGCAGCGAGAAGGGCTTCCAGGGAAGCTGATAAC
TGTTCTGCAACCTGTGCAACCTGTGGGTGTGTGGGTGTTGGGTTTGGGTGTGTGAGGAGGAGATGAAGTGCAGCAGCGAGAAGGGCTTCCAGGGAAGCTGATAAC
TTTCCCAGAGCGAAGATGC
```

FIG. 3B

MSPFLLQALQLCCLCCASVAAALASDSSSGASGLNDDYVFVTPVEVDSAGSYISHDILHNGRKKRSAQNARSSLHYRFSA
FGQELHLELKPSAILSSHFIVQVLGKDGASETQKPEVQQCFYQGFIRNDSSSVAVSTCAGLSGLIRTRKNEFLISPLPQ
LLAQEHNHSSPAGHHPHVLYKRTAEEKIQRYRGYPGSGRNYPGYSPSHIPHASQSRETEYHHRRLQKQHFCGRKKYAPK
PPTEDTYLRFDEYGSSGRPRRSAGKSQKGLNVETLVVADKKMVEKHGKGNVTTYILTVMNMVSGLFKDGTIGSDINVVV
SLILEQEPGGLLINHHADQSLNSFCQWQSALIGKNGKRHDHAILLTGFDICSWKNEPCDTLGFAPISGMCSKYRSCTIN
EDTGLGLAFTIAHESGHNFGMIHDGEGNPCRKAEGNIMSPTLTGNNGVFSWSSCSRQYLKKFLSTPQAGCLVDEPKQAGQ
YKYPDKLPGQIYDADTQCKWQFGAKAKLCSLGFVKDICKSLWCHRVGHRCETKFMPAAEGTVCGLSMWCRQGQCVKFGL
GPRPIHGQWSAWSKWSECSRTCGGGVKFQERHCNNPKPQYGGIFCPGSSRIYQLCNINPCNENSLDFRAQQCAEYNSKPF
RGWFYQWKPYTKVEEEDRCKLYCKAENFEFFAMSGKVKDGTPCSPNRNDVCIDGVCELVGCDHELGSKAVSDACGVCG
DNSTCKFYKGLYLNQHKANEYYPVVIPAGARSIEIQELQVSSSYLAVRSLSQKYYLTGGWSIDWPGEFPFAGTTFEYQR
SFNRPERLYAPGPTNETLVFEILMQGKNPGIAWKYALPKVMNGTPPATKRPAYTWSIVQSECSVSCGGGYINVKAICLRD
QNTQVNSSFCSAKTKPVTEPKICNAFSCPAYWMPGEWSTCSKACAGGQQSRKIQCVQKKPFQKEEAVLHSLCPVSTPTQV
QACNSHACPPQWSLGPWSQCSKTCGRGVRKRELLCKGSAAETLPESQCTSLPRPELQEGCVLGRCPKNSRLQWVASSWSE
CSATCGLGVRKREMKCSEKGFQGKLITFPERRC

```
CCTGGTCGAAGTGGTCAGAATGTTCCCGGACATGTGTGGTGGAGGAGTCAAGTTCCAGGAGAGACACTGCAATAACCCCAAT
AACAATCAACCAGAGTTTACTGTTTGCATATAAAGTCCATGTGCACCGAGGAAGTGATGGTGGGCAGAAACCAAAACA
CAGCAGAGGAGTCATTCTCTACGGGACTGTGATCCAGCCTCAGTATGGTGGCTTATTCTGTCCAGTTCTGTAGCCGTA
TTTATCAGCTGTGTGCAATAACCCTTGCAATGAAAATAGCTTGGATTTTCGGGCTCAACAGTGTGCAGAATATAACAGC
AAACCTTTCCGTGATGGTTCTACCAGTGAAGTGGAAGATGGAAGAGGAGATCGATGCAAACTGTACTGCAA
GGCTGAGAACTTTGAATTTTTTTGCAATGTCCGGCAAAGTGAACTGAACTAGGCTCTAAGCAGTTTCAGATGCTTGTGCGTT
TTTGTATTGACGGGTTTGTGAACTAGTGTGATCATGAACTAGGCTCTAAGCAGTTTCAGATGCTTGTGCGTT
TGCAAAGGTGATAATTCAAGTTTATAAAGGCCTGTACCCTCAACCAGCATAAAGCAATGAATATTATCCGGT
GGTCCTCATTCCAGCTGGCGCCCGAAGCATCGAAATCCAGGAGCTGCAGGTTTCCTCCAGTTACCTCGCAGTTCGAAGCC
TCAGTCAAAAGTATTACCTCAACCGGCCGGAACGTCTTGCTACATTTATATCGATATCCCCTGGGAGTTCCCCGAGCATG
TACCAGCGCTCTCTTTCAACCGCCCGGAACGTCTTGCTACATTTATATCGATATCCCCTGGGTAAGGTCAGCAAAGG
TTCTCTCACTAGAGGAATGGATTAAATCTGAGACAACCCTTGCTGAGGCCAGTAAGCAACCATCTGTGCAAAAGAAGCC
CCAGGTGAATGGAGTACATGCAGTGTTGCATTCTGCCTTGGACCCCTGGTCTCAGTGTTCCAAGACCGAGCTGTGAACTC
CTTCCAAAAGGAGGAAGCAGTGTTGCATTCTCTGTCCAGTAAGCCACTGTGGACCCTGTGGACCTGTGAGGAAGCGTGAACTC
CCTGCCCCTGCAAGGCTCTGCCGCAATGGAGCCCCAAGAACACAAAGATGAACCCAGTGCACCAGCACCCACTGTGGAAGCGTGAACTC
CTCTGCAAGGCTCTGCCGCAATGGAGCCCCAAGAACACAAAGATGAACCCAGTGCACTGCAGCCAGTAACTT
TGTGCTTGGACGATGCCCCAAGGGAAGAGGGAGATGAAGTGACTTGCCGTGCCTTGCACAGTGAACTTTCCCAGAGCGAAGATGC
TGGGTGTGAGGAAGAGGGAGATGAAGTGACTTGCCGTGCCTTGCACAGTGAACTTTCCCAGAGCGAAGATGC
CGTAATATTAAGAACCAAATCATTGCCTTCCTCAAGTTGCTCCTGTGGGAGCCTTGCACAGTGAACCTGTAATACAAACAT
GGTAGCTGGATGGTATTCATTGCCTTCCTCAAGTTGTGTCTGCTCCATCCAGTCCATTCCAGACCCGGTGTAATACAAACTTC
GTGTTCAGCTCAAGGCCCGGCTATTCATTGCCTTCCTCAAGTTGTGTCTGCTCCATCCAGTCCATTCCAGACCCGGTGTAATACAAACTTC
TGTCCAGCTCCTGAAAAGAGATCTTAATTCCTTGAATACCTCTATGGTCTCCACTGGTGCTGAGGTCAACACCTAAG
ACGGTTTTCGTCAGTCACCCCTGGATCTGGGTGA
```

*FIG. 5B*

PCR products (base pairs).

Fragment 1
5' primer TAAATCGAATTCCCACCATGTCACCTTTTCTCTTGCAGGCG (SEQ ID NO: 9)
3' primer CCGGGAACATTCTGACCACTTCGAC (SEQ ID NO: 10)
undigested 1762 bp
digested 353 bp Fragment 2
5' primer TAAATCGAATTCCCACCATGTCACCTTTTCTCTTGCAGGCG (SEQ ID NO: 9)
3' primer CCGGGAACATTCTGACCACTTCGAC (SEQ ID NO: 10)
undigested 1762 bp
digested 293 bp Fragment 3
5' primer CTGCCTCTGCTGTGCGTCGGTCGC (SEQ ID NO: 11)
3' primer GCATCTTCGCTCTGGGAAAGTTATC (SEQ ID NO: 12)
undigested 3189 bp
digested 187 bp Fragment 4
5' primer TAAATCGAATTCCCACCATGTCACCTTTTCTCTTGCAGGCG (SEQ ID NO: 9)
3' primer CCGGGAACATTCTGACCACTTCGAC (SEQ ID NO: 10)
undigested 1762 bp
digested 667 bp Fragment 5
5' primer CTGCCTCTGCTGTGCGTCGGTCGC (SEQ ID NO: 11)
3' primer GCATCTTCGCTCTGGGAAAGTTATC (SEQ ID NO: 12)
undigested 3189 bp
digested 1796 bp

FIG. 6A

Truncated EST18 nucleotide sequence plus Streptavidin-Tag: SEQ ID NO: 7

```
ATGGAGTGCGCCCCTCCTGCTCGCGTGTGCCTGCCCTTCCCGGCTGCCTGCGTGCGGAGGGCCTGCGAGGGCCTGGGGCTGGGGGCG
CGTGGCCAAGGCGCTCCAGCTGTGCTGCTCCTCTGTTGTCACGCCCAGTAGAACAGCCCGGCCCGTGCGTGTCCAGTGACACAGCAGCGGCG
CCAGCGGATTAAATGATGATTACGTCTCTTTGTCACGCGCAGTAGAAGTAGACTCAGCGGCGGTCATATATTTCAGCATTTGGACAGGA
TTGCACAACGGCAGGAAAAAGCGATCGGCGCAGATGCCAGAGTCCTCCTGCACTACTGCCAGTTGTCCAGATTTCAGCATTTGGACAGGA
ACTGCACTTAGAACTTAAGCCCTCGGCAATGCTTCTATCAGGGATTTGAGCAGTCACTTTATTGTCCAGAAATGACAGCTCCTCCTGTCGCTTCAG
AGACTCAGAGAAACCCGAGGTGCAGGTTTCAGGTTTAATAAGGACACGCATCCTCACGTACTGCTCCCAAGTCACATTCCCCAAGTCACATTCCCCA
ACGTGTGCTGGCTTGTCTCAGGTTTAATAAGGACACGCATCCTCACGTACTGCTCCCAAGTCACATTCCCCAAGTCACATTCTCAGAGTCGAGAG
GGAACACACAGCTCCCGGCTACCCCGGCCGGAATTATCGCTGGCAATTATCCCAAGCAGCAGGAGAAGATCCAGCGGT
ACCGTGGCTACCCCGGCTCTGCGCCGGAATTATCGCAAAAGCAGGTTGCAAAAGCAGCATTTTTGTGGACGCATCTCCCAAGCCTCCCACAGA
ACAGAGTATCACCATCGAAGGTTGCAAAAGCAGCATTTTTGTGGACGCATCTCCCAAGCCTCCCACAGA
GGACACCTATCTAAGGTTTGATGAATATATCAAGACAAGAAATATCAGCAGCTGGAAAATGTCACCACATACATTCTCACA
ATGTGGAAACCCTCGTGTGGCAGACAATGGGGAAAAATGGTGGAAATGTCACCACATACATTCTCACA
GTAATGAACATGGTTTCTGGCCTATTTAAAGATGGAAGTGACTATTGGAAGTGACATAAACGTGGTTGTGAGCTAATTCT
TCTGGAACAAGAACCTGGAGGATTATTGATCAACACCAGTCTCTGAATAGTTTTGTCAATGGCAGTCTG
CCCTCATTGGAAAGAATGGCAAGACACATGATCATGCCATCTAACAGTACCGAAGTTGATATTTGTACCATCAATGAGGACACAGG
CCATGTGACACTCTAGGGTTTGCCCCCGACTCTAAGTCCTCTAAACTTTGGCTTCATCAGTTGCTCGACGAGAAGGAATCCCTGCA
ACTTGGCCTTGCCTTCACCATCGCTCATGAGTCAGGGCCACAACTTTGGTATGATGATTCACGACCGAGTGTTTTCATGGTGTCTTCTTGCAGCCAG
GAAAGGCTGAAGGAAATCATGATCTCCCACACTCAGCGCGGGTGTCTAGTGACACAGTGTAAATGGAGCCAAGACAGTATAAATACC
TATCTCAAGAATACCAGGACAGATTTATGATGCTGACACAGTGTAAATGGAGCCAAGACCAAGTTATGCAGCC
TTGGTTTTGTGAAGGATATTTGCAAATCACTTTGGTGCCACCGAGTAGGCCAGTGTGAGACCAAGTTTATGCCCGCA
GCAGAAGGGACCGTTTGTGGCTTGTGAGTATGTGGTGTCGGCTAAAGTGTTCCCGGAAGTGTTCAAGTTCCAGGAGA
CATCCACGCCAGTGGTCCGCCAAGCCTTCAGAATATTCGTCAGTATGGTGGCATATTCTGTCGCCAGTTCATCAGCTGTGCAGCC
GACACTGCAATAACCCCAAGCCTTCAGAATATTCGTCAGTATGGTGGCATATTCTGTCGCCAGTTCATCAGCTGTGCAATATT
AACCCTTGCAATGAAAAATAGCTTGGATTTTGGAAGCCGCTTGGAAGCCACCCCAGTTCGAAAAAATAA
```

FIG. 7

Truncated EST18 protein sequence plus Streptavidin-Tag: SEQ ID NO: 8

MECALLLACAFPAAGSGPPRGLAGLGRVAKALQLCCLCCASVAAALASDSSSGASGLNDDYVFVTPVEVDSAGSYISHDI
LHNGRKKRSAQNARSSLHYRFSAFGQELHLELKPSAILSSHFIVQVLGKDGASETQKPEVQQCFYQGFIRNDSSSSVAVS
TCAGLSGLIRTRKNEFLISPLPQLLAQEHNHSSPAGHHPHVLYKRTAEEKIQRYRGYPGSGRNYPGYSPSHIPHASQSRE
TEYHHRRLQKQHFCGRRKKYAPKPPTEDTYLRFDEYGSSGRPRRSAGKSQKGLNVETLVVADKKMVEKHGKGNVTTYILT
VMNMVSGLFKDGTIGSDINVVVSLILEQEPGGLLINHHADQSLNSFCQWQSALIGKNGKRHDHAILLTGFDICSWKNE
PCDTLGFAPISGMCSKYRSCTINEDTGLGLAFTIAHESGHNFGMIHDGEGNPCRKAEGNIMSPTLTGNNGVFSWSSCSRQ
YLKKFLSTPQAGCLVDEPKQAGQYKYPDKLPGQIYDADTQCKWQFGAKAKLCSLGFVKDICKSLWCHRVGHRCETKFMPA
AEGTVCGLSMWCRQGQCVKFGELGPRPIHGQWSAWSKWSECSRTCGGGVKFQERHCNNPKPQYGGIFCPGSSRIYQLCNI
NPCNENSLDFGSAWSHPQFEK

*FIG. 8*

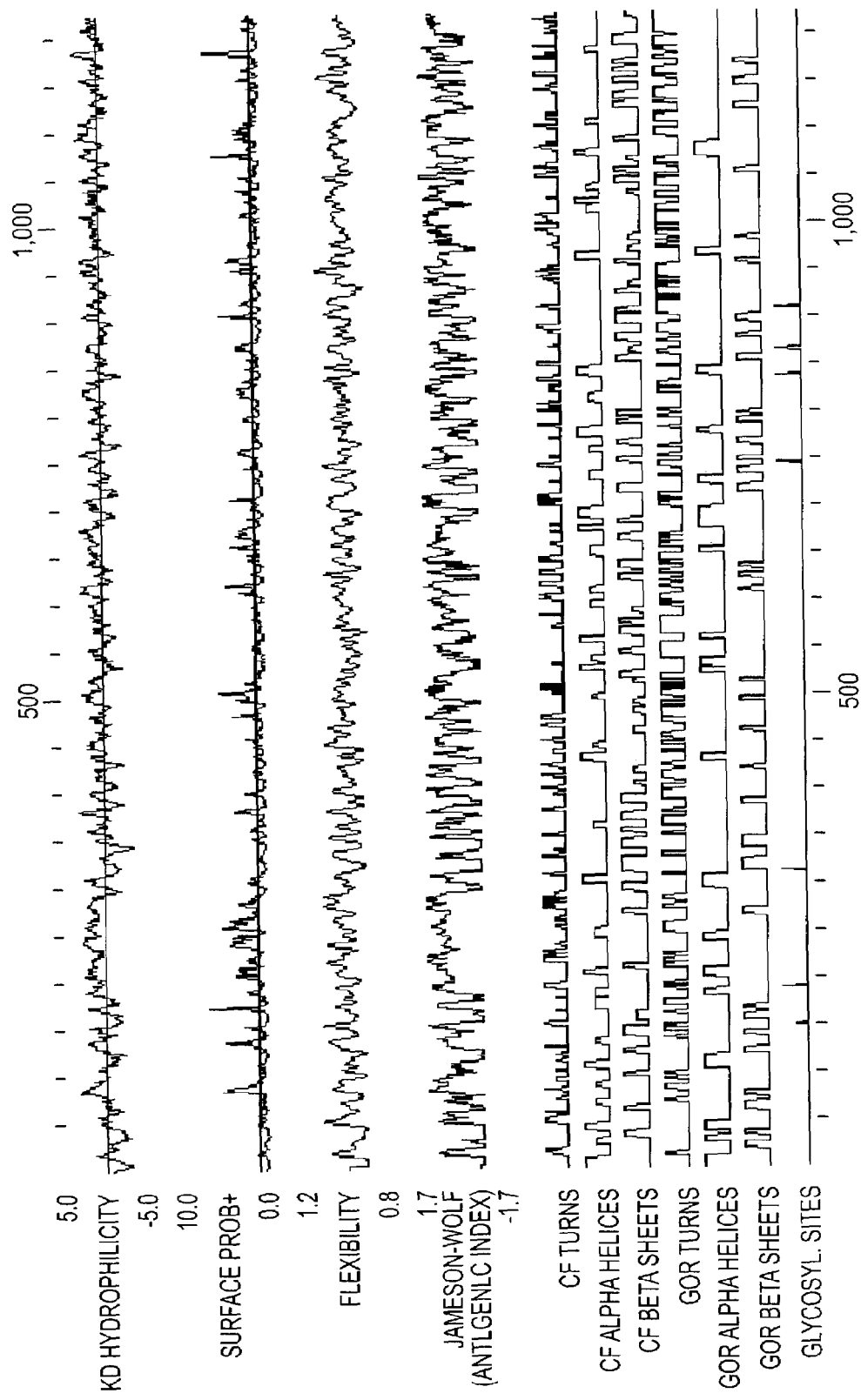

AGGRECANASE MOLECULES

RELATED APPLICATION

This application relies on the benefit of priority of U.S. provisional patent application No. 60/353,680, filed on Jan. 31, 2002, the entire disclosure of which is incorporated by reference.

FIELD OF THE INVENTION

The present invention relates to the discovery of nucleotide sequences encoding novel aggrecanase molecules, aggrecanase proteins and fragments thereof, and processes for producing them. The invention further relates to identification and development of inhibitors of and antibodies to the aggrecanase enzymes. These inhibitors and antibodies may be useful for the treatment of various aggrecanase-associated conditions including osteoarthritis.

BACKGROUND OF THE INVENTION

Aggrecan is a major extracellular component of articular cartilage. It is a proteoglycan responsible for providing cartilage with its mechanical properties of compressibility and elasticity. The loss of aggrecan has been implicated in the degradation of articular cartilage in arthritic diseases. Osteoarthritis is a debilitating disease which affects at least 30 million Americans (MacLean et al., *J Rheumatol* 25:2213–8 (1998)). Osteoarthritis can severely reduce quality of life due to degradation of articular cartilage and the resulting chronic pain. An early and important characteristic of the osteoarthritic process is loss of aggrecan from the extracellular matrix (Brandt and Mankin, *Pathogenesis of Osteoarthritis*, in Textbook of Rheumatology, WB Saunders Company, Philadelphia, Pa., at 1355–1373 (1993)). The large, sugar-containing portion of aggrecan is thereby lost from the extra-cellular matrix, resulting in deficiencies in the biomechanical characteristics of the cartilage.

A proteolytic activity termed "aggrecanase" is believed to be responsible for the cleavage of aggrecan thereby having a role in cartilage degradation associated with osteoarthritis and inflammatory joint disease. Research has been conducted to identify the enzymes responsible for the degradation of aggrecan in human osteoarthritic cartilage. At least two enzymatic cleavage sites have been identified within the interglobular domain of aggrecan. One enzymatic cleavage site within the interglobular domain of aggrecan ($Asn^{341}$-$Phe^{342}$) has been observed to be cleaved by several known metalloproteases. Flannery et al., *J Biol Chem* 267:1008–14 (1992); Fosang et al., *Biochemical J.* 304:347–351 (1994). Cleavage at a second aggrecan cleavage site within aggrecan ($Glu^{373}$-$Ala^{374}$) due to IL-1 induced cartilage aggrecan cleavage results in the generation of an aggrecan fragment found in human synovial fluid (Sandy et al., *J Clin Invest* 69:1512–1516 (1992); Lohmander et al., Arthritis Rheum 36: 1214–1222 (1993); Sandy et al., *J Biol Chem* 266: 8683–8685 (1991)). Aggrecan cleavage at ($Glu^{373}$-$Ala^{374}$) has been attributed to aggrecanase activity (Sandy et al., *J Clin Invest* 69:1512–1516 (1992). This $Glu^{373}$-$Ala^{374}$ cleavage site will be referred to as the aggrecanase cleavage site.

Recently, identification of two enzymes, aggrecanase-1 (ADAMTS4) and aggrecanase-2 (ADAMTS-11) within the "Disintegrin-like and Metalloprotease with Thrombospondin type 1 motif" (ADAMTS) family have been identified which are synthesized by IL-1 stimulated cartilage and cleave aggrecan at the $Glu^{373}$-$Ala^{374}$ site (Tortorella et al., *Science* 284:1664–6 (1999); Abbaszade et al., *J Biol Chem* 274: 23443–23450 (1999)). It is possible that these enzymes could be synthesized by osteoarthritic human articular cartilage. It is also contemplated that there are other, related enzymes in the ADAMTS family which are capable of cleaving aggrecan at the $Glu^{373}$-$Ala^{374}$ bond and could contribute to aggrecan cleavage in osteoarthritis. Therefore, there is a need to identify various aggrecanase enzymes and determine ways to block their enzymatic activity.

SUMMARY OF THE INVENTION

The present invention is directed to the identification of novel aggrecanase protein molecules capable of cleaving aggrecan, nucleotide sequences which encode the aggrecanase enzymes, and processes for the production of aggrecanases. These enzymes are contemplated to be characterized as having proteolytic aggrecanase activity. The invention further includes compositions comprising these enzymes.

The invention also includes antibodies to these enzymes, in one embodiment, for example, antibodies that block aggrecanase activity. In addition, the invention includes methods for identifying and developing inhibitors of aggrecanase which block the enzyme's proteolytic activity. These inhibitors and antibodies may be used in various assays and therapies for treatment of conditions characterized by the degradation of articular cartilage. This invention provides nucleotide molecules that encode novel aggrecanase proteins. Accordingly, in one embodiment, the invention features an isolated DNA molecule comprising a DNA sequence chosen from: nucleotide #1 to nucleotide #3663 of SEQ ID NO: 1 (FIGS. 1A and 1B); fragments of SEQ ID NO: 1 which encode polypeptides or proteins that exhibit aggrecanase activity; variants of SEQ ID NO: 1 that encode proteins or polypeptides that exhibit aggrecanase activity, and fragments thereof; sequences which hybridize under stringent conditions with SEQ ID NO: 1; naturally occurring human allelic sequences; and equivalent degenerative codon sequences In another aspect, the invention comprises an isolated aggrecanase protein comprising an amino acid sequence chosen from: amino acid #1 (methionine) to amino acid #1221 (isoleucine) of SEQ ID NO: 2 (FIG. 2); fragments of SEQ ID NO: 2 which exhibit aggrecanase activity, and variants and fragments of aggrecanase proteins that exhibit proteolytic activity, including deletion and substitution mutants. In yet another aspect, the invention provides methods for producing an isolated aggrecanase protein. One such method includes (1) transforming a host cell with a DNA sequence, such as the DNA sequence depicted in SEQ ID NO: 1; (2) culturing the host cell; and (3) purifying the aggrecanase enzyme set forth in SEQ ID NO: 2 that is encoded by the DNA sequence, from the cell culture medium.

The invention also provides antibodies that bind to isolated aggrecanase proteins of the invention. In one embodiment, such an antibody reduces, inhibits or antagonizes aggrecanase activity. The invention further provides methods for developing and identifying inhibitors of aggrecanase activity comprising the use of aggrecanase protein chosen from SEQ ID NO: 2 or a fragment or a variant thereof. In one embodiment, inhibitors of aggrecanase activity prevent cleavage of aggrecan.

Additionally, the invention provides pharmaceutical compositions for inhibiting the proteolytic activity of aggrecanase, wherein the compositions comprise at least one antibody according to the invention and at least one pharmaceutical carrier. The invention also provides methods for inhibiting aggrecanase activity in a mammal comprising administering to the mammal an effective amount of a pharmaceutical composition according to the invention to inhibit aggrecanase activity.

Additional aspects of the disclosure will be set forth in part in the description, and in part be obvious from the description, or may be learned from practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve to illustrate embodiments and not limit the invention.

BRIEF DESCRIPTION OF THE FIGURES AND SEQUENCES

FIGS. 1A and 1B show the full-length nucleotide sequence for ADAMTS-18 (EST18). (SEQ ID NO: 1)

FIG. 2 shows the full-length amino acid sequence for ADAMTS-18, based on the nucleotide sequence of SEQ ID NO: 1. (SEQ ID NO: 2)

FIGS. 3A and 3B show a nucleotide sequence of ADAMTS-18 (EST18). (SEQ ID NO: 3)

FIG. 4 shows the predicted amino acid sequence of ADAMTS-18 based on the nucleotide sequence of SEQ ID NO: 3. (SEQ ID NO: 4)

FIGS. 5A and 5B show a virtual nucleotide sequence for ADAMTS-18, which was identified by Celera database-mining techniques. (SEQ ID NO: 5)

FIG. 6A shows a schematic representation of the PCR primers used for amplification of fragments of a EST18 nucleotide sequence.

FIG. 7 shows a nucleotide sequence encoding for a truncated form of ADAMTS-18 linked to a Streptavidin-tag. (SEQ ID NO: 7)

FIG. 8 shows an amino acid sequence for a truncated form of ADAMTS-18 including a Streptavidin-tag, based on SEQ ID NO: 7. (SEQ ID NO: 8)

FIG. 9 shows a schematic representation of the hydrophobic plot generated for the protein of SEQ ID NO: 2 using the GCG plotstructure program.

DETAILED DESCRIPTION OF THE INVENTION

I. Definitions

Figure 6B:
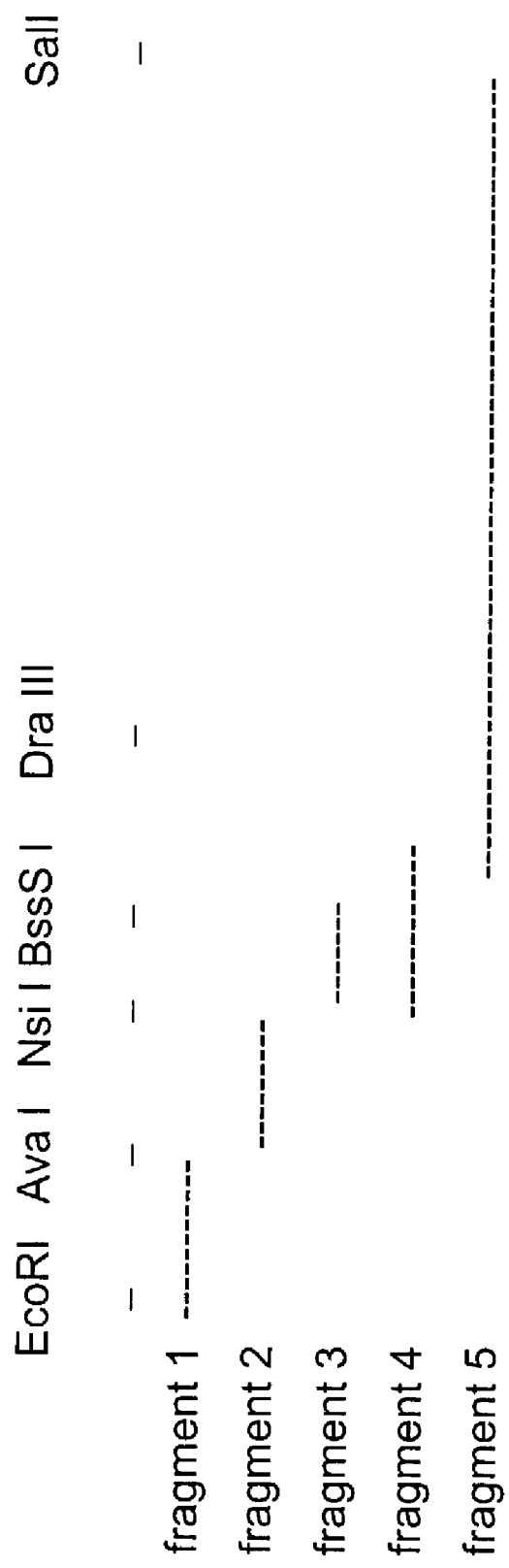
FIG. 6B shows a schematic representation of the overlapping nucleotide sequence fragments of EST18 including sites for restriction enzymes.

In order that the present invention may be more readily understood, certain terms are first defined. Additional definitions are set forth throughout the detailed description.

The term "aggrecanase" refers to a family of polypeptides that are capable of cleaving the aggrecan protein. Generally, these are proteins that cleave aggrecan at the $Glu^{373}$-$Ala^{374}$ aggrecanase cleavage site. Aggrecanases of the present invention encompass but are not limited to the amino acid sequence of SEQ ID NO: 2. The term "aggrecanase" includes naturally occurring variants of the amino acid sequence set forth in SEQ ID NO: 2, as well as fragments of SEQ ID NO: 2 that are active in one or more of the assays provided. For example, included in this definition are amino acid sequences substantially similar or substantially identical to the amino acid of SEQ ID NO: 2 or a fragment thereof; or an amino acid sequence at least about 50%, about 55%, about 60%, about 65%, about 70%, about 75%, about 80%, about 85%, about 90%, about 92%, about 93%, about 94%, about 95%, about 96%, about 97%, about 98% or about 99% identical to the amino acid sequence of SEQ ID NO: 2, or a fragment thereof. The term "aggrecanase" further includes the proteins encoded by the nucleic acid sequence of SEQ ID NO: 1 disclosed, fragments and variants thereof. In one embodiment, the nucleic acids of the present invention will possess a sequence which is either derived from, or is a variant of a natural aggrecanase encoding gene, or a fragment thereof.

The term "aggrecanase activity" refers to at least one cellular process interrupted or initiated by an aggrecanase enzyme binding to aggrecan. Generally, activity refers to proteolytic cleavage of aggrecan by aggrecanase. Aggrecanase activities include, but are not limited to, binding of aggrecanase to aggrecan and cleavage of aggrecan by aggrecanase. Activity can also include a biological response resulting from the binding to or cleavage of aggrecan by aggrecanases of the invention.

The term "antibody" refers to an immunoglobulin or a fragment thereof, and encompasses any polypeptide comprising an antigen-binding site. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. It also includes, unless otherwise stated, antibody fragments such as Fab, $F(ab')_2$, Fv, scFv, Fd, dAb, and other antibody fragments which retain the antigen binding function.

The term "effective amount" refers to a dosage or amount of a composition at least one aggrecanase inhibitor or antibody of the invention that is sufficient to treat a patient.

The term "inhibit" or "inhibition" of aggrecanase or aggrecanase activity refers to a reduction, inhibition of otherwise diminution of at least one activity of aggrecanase due to binding of an inhibitor to the aggrecanase or aggrecan. The reduction, inhibition or diminution of binding can be measured by one of many assays provided. Inhibition of aggrecanase activity does not necessarily indicate a complete negation of aggrecanase activity. A reduction in activity can be, for example, at least about 10%, 20%, 30%, 40%, 50%, 60%, 70%, 80%, 90% or more. In one embodiment, inhibition is measured by a reduction in the detection of cleavage products of aggrecan.

The term "isolated" describes a nucleic acid molecule or polypeptide molecule that is substantially free of its natural environment. For instance, an isolated protein is substantially free of cellular material or other contaminating proteins from the cell or tissue source from which it is derived. The term "isolated" also refers to an aggrecanase protein according to the invention which is free from association with other proteases and retains aggrecanase proteolytic activity. In addition, the term "isolated" refers to nucleic acid molecules that encode aggrecanases of the invention and are free from other cellular material and contaminants.

The term "neoepitope antibody" refers to an antibody that specifically recognizes a new N- or C-terminal amino acid sequence generated by proteolytic cleavage but which does not bind to such an epitope on the intact (uncleaved) substrate.

The term "operative association" with an expression control sequence generally refers to the presence of a specific nucleotide sequence or sequences that control or affect transcription rate or efficiency of a nucleotide molecule linked to the sequence. For example, a promoter sequence that is located proximally to the 5' end of an aggrecanase coding nucleotide sequence may be in operative association with the aggrecanase encoding nucleotide sequence. Expression control sequences include, but are not limited to, for example, promoters, enhancers, and other expression control sequences, or any combination of such elements, either 5' or 3' to an aggrecanase encoding nucleotide sequence in order to control its expression. Not all of these elements are required, however. A skilled artisan can select the appropriate expression control sequences, for example, depending on desired expression levels for the aggrecanases of the invention.

The term "specific binding" of an antibody means that the antibody binds to at least one novel aggrecanase molecule of the present invention and the antibody will not show any significant binding to molecules other than at least one novel aggrecanase molecule. The term is also applicable where, e.g., an antigen binding domain of an antibody is specific for a particular epitope, which is represented on a number of antigens, and the specific binding member (the antibody) carrying the antigen binding domain will be able to bind to the various antigens carrying the epitope. Therefore, it is contemplated that an antibody of the invention will bind to an epitope on multiple novel aggrecanase proteins. Typically, the binding is considered specific when the affinity constant $K_a$ is higher than $10^8$ $M^{-1}$. An antibody is said to "specifically bind" to an antigen if, under appropriately selected conditions, such binding is not substantially inhibited, while at the same time non-specific binding is inhibited. The conditions are usually defined in terms of concentration of antibodies, ionic strength of the solution, temperature, time allowed for binding, concentration of additional molecules associated with the binding reaction (e.g., serum albumin, milk casein), etc. Such conditions are well known in the art, and a skilled artisan using routine techniques can select appropriate conditions.

The term "highly stringent" or "high stringency" describes conditions for hybridization and washing used for determining nucleic acid-nucleic acid interactions. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. The stringency conditions are dependent on the length of the nucleic acid and the base composition of the nucleic acid and can be determined by techniques well known in the art. Generally, stringency can be altered or controlled by, for example, manipulating temperature and salt concentration during hybridization and washing. For example, a combination of high temperature and low salt concentration increases stringency. Such conditions are known to those skilled in the art and can be found in, for example, "Current Protocols in Molecular Biology," John Wiley & Sons, New York (1989), 6.3.1–6.3.6. Both aqueous and nonaqueous conditions as described in the art can be used. One example of highly stringent hybridization conditions is hybridization in 6× sodium chloride/sodium citrate (SSC) at about 45° C., followed by at least one wash in 0.2× SSC, 0.1% SDS at 50° C. A second example of highly stringent hybridization conditions is hybridization in 6×SSC at about 45° C., followed by at least one wash in 0.2×SSC, 0.1% SDS at 55° C. Another example of highly stringent hybridization conditions is hybridization in 6×SSC at about 45° C., followed by at least one wash in 0.2×SSC, 0.1% SDS at 60° C. A further example of highly stringent hybridization conditions is hybridization in 6×SSC at about 45° C., followed by at least one wash in 0.2×SSC, 0.1% SDS at 65° C. Highly stringent conditions include hybridization in 0.5M sodium phosphate, 7% SDS at 65° C., followed by at least one wash at 0.2×SSC, 1% SDS at 65° C.

The phrase "moderately stringent" or "moderate stringency" hybridization refers to conditions that permit a nucleic acid to bind a complementary nucleic acid that has at least about 60%, at least about 75%, or at least about 85%, identity to the nucleic acid; with greater than about 90% identity to the nucleic acid especially preferred. Moderately stringent conditions comprise but are not limited to, for example, hybridization in 50% formamide, 5× Denhart's solution, 5×SSPE, 0.2% SDS at 42° C., followed by washing in 0.2×SSPE, 0.2% SDS, at 65° C. (see, e.g., Sambrook et al., *Molecular Cloning A Laboratory Manual*, Cold Spring Harbor Laboratory Press, 1989).

The phrase "substantially identical" or "substantially similar" means that the relevant amino acid or nucleotide sequence will be identical to or have insubstantial differences (through conserved amino acid substitutions) in comparison to the sequences which are disclosed. Nucleotide and polypeptides of the invention include, for example, those that are at least about 50%, at least about 55%, at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, at least about 98%, or at least about 99% identical in sequence to nucleic acid molecules and polypeptides disclosed.

For polypeptides, at least 20, 30, 50, 100, or more amino acids will be compared between the original polypeptide and the variant polypeptide that is substantially identical to the original. For nucleic acids, at least 50, 100, 150, 300 or more nucleotides will be compared between the original nucleic acid and the variant nucleic acid that is substantially identical to the original. Thus, a variant could be substantially identical in a region or regions, but divergent in others, while still meeting the definition of "substantially identical." Percent identity between two sequences is determined by standard alignment algorithms such as, for example, Basic Local Alignment Tool (BLAST) described in Altschul et al., J. Mol. Biol., 215:403–410 (1990), the algorithm of Needleman et al., J. Mol. Biol., 48:444–453 (1970), or the algorithm of Meyers et al., Comput. Appl. Biosci., 4:11–17 (1988).

The term "treating" or "treatment" refers to both therapeutic treatment and prophylactic or preventative measures. Those in need of treatment may include individuals already having a particular medical disorder as well as those who may ultimately acquire the disorder (i.e., those needing preventative measures). Treatment may regulate aggrecanase activity or the level of aggrecanase to prevent or ameliorate clinical symptoms of at least one diseases. The inhibitors and/or antibodies may function by, for example, preventing the interaction or binding of aggrecanase to aggrecan, or by reducing or inhibiting aggrecanase activity.

The term "variant" refers to nucleotide and amino acid sequences that are substantially identical or similar to the nucleotide and amino acid sequences provided, respectively. Variants can be naturally occurring, for example, naturally occurring human and non-human nucleotide sequences that encode aggrecanase or aggrecanase-like proteins, or be generated artificially. Examples of variants are aggrecanases resulting from alternative splicing of the aggrecanase mRNA, including both 3' and 5' spliced variants of the aggrecanases of the invention, point mutations and other mutations, or proteolytic cleavage of the aggrecanase protein. Variants of aggrecanases of the invention include nucleic acid molecules or fragments thereof and amino acid sequences and fragments thereof, that are substantially identical or similar to other nucleic acids (or their complementary strands when they are optimally aligned (with appropriate insertions or deletions) or amino acid sequences respectively. In one embodiment, there is at least about 50% identity, at least about 55% identity, at least about 60% identity, at least about 65% identity, at least about 70% identity, at least about 75% identity, at least about 80% identity, at least about 85% identity, at least at least about 90%, at least about 92% identity, at least about 93% identity, at least about 94% identity, at least about 95% identity, at least about 96% identity, at least about 97% identity, at least about 98% identity, or at least about 99% identity between a nucleic acid molecule or protein of the invention and another nucleic acid molecule or protein respectively, when optimally aligned. Additionally, variants include proteins or polypeptides that exhibit aggrecanase activity, as defined.

To assist in the identification of the sequences listed in the specification and figures, the following table (Table 1) is provided, which lists the SEQ ID NOs, the figure location, and a brief description of each sequence.

TABLE 1

| SEQUENCES | FIGURES | DESCRIPTION |
|---|---|---|
| | a.a. = amino acid | |
| SEQ ID NO: 1 | FIGS. 1A and 1B | full-length nucleotide sequence of ADAMTS-18 (EST-18) |
| SEQ ID NO: 2 | FIG. 2 | full-length a.a. sequence of ADAMTS-18 encoded by SEQ ID NO: 1 |
| SEQ ID NO: 3 | FIG. 3A and 3B | a nucleotide sequence of ADAMTS-18 (EST18) |
| SEQ ID NO: 4 | FIG. 4 | predicted a.a. sequence of ADAMTS-18 based on SEQ ID NO: 3 |
| SEQ ID NO: 5 | FIG. 5A and 5B | virtual nucleotide sequence for ADAMTS-18 |
| SEQ ID NO: 6 | | zinc binding signature region of aggrecanase-1 |
| SEQ ID NO: 7 | FIG. 7 | truncated EST18 nucleotide sequence including a Streptavidin tag |
| SEQ ID NO: 8 | FIG. 8 | truncated a.a. sequence of EST18 protein including a Streptavidin tag encoded by SEQ ID NO: 7 |
| SEQ ID NO: 9 | FIG. 6A | primer |
| SEQ ID NO: 10 | FIG. 6A | primer |
| SEQ ID NO: 11 | FIG. 6A | primer |
| SEQ ID NO: 12 | FIG. 6A | primer |
| SEQ ID NO: 13 | | peptide sequence |
| SEQ ID NO: 14 | | peptide sequence |
| SEQ ID NO: 15 | | CD-36 binding motif |
| SEQ ID NO: 16 | | primer |
| SEQ ID NO: 17 | | primer |
| SEQ ID NO: 18 | | primer |
| SEQ ID NO: 19 | | primer |
| SEQ ID NO: 20 | | primer |
| SEQ ID NO: 21 | | oligonucleotide |
| SEQ ID NO: 22 | | oligonucleotide |

TABLE 1-continued

| SEQUENCES | FIGURES | DESCRIPTION |
|---|---|---|
| | a.a. = amino acid | |
| SEQ ID NO: 23 | | oligonucleotide |
| SEQ ID NO: 24 | | oligonucleotide |
| SEQ ID NO: 25 | | oligonucleotide |
| SEQ ID NO: 26 | | oligonucleotide |
| SEQ ID NO: 27 | | primer |
| SEQ ID NO: 28 | | primer |
| SEQ ID NO: 29 | | epitope tag |
| SEQ ID NO: 30 | | nucleotide insert |
| SEQ ID NO: 31 | | nucleotide sequence containing an XhoI site |
| SEQ ID NO: 32 | | a 68 base pair adapter nucleotide sequence |
| SEQ ID NO: 33 | | neoepitope sequence |

II. Novel Aggrecanase Molecules

In one embodiment, a nucleotide sequence of an aggrecanase molecule according to the present invention is set forth in SEQ ID NO: 1, including nucleotide #1 to nucleotide #3663 of SEQ ID NO: 1 (FIGS. 1A and 1B). The invention further includes equivalent degenerative codon sequences of the sequence set forth in SEQ ID NO: 1, as well as fragments and variants thereof which encode proteins that exhibit aggrecanase activity. The nucleic acid sequences of the invention include both naturally occurring sequences and variants thereof and those that are artificially generated. Full length nucleotide sequences encoding the aggrecanase molecules of the present invention may be obtained in one embodiment, for example, by using the nucleotide sequence set forth in SEQ ID NO: 3 to design probes for screening for the full-length aggrecanase nucleotide sequence using standard techniques.

The amino acid sequence of the isolated aggrecanase-like molecule is set forth in SEQ ID NO: 2, including amino acid #1 (methionine) to amino acid #1221 (isoleucine) of SEQ ID NO: 2 (FIG. 2).

The invention further includes fragments of the amino acid sequence which encode molecules exhibiting aggrecanase activity.

The invention includes methods for obtaining full length aggrecanase molecules, the nucleotide sequences that encode aggrecanase molecules obtained by the methods and proteins encoded by the nucleotide sequences. Methods for isolation of the full length sequence include, for example, utilizing the aggrecanase nucleotide sequence set forth in SEQ ID NO: 3 (FIGS. 3A and 3B) for designing probes for screening, or otherwise screen for full-length nucleotide sequence using standard procedures known to those skilled in the art.

The human aggrecanase protein or a fragment thereof may be produced by culturing a cell transformed with a DNA sequence chosen from SEQ ID NO: 1 and recovering and purifying from the culture medium a protein characterized by an amino acid sequence set forth in SEQ ID NO: 2, which is substantially free from other proteinaceous materials with which it is co-produced. For production in mammalian cells, the DNA sequence further comprises a DNA sequence encoding a suitable propeptide 5' to and linked in frame to the nucleotide sequence encoding an aggrecanase enzyme.

Human aggrecanase proteins produced by methods of the invention are characterized by having the ability to cleave aggrecan and having an amino acid sequence chosen from SEQ ID NO: 2, variants of the amino acid sequence of SEQ ID NO: 2, including naturally occurring mutant proteins spliced products, and other variants, in which the proteins retain the ability to cleave aggrecan which is characteristic of aggrecanase proteins. These proteins may include a protein which is at least about 30% identical, about 35% identical, about 40% identical, about 45% identical, about 50% identical, about 55% identical, about 60% identical, about 65% identical, about 70% identical, about 75% identical, about 80% identical, about 85% identical, about 90% identical, about 92% identical, about 94% identical, about 95% identical, about 96% identical, about 97% identical, about 98% identical or about 99% identical, to the amino acid sequence shown in SEQ ID NO: 2. Finally, proteins including variations of the sequence depicted in SEQ ID NO: 2, including amino acid changes induced by mutagenesis, chemical alteration, or by alteration of DNA sequence used to produce the protein, whereby the peptide sequence still has aggrecanase activity, are also included in the present invention. The present invention also includes fragments of the amino acid sequence of SEQ ID NO: 2 which retain the activity of aggrecanase protein, and variants of the fragments as well.

III. Identification of Aggrecanase Proteins and DNA Molecules Encoding Them, and Variants Thereof.

It is expected that there are additional human sequences that encode for aggrecanases or related proteins with aggrecanase activity and that other species also have DNA sequences encoding proteins that are variants of human aggrecanase enzymes. The invention, therefore, includes methods for obtaining DNA sequences encoding aggrecanase proteins and variants thereof, DNA sequences obtained by those methods, and proteins or polypeptides encoded by the DNA sequences. One such method entails utilizing a nucleotide sequence of the invention or portions thereof to design probes for screening libraries for the corresponding nucleotide sequence from other species or coding sequences or fragments thereof using standard techniques. Thus, the present invention may include DNA sequences from other species, which encode aggrecanase or aggrecanase-like polypeptides or proteins, which can be obtained using the human aggrecanase nucleotide sequence. The present invention may also include functional fragments of the aggrecanase protein, and DNA sequences encoding such functional fragments, as well as functional fragments of related proteins with aggrecanase or aggrecanase-like activity. The ability of such a fragment to function like an aggrecanase is determinable by using the polypeptide or protein in one of many biological assays described for detecting activity of the aggrecanase protein.

For example, SEQ ID NO: 1, set forth in FIGS. 1A and 1B, was used as a query against GenBank and GenSeq to find similar nucleotide sequences from humans. Several sequences were identified as being similar either to the full-length or partial nucleic acid sequence of SEQ ID NO: 1. The published sequences were identified by the following accession numbers: AJ311903; Ax319854 (sequence 18 from WO 01/183782); AC025284; AC010548; AC009139; AQ407949; AQ309991; AQ543125; AQ052241; Abn89277 (disclosed in WO 02/250258); G65591; G53009; BD040395; Abn 89277; Aas97176; Aad16756; Aad16759; Abq79948; Aas65280; Aad16771; Aad16774; Aas75293; Aas65278; Aac16650; Aah36077; Aba11592; Aba15654; Aba15653; and Aba15655.

In addition, SEQ ID NO: 1 was used to search a database BLASTX which includes translations of the genes in the Genbank database and the protein components of the GenESeq database. The search revealed several human protein sequences which include sequences identified by the following accession numbers: GENESEQP:ABB81460 (disclosed in WO 02/250,258); Genbank:CAC83612; GENESEQP:AAU72893; GENESEQP:AAE09696; GENESEQP:AAE09699; GENESEQP:ABB82162; GENESEQP:AAE09711; GENESEQP:ABG11106; GENESEQP:AAB08954; and GENESEQP:AAB08913.

It is expected that similar sequences exist in non-human species that are likely to encode aggrecanases or aggrecanase-like proteins. Various non-human variants of the aggrecanase protein were identified by searching the BLASTX database using the nucleotide sequence set forth in SEQ ID NO: 1. These include, for example, BAC35556_1 (mouse); AAH34739_1 (mouse); BAC29190_1 (mouse); AAO17380_1 (mouse); BAC33391_1 (mouse); AAG29823_1 (rat); AAD34012_1 (rat); BAA11088_1 (mouse); BAA24501_1 (mouse); AAH40382_1 (mouse); CAA65253_1 (*Bos. tauruas*); CAA93287_1 (*C. elegans*); AAF46065_2 (*D. melanogaster*); AAN17331_1 (*Equus caballus*); AAM50192_1 (*D. melanogaster*); AAF55199_2 (*D. melanogaster*); AAF25805_1 (mouse); AAG37995_1 (*D. melanogaster*); AAG41980_1 (mouse); AAD56356_1 (mouse); AAF56794_3 (*D. melanogaster*); AAF56795_3; GENESEQP:ABB71150 (*D. melanogaster*); GENESEQP:AAB72280 (mouse); GENESEQP:ABB62044 (*D. melanogaster*); GENESEQP:AAB72284 (mouse); GENESEQP:AAB21265 (mouse); GENESEQP:AAY53899 (mouse); GENESEQP:AAY53900 (bovine); GENESEQP:ABB60410 (*D. melanogaster*); GENESEQP:AAB50004 (bovine); GENESEQP:AAY53898 (*C. elegans*); GENESEQP:AAW47030 (bovine); GENESEQP:AAB72287(mouse); NR:25053113 (mouse); NR:20888361 (mouse); NR:23634336 (mouse); NR27721019 (rat); NR27688211 (rat); NR:27712734; NR:20898418 (mouse); NR:27681743 (mouse); NR:21288693 (*Anopheles gambiae*); NR:27705982 (rat); NR:27693936 (rat); NR:27664306 (rat); NR:20861058 (mouse); NR:27681747 (rat); NR:27719839 (rat); NR:25056874 (mouse); and NR:25052431 (mouse).

Several ESTs similar to the nucleotide sequence of SEQ ID NO: 1 are also published in Genbank, including the following accession numbers: AW295437; BF224279; BE674425; BF512077; AA057097; AA057097; AA057408; AV730422; BM696215; BM664487; BG396090; BE253544; AA442575; and AA436819.

It is contemplated, based on the results of the BLAST searches described that the EST18 mRNA is expressed at least in carcinoid tissue, retinoblastoma, retina, testis, hypothalamus, kidney and the brain. Additionally, the gene for EST18 is speculated to be located on chromosome 16 in humans.

The full-length EST18 sequence, set forth in SEQ NO: 1, was further used to search a genomic sequence database provided by Celera for spliced variants of the EST18 mRNA, including, for example, both 5' and 3' spliced variants. Some of the putative spliced variants are identified by accession numbers: Geneseq:aac16650; Geneseq:aah36077; Geneseq:aas65278; Geneseq:aas65279; Geneseq:aas65280; Geneseq:aas97176; Genbank:AJ311903; and Genbank:AX319854. Sequence alignments of these sequences with the EST18 nucleotide sequence suggests that majority of the spliced variants described herein have differences at the 3' ends.

The Celera single nucleotide polymorphism database was searched with the sequence set forth in SEQ ID NO: 1. The table below summaries the results of such a search, which lists the genetic variations found within the EST18 sequence, for example, across different races and ethnicities in humans.

TABLE 2

| SNP name | Source | Allele | Protein Variation | Location |
|---|---|---|---|---|
| hCV3284477 | Celera | T/C | | Intron |
| hCV3284476 | Celera | G/A | Cys(TGC)1057Cys(TGT) | Silent Mutation |
| hCV11516846 | Celera | A/— | | Intron |
| hCV3284474 | Celera | A/T | | Intron |
| hCV3284473 | Celera | A/G | | Intron |
| hCV3284472 | Celera | T/G | | Intron |
| hCV9478412 | dbSNP | A/C | | Intron |
| hCV3284471 | Celera | C/G | | Intron |
| hCV3284470 | Celera | T/A | | Intron |
| hCV3284469 | Celera | T/C | | Intron |
| hCV3284468 | Celera | C/T | | Intron |
| hCV3284467 | Celera | A/G | | Intron |
| hCV3284466 | Celera | T/C | Val(GTA)986Val(GTG) | Silent Mutation |
| hCV3284465 | Celera | C/A | Ala(GCC)955Ser(TCC) | Mis-sense Mutation |
| hCV3284464 | Celera | A/G | | Intron |
| hCV3284463 | Celera | G/C | | Intron |
| hCV3284462 | Celera | T/C | | Intron |
| hCV11516852 | Celera | —/T | | Intron |
| hCV3284461 | Celera | T/C | | Intron |
| hCV3284460 | Celera | C/T | | Intron |
| hCV16210086 | dbSNP | G/A | | Intron |
| hCV11937057 | dbSNP | C/T | | Intron |
| hCV11937062 | dbSNP | C/T | | Intron |
| hCV9602010 | dbSNP | A/G | | Intron |
| hCV9602009 | dbSNP | A/G | | Intron |
| hCV9602008 | dbSNP | T/C | | Intron |
| hCV9602001 | dbSNP | T/G T/G T/G | | Intron |
| hCV11937070 | dbSNP | T/C | | Intron |
| hCV2852198 | Celera | C/A | | Intron |
| hCV2852197 | Celera | A/G | | Intron |
| hCV2828126 | Celera | C/A | | Intron |
| hCV2828125 | Celera | T/C | | Intron |
| hCV2828124 | Celera | G/C | | Intron |
| hCV2828123 | Celera | T/C | | Intron |
| hCV7606027 | dbSNP | T/C | | Intron |
| hCV7606023 | dbSNP | G/A | | Intron |
| hCV7606022 | dbSNP | T/C | | Intron |
| hCV2828122 | Celera | T/— | | Intron |
| hCV2828121 | Celera | C/T | | Intron |
| hCV11935339 | dbSNP | G/A | | Intron |
| hCV16018212 | dbSNP | T/G | | Intron |
| hCV2828119 | dbSNP Celera | G/A A/G G/A | | Intron |
| hCV2828118 | dbSNP Celera | A/T T/A T/A T/A | | Intron |
| hCV2381371 | dbSNP | A/G G/A G/A G/A | | Intron |
| hCV2828117 | dbSNP | G/A G/A G/A | | Intron |
| hCV2381370 | dbSNP | A/G A/G G/A | | Intron |
| hCV11669939 | Celera | T/— | | Intron |
| hCV2381369 | dbSNP | G/A A/G A/G | | Intron |
| hCV2828115 | Celera | T/G | | Intron |
| hCV7606016 | dbSNP | G/A | | Intron |
| hCV7606010 | dbSNP Celera | C/T C/T | | Intron |
| hCV11669940 | dbSNP Celera | G/A A/G | | Intron |
| hCV9478393 | dbSNP | C/T | | Intron |
| hCV2828114 | Celera | C/G | | Intron |
| hCV11439282 | dbSNP | C/T | | Intron |
| hCV2828113 | dbSNP Celera | C/G G/C | | Intron |
| hCV2828112 | Celera | G/A | | Intron |
| hCV11439283 | dbSNP | C/G | | Intron |
| hCV7606009 | dbSNP | T/C | | Intron |
| hCV16139205 | dbSNP | C/T | | Intron |
| hCV11669941 | Celera | A/— | | Intron |
| hCV11669944 | Celera | A/— | | Intron |
| hCV11439286 | dbSNP | A/G | | Intron |
| hCV16271258 | dbSNP | A/G | | Intron |
| hCV16271259 | dbSNP | C/T | | Intron |
| hCV2828109 | dbSNP Celera | T/C C/T | | Intron |
| hCV2828108 | dbSNP Celera | C/T C/T | | Intron |
| hCV9478420 | dbSNP | A/C A/C A/C A/C | | Intron |
| hCV2828107 | dbSNP Celera | T/C T/C | | Intron |
| hCV2828106 | dbSNP Celera | C/T C/T | | Intron |
| hCV2828105 | dbSNP Celera | C/T T/C | | Intron |
| hCV2828104 | Celera | G/A | | Intron |
| hCV16271260 | dbSNP | A/G | | Intron |
| hCV3284520 | Celera | C/A | | Intron |
| hCV3284521 | dbSNP Celera | G/A A/G G/A | | Intron |
| hCV11669953 | Celera | T/G | | Intron |

TABLE 2-continued

| SNP name | Source | Allele | Protein Variation | Location |
|---|---|---|---|---|
| hCV11669954 | Celera | T/A | | Intron |
| hCV11669955 | Celera | C/A | | Intron |
| hCV16271264 | dbSNP | C/T | | Intron |
| hCV11439287 | dbSNP | T/C | | Intron |
| hCV2828103 | dbSNP Celera | A/G A/G | | Intron |
| hCV2828102 | dbSNP Celera | T/A A/T | | Intron |
| hCV2828101 | Celera | T/A | | Intron |
| hCV2828100 | Celera | A/G | | Intron |
| hCV2828099 | Celera | C/T | | Intron |
| hCV11439288 | dbSNP | A/G G/A A/G A/G | | Intron |
| hCV11439289 | dbSNP HGBASE | G/C C/G G/C C/G C/G | | Intron |
| hCV2828097 | Celera | C/A | | Intron |
| hCV2828096 | Celera | C/A | | Intron |
| hCV2828095 | Celera | C/T | | Intron |
| hCV11669963 | Celera | C/G | | Intron |
| hCV2828094 | Celera | C/T | | Intron |
| hCV11669964 | Celera | G/A | | Intron |
| hCV11669965 | Celera | A/G | | Intron |
| hCV11669967 | Celera | A/G | | Intron |
| hCV11669968 | Celera | A/G | | Intron |
| hCV11439290 | dbSNP | G/T | | Intron |
| hCV11439291 | dbSNP | A/G | | Intron |
| hCV9478400 | dbSNP | C/T | | Intron |
| hCV7606003 | dbSNP | G/C | | Intron |
| hCV16210093 | dbSNP | T/C | | Intron |
| hCV2381366 | dbSNP | C/T T/C C/T C/T | | Intron |
| hCV2828091 | dbSNP Celera | C/T T/C C/T C/T C/T | | Intron |
| hCV11439294 | dbSNP | C/G | | Intron |
| hCV2828090 | Celera | G/C | | Intron |
| hCV2828089 | dbSNP Celera | A/T A/T | | Intron |
| hCV2828088 | Celera | A/G | | Intron |
| hCV2828087 | Celera | T/C | | Intron |
| hCV2828086 | dbSNP Celera | A/C C/A | | Intron |
| hCV16271265 | dbSNP | A/G | | Intron |
| hCV2828084 | Celera | T/C | | Intron |
| hCV11669971 | Celera | A/— | | Intron |
| hCV2828082 | Celera | T/G | | Intron |
| hCV2828081 | Celera | C/T | | Intron |
| hCV16261553 | dbSNP | C/T | | Intron |
| hCV7605998 | dbSNP | G/A A/G | | Intron |
| hCV9478310 | dbSNP | G/C C/G | | Intron |
| hCV16261554 | dbSNP | A/G | | Intron |
| hCV15845773 | dbSNP | C/G | | Intron |
| hCV7605997 | dbSNP | C/A A/C | | Intron |
| hCV2381364 | dbSNP | T/C C/T C/T C/T C/T C/T | | Intron |
| hCV7605993 | dbSNP | A/G G/A | | Intron |
| hCV7605992 | dbSNP | A/G | | Intron |
| hCV11669973 | Celera | —/A | | Intron |
| hCV7605991 | dbSNP | T/C | | Intron |
| hCV7605987 | dbSNP | C/T | | Intron |
| hCV15816829 | dbSNP | T/C | | Intron |
| hCV2381363 | dbSNP | T/G G/T T/G | | Intron |
| hCV7605980 | dbSNP | C/A | | Intron |
| hCV7605979 | dbSNP | A/G | | Intron |
| hCV2828079 | dbSNP Celera | T/C C/T | | Intron |
| hCV11669974 | Celera | —/A | | Intron |
| hCV11439309 | dbSNP | T/C C/T C/T C/T | | Intron |
| hCV7605972 | dbSNP Celera | T/C C/T | | Intron |
| hCV7605971 | dbSNP | T/A | | Intron |
| hCV2828078 | Celera | G/C | | Intron |
| hCV11669976 | Celera | T/C | | Intron |
| hCV2828077 | Celera | C/T | | Intron |
| hCV11669977 | Celera | G/T | | Intron |
| hCV2381361 | dbSNP | C/T T/C T/C | | Intron |
| hCV2381360 | dbSNP | A/T T/A A/T | | Intron |
| hCV11439314 | dbSNP | T/C | | Intron |
| hCV2828076 | dbSNP Celera | T/A T/A | | Intron |
| hCV2828074 | Celera | T/A | | Intron |
| hCV7605963 | dbSNP Celera | C/G C/G | | Intron |
| hCV7605957 | dbSNP | A/C | | Intron |
| hCV2828072 | Celera | C/T | | Intron |
| hCV2828071 | Celera | A/G | | Intron |
| hCV16016767 | dbSNP | G/A | | Intron |
| hCV7605956 | dbSNP | G/T G/T | | Intron |

TABLE 2-continued

| SNP name | Source | Allele | Protein Variation | Location |
|---|---|---|---|---|
| hCV7605955 | dbSNP | C/A A/C | | Intron |
| hCV2828070 | dbSNP Celera | T/C C/T T/C | | Intron |
| hCV2828069 | dbSNP Celera | T/C T/C | | Intron |
| hCV2828068 | dbSNP Celera | G/A G/A G/A | | Intron |
| hCV16261555 | dbSNP | G/A | | Intron |
| hCV16271253 | dbSNP | A/G | | Intron |
| hCV16261562 | dbSNP | T/C | | Intron |
| hCV7605948 | dbSNP | T/C C/T | | Intron |
| hCV7605947 | dbSNP | C/G C/G | | Intron |
| hCV16271271 | dbSNP | C/G | | Intron |
| hCV11669982 | Celera | G/— | | Intron |
| hCV11669983 | Celera | A/C | | Intron |
| hCV11669985 | Celera | —/A | | Intron |
| hCV15784638 | dbSNP | AAAA/— | | Intron |
| hCV2828065 | dbSNP Celera | C/T C/T C/T | | Intron |
| hCV2828064 | dbSNP Celera | A/G G/A | | Intron |
| hCV2828063 | dbSNP Celera | C/G C/G | | Intron |
| hCV9478268 | dbSNP | C/T | | Intron |
| hCV2828062 | dbSNP Celera | G/A A/G | | Intron |
| hCV16261563 | dbSNP | A/G | | Intron |
| hCV16261564 | dbSNP | A/G | | Intron |
| hCV16271266 | dbSNP | C/T | | Intron |
| hCV11669986 | Celera | —/A | | Intron |
| hCV2828060 | dbSNP Celera | C/A A/C A/C | | Intron |
| hCV2828059 | dbSNP Celera | T/C T/C T/C | | Intron |
| hCV2828058 | dbSNP Celera | G/C C/G G/C | | Intron |
| hCV2828057 | dbSNP Celera | C/T C/T | | Intron |
| hCV2828056 | dbSNP Celera | C/T C/T | | Intron |
| hCV2828055 | dbSNP Celera | C/A A/C | | Intron |
| hCV2828054 | dbSNP Celera | A/T A/T | | Intron |
| hCV16271272 | dbSNP | T/C | | Intron |
| hCV16261571 | dbSNP | G/A G/A | | Intron |
| hCV16261572 | dbSNP | G/A | | Intron |
| hCV16261573 | dbSNP | G/C | | Intron |
| hCV15784665 | dbSNP | —/CTA | | Intron |
| hCV16016733 | dbSNP | A/G | | Intron |
| hCV11669989 | dbSNP Celera | T/C C/T T/C | | Intron |
| hCV11669990 | dbSNP Celera | T/C T/C C/T | | Intron |
| hCV16261580 | dbSNP | A/T | | Intron |
| hCV16271273 | dbSNP | A/G | | Intron |
| hCV16261582 | dbSNP | G/C | | Intron |
| hCV11669992 | Celera | G/T | | Intron |
| hCV15845774 | dbSNP | T/C T/C | | Intron |
| hCV16016736 | dbSNP | C/T | | Intron |
| hCV2828045 | Celera | C/T | | Intron |
| hCV2828044 | Celera | A/G | His(CAC)244Tyr(TAC) | Mis-sense Mutation |
| hCV2828043 | dbSNP Celera | T/G G/T | | Intron |
| hCV2828042 | Celera | C/T | | Intron |
| hCV2828041 | Celera | G/A | | Intron |
| hCV11439320 | dbSNP | A/G A/G | | Intron |
| hCV2828040 | dbSNP Celera | G/A A/G | | Intron |
| hCV11669993 | Celera | T/A | | Intron |
| hCV2828039 | Celera | A/C | | Intron |
| hCV16018201 | dbSNP | G/A | | Intron |
| hCV11669994 | Celera | G/A | | Intron |
| hCV2828038 | Celera | G/A | | Intron |
| hCV2828037 | Celera | A/G | | Intron |
| hCV2828036 | dbSNP Celera | G/A A/G | | Intron |
| hCV2828035 | dbSNP Celera | T/C T/C T/C | | Intron |
| hCV11669995 | dbSNP Celera | A/G G/A | | Intron |
| hCV11439321 | dbSNP | G/C G/C | | Intron |
| hCV11439324 | dbSNP | C/G C/G | | Intron |
| hCV7605946 | dbSNP | T/C T/C C/T C/T | | Intron |
| hCV2828033 | Celera | C/G | | Intron |
| hCV2828032 | Celera | A/G | | Intron |
| hCV2381355 | dbSNP | G/C C/G G/C C/G | | Intron |
| hCV2381354 | dbSNP | A/G G/A G/A A/G | | Intron |
| hCV16016737 | dbSNP | G/A | | Intron |
| hCV16016738 | dbSNP | A/G | | Intron |
| hCV2381353 | dbSNP | C/T C/T C/T T/C | | Intron |
| hCV16018237 | dbSNP | T/C | | Intron |
| hCV2381352 | dbSNP | C/T C/T T/C C/T | | Intron |
| hCV2381351 | dbSNP | T/C C/T C/T T/C | | Intron |
| hCV15864249 | dbSNP | A/C | | Intron |
| hCV11439333 | dbSNP | C/A | | Intron |
| hCV11439334 | dbSNP | A/C A/C | | Intron |

TABLE 2-continued

| SNP name | Source | Allele | Protein Variation | Location |
|---|---|---|---|---|
| hCV2381349 | dbSNP | T/C T/C T/C T/C | | Intron |
| hCV2828031 | dbSNP Celera | C/T T/C T/C T/C T/C | | Intron |
| hCV2828030 | dbSNP Celera | C/T C/T C/T C/T | | Intron |
| hCV2828029 | Celera | C/T | | Intron |
| hCV2381348 | dbSNP | C/T C/T C/T | | Intron |
| hCV2381347 | dbSNP | A/T A/T T/A | | Intron |
| hCV2828028 | Celera | C/G | | Intron |
| hCV16018247 | dbSNP | T/A | | Intron |
| hCV16018248 | dbSNP | G/C | | Intron |
| hCV2828027 | Celera | A/G | | Intron |
| hCV16016748 | dbSNP | A/T | | Intron |
| hCV16016749 | dbSNP | A/G | | Intron |
| hCV16018249 | dbSNP | C/T | | Intron |
| hCV9606709 | dbSNP | C/T C/T C/T C/T C/T | | Intron |
| hCV2828026 | dbSNP Celera | C/T C/T | | Intron |
| hCV16016750 | dbSNP | G/C | | Intron |
| hCV9606713 | dbSNP | G/A G/A | | Intron |
| hCV16016754 | dbSNP | G/C | | Intron |
| hCV2828025 | Celera | G/A | | Intron |
| hCV9606714 | dbSNP | T/C | | Intron |
| hCV2828024 | Celera | G/A | | Intron |
| hCV2381346 | dbSNP | C/T T/C T/C T/C | | Intron |
| hCV2381345 | dbSNP | G/A A/G A/G G/A | | Intron |
| hCV2828023 | Celera | T/A | | Intron |
| hCV2828022 | Celera | T/A | | Intron |
| hCV2381344 | dbSNP Celera | A/T A/T A/T T/A A/T | | Intron |
| hCV2381343 | dbSNP | C/T C/T C/T C/T | | Intron |
| hCV2381342 | dbSNP | C/G C/G C/G G/C | | Intron |
| hCV16018211 | dbSNP | C/T | | Intron |
| hCV2381341 | dbSNP | C/G G/C C/G G/C G/C | | Intron |
| hCV11669997 | Celera | —/A | | Intron |
| hCV2828020 | Celera | G/A | | Intron |
| hCV11439337 | dbSNP | A/T | | Intron |
| hCV2828019 | Celera | A/G | | Intron |
| hCV11669998 | Celera | A/— | | Intron |
| hCV2828017 | Celera | C/A | | Intron |
| hCV2828016 | Celera | C/G | | Intron |
| hCV2828015 | Celera | C/G | | Intron |
| hCV2828014 | Celera | G/A | | Intron |
| hCV2828013 | Celera | C/T | | Intron |
| hCV2828012 | Celera | T/C | | Intron |
| hCV15944296 | dbSNP | T/G | | Intron |
| hCV9605371 | dbSNP | C/T | | Intron |
| hCV2381340 | dbSNP | C/T C/T C/T T/C C/T | | Intron |
| hCV2828011 | Celera | G/T | | Intron |
| hCV2828010 | Celera | A/G | | Intron |
| hCV2828009 | Celera | C/T | | Intron |
| hCV2828008 | Celera | A/G | | Intron |
| hCV11670003 | Celera | C/G | | Intron |
| hCV7605903 | dbSNP | C/A | | Intron |
| hCV7605890 | dbSNP | C/T | | Intron |
| hCV2828002 | Celera | A/G | | Intron |
| hCV7605889 | dbSNP | C/G | | Intron |
| hCV2828001 | Celera | C/T | | Intron |
| hCV2828000 | Celera | G/A | | Intron |
| hCV2827999 | Celera | A/G | | Intron |
| hCV2827998 | Celera | T/C | | Intron |
| hCV2827997 | Celera | G/C | | Intron |
| hCV2827996 | Celera | C/G | | Intron |
| hCV2827995 | Celera | —/G | | Intron |
| hCV11670006 | Celera | —/G | | Intron |
| hCV2827993 | Celera | C/G | | Intron |
| hCV2827992 | Celera | A/C | | Intron |
| hCV2827991 | Celera | A/G | | Intron |
| hCV2827990 | Celera | G/A | | Intron |
| hCV2827989 | Celera | G/A | | Intron |
| hCV16080952 | dbSNP | A/G | | Intron |
| hCV2827988 | dbSNP Celera | G/A A/G | | Intron |
| hCV2827987 | Celera | G/A | | Intron |
| hCV11670008 | dbSNP Celera | T/G T/G | | Intron |
| hCV11670009 | Celera | T/— | | Intron |
| hCV2827984 | Celera | G/T | | Intron |

TABLE 2-continued

| SNP name | Source | Allele | Protein Variation | Location |
|---|---|---|---|---|
| hCV2827983 | Celera | G/A | | Intron |
| hCV11670011 | Celera | C/T | | Intron |
| hCV11670012 | Celera | T/A | | Intron |
| hCV11670013 | Celera | A/G | | Intron |
| hCV2827979 | Celera | A/G | | Intron |
| hCV11670014 | Celera | C/T | | Intron |
| hCV2827977 | Celera | A/T | | Intron |
| hCV2827976 | Celera | G/A | | Intron |
| hCV2827975 | Celera | T/A | | Intron |
| hCV2827974 | Celera | T/A | | Intron |
| hCV2827973 | Celera | C/G | | Intron |
| hCV2827972 | Celera | A/G | | Intron |
| hCV2827971 | Celera | C/A | | Intron |
| hCV11439338 | dbSNP | A/G | | Intron |
| hCV2381339 | dbSNP | C/T C/T T/C C/T | | Intron |
| hCV2827970 | Celera | T/C | | Intron |
| hCV2827969 | Celera | T/A | | Intron |
| hCV7605880 | dbSNP | T/C T/C | | Intron |
| hCV7605879 | dbSNP | A/G G/A | | Intron |
| hCV2827968 | Celera | T/C | | Intron |
| hCV2827967 | Celera | G/C | | Intron |
| hCV2827966 | Celera | C/G | | Intron |
| hCV2381338 | dbSNP | A/G G/A A/G | | Intron |
| hCV2827964 | Celera | A/C | | Intron |
| hCV2827963 | dbSNP Celera | C/T C/T | | Intron |
| hCV11439341 | dbSNP | C/T | | Intron |
| hCV2827962 | Celera | A/G | | Intron |
| hCV2827961 | dbSNP Celera | C/T T/C | | Intron |
| hCV11670022 | Celera | —/A | | Intron |
| hCV2827959 | Celera | G/A | | Intron |
| hCV2827958 | Celera | T/C | | Intron |
| hCV2827957 | Celera | C/G | | Intron |
| hCV2827956 | Celera | T/G | | Intron |
| hCV2827955 | Celera | G/C | | Intron |
| hCV2827954 | Celera | T/C | | Intron |
| hCV2827953 | Celera | G/C | | Intron |
| hCV15815639 | dbSNP | C/A | | Intron |
| hCV16142119 | dbSNP | T/A | | Intron |
| hCV2827952 | Celera | C/T | | Intron |
| hCV15816830 | dbSNP | T/C | | Intron |
| hCV1004253 | dbSNP | T/G T/G | | Intron |
| hCV9606740 | dbSNP | C/T | | Intron |
| hCV3189734 | dbSNP Celera | C/T T/C | | Intron |
| hCV9606733 | dbSNP | A/G | | Intron |
| hCV3189733 | Celera | C/G | | Intron |
| hCV3189732 | dbSNP Celera | T/A T/A T/A T/A A/T | | Intron |
| hCV1004252 | dbSNP | C/A A/C A/C C/A C/A | | Intron |
| hCV1004251 | dbSNP | A/T A/T T/A T/A A/T T/A | | Intron |
| hCV11670025 | Celera | G/A | | Intron |
| hCV3189731 | Celera | T/C | | Intron |
| hCV11670028 | Celera | —/A | | Intron |
| hCV3189730 | Celera | G/T | | Intron |
| hCV8560814 | dbSNP Celera | A/G G/A | | Intron |
| hCV11670031 | Celera | A/G | | Intron |
| hCV11670032 | Celera | G/A | | Intron |
| hCV11439346 | dbSNP | C/T | | Intron |
| hCV3189728 | Celera | G/C | | Intron |
| hCV9606725 | dbSNP | C/G | | Intron |
| hCV3189727 | Celera | C/A | | Intron |
| hCV9606724 | dbSNP | C/A | | Intron |
| hCV9606723 | dbSNP | T/C | | Intron |
| hCV9606719 | dbSNP | T/G | | Intron |
| hCV16142120 | dbSNP | G/C | | Intron |
| hCV16142127 | dbSNP | T/A | | Intron |
| hCV3189726 | Celera | T/C | | Intron |
| hCV3189725 | Celera | C/T | | Intron |
| hCV9606718 | dbSNP | C/G | | Intron |
| hCV3189724 | dbSNP Celera | C/T T/C | | Intron |
| hCV2950480 | Celera | G/T | | Intron |
| hCV11670036 | Celera | —/A | | Intron |
| hCV3189723 | Celera | T/A | | Intron |
| hCV2950479 | Celera | C/T | | Intron |
| hCV7605776 | dbSNP | C/T | | Intron |

TABLE 2-continued

| SNP name | Source | Allele | Protein Variation | Location |
|---|---|---|---|---|
| hCV3189722 | Celera | C/T | | Intron |
| hCV2950478 | Celera | C/G | | Intron |

The aggrecanase molecules provided also include factors encoded by sequences similar to those of SEQ ID NO: 1, but which include modifications or deletions that are naturally occurring, for example, allelic variations in the nucleotide sequence which may result in amino acid changes in the protein or artificially engineered proteins. For example, synthetic proteins may wholly or partially duplicate continuous sequences of the amino acid residues of SEQ ID NO: 2. These sequences, by virtue of sharing primary, secondary, or tertiary structural and conformational characteristics with aggrecanase proteins may possess biological properties in common therewith. It is known, for example that numerous conservative amino acid substitutions are possible without significantly modifying the structure and conformation of a protein, thus maintaining the biological properties of the protein. For example, it is recognized that conservative amino acid substitutions may be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) and cysteine (Cys or C). Thus, these modifications and deletions of the native aggrecanase may be employed as biologically active substitutes for naturally-occurring aggrecanase and in the development of inhibitors or other proteins for therapeutic purposes. It can be readily determined whether a given variant of aggrecanase maintains the biological activity of aggrecanase by subjecting both aggrecanase and the variant of aggrecanase, as well as inhibitors thereof, to the assays described in the examples.

Desired amino acid substitutions (whether conservative or non-conservative) can be determined by those skilled in the art at the time such substitutions are desired. For example, amino acid substitutions can be used to identify important amino acid residues of the proteins or polypeptides of the invention, or to increase or decrease the activity of the aggrecanases of the invention described. Exemplary amino acid substitutions are set forth in Table 3.

TABLE 3

Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1, 4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

Other specific mutations of the sequences of aggrecanase proteins described include modifications of glycosylation sites. These modifications may involve O-linked or N-linked glycosylation sites. For instance, the absence of glycosylation or presence of only partial glycosylation can result from amino acid substitutions or deletions at asparagine-linked glycosylation recognition sites. Asparagine-linked glycosylation recognition sites comprise tripeptide sequences which are recognized specifically by appropriate cellular glycosylation enzymes. These tripeptide sequences usually are either asparagine-X-threonine or asparagine-X-serine, where X can be any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of aggrecanase-related proteins will also result in production of a non-glycosylated protein, even if the glycosylation sites are left unmodified.

IV. Novel Aggrecanase Nucleotide Sequences

Nucleic acid sequences within the scope of the invention include isolated DNA and RNA sequences that hybridize to the native aggrecanase DNA sequences disclosed under conditions of moderate to high stringency. Stringent conditions or conditions of high stringency generally refer to hybridization and washing conditions that employ higher temperature and lower salt concentrations. Additionally, inclusion of formamide also increases stringency. For example, hybridization conditions at 60–65° C. in the absence of formamide or at 42° C. with 50% formamide, are both high stringency conditions.

Still a further aspect of the invention are DNA sequences encoding aggrecanase proteins having aggrecanase proteolytic activity or other disclosed or yet undiscovered activities of aggrecanase. Such sequences include nucleotide sequence illustrated in SEQ ID NO: 1, and DNA sequences which, but for the degeneracy of the genetic code, are identical to the DNA sequence of SEQ ID NO: 1 and encode an aggrecanase protein, for example, including the amino acid sequence of SEQ ID NO: 2, or a variant thereof.

Further included in the present invention are DNA sequences which hybridize under high to moderate stringent conditions with the DNA sequence of SEQ ID NO: 1 and encode a protein having the ability to cleave aggrecan. In one embodiment, DNA sequences include those which hybridize under high stringent conditions (see Maniatis et al., Molecular Cloning (A Laboratory Manual), Cold Spring Harbor Laboratory, at 387–389 (1982)). Such stringent conditions comprise, for example, 0.1×SSC, 0.1% SDS, at 65° C. DNA sequences identified by hybridization include, for example, DNA sequences that encode a protein which is at least about 80% identical, at least about 90% identical, or at least about 95% identical to the sequence set forth in SEQ ID NO: 2. DNAs that are equivalents to the DNA of SEQ ID NO: 1 will also hybridize under moderately stringent conditions to the DNA sequence encoding the peptide sequence of SEQ ID NO: 2.

Conditions of moderate stringency are known in the art, and are defined by Sambrook et al. *Molecular Cloning: A Laboratory Manual*, 2 ed. Vol. 1, Cold Spring Harbor Press. (1989). In one embodiment, for example, conditions of moderate stringency include use of a prewashing solution of 5×SSC/0.5% SDS, 1.0 mM EDTA (pH 8.0) and hybridization conditions of about 55° C.–60° C. temperature and washing overnight in 5×SSC overnight at about 55° C. The skilled artisan will recognize that the conditions may be adjusted as necessary according to factors such as the length and composition of the nucleic acid sequences.

Finally, allelic or other variations of the sequences of SEQ ID NO: 1, encoding the amino acid sequence of SEQ ID NO: 2, or peptide sequence variants of SEQ ID NO: 2, that have aggrecanase activity, are also included in the present invention. Additionally, the present invention includes fragments of the DNA sequence shown in SEQ ID NO: 1 and variants of SEQ ID NO: 1, encoding a protein with aggrecanase activity.

Similarly, DNA sequences which encode aggrecanase proteins comprising the sequence set forth in SEQ ID NO: 2 but which differ from SEQ ID NO: 1 in codon usage because of the degeneracies of the genetic code or because of allelic variations (naturally-occurring base changes in the species population which may or may not result in an amino acid change) also encode the novel factors described. Variations in the DNA sequence of SEQ ID NO: 1 which are caused by point mutations or by induced modifications (including insertion, deletion, and substitution) to enhance the activity, half-life or production of the proteins encoded by them are also encompassed by the invention. The DNA sequences of the present invention are useful, for example, as probes for the detection of mRNA encoding aggrecanase in a given cell population. Thus, the present invention includes methods of detecting or diagnosing diseases and genetic disorders involving aggrecanase proteins, or disorders involving cellular, organ or tissue disorders in which aggrecanase is irregularly transcribed or expressed. Antisense DNA sequences may also be used for preparing vectors for gene therapy applications. Antisense DNA sequences are also useful in in vivo methods involving a cell or an organism, for example, introducing an antisense DNA sequence for aggrecanase into a cell in order to study the interaction of the antisense DNA with the endogenous aggrecanase sequences, and further in order to test the capacity of a promoter operatively linked to the antisense DNA sequence in a vector as a measure of how much antisense DNA is produced in a cell.

A further aspect of the invention includes vectors comprising a DNA sequence as described above in operative association with an expression control sequence therefor. These vectors may be employed in a novel process for producing an aggrecanase protein of the invention in which a cell line transformed with a DNA sequence encoding an aggrecanase protein in operative association with an expression control sequence therefor, is cultured in a suitable culture medium and an aggrecanase protein is recovered and isolated therefrom. This process may employ a number of known cells both prokaryotic and eukaryotic as host cells for expression of the protein. The vectors may be used in gene therapy applications. In such use, the vectors may be transfected into cells of a patient ex vivo, and the cells may be reintroduced into a patient. Alternatively, the vectors may be introduced into a patient in vivo through targeted transfection.

V. Production of Aggrecanase Proteins

Another aspect of the present invention provides methods for producing novel aggrecanase proteins. In one embodiment, a method of the present invention involves culturing a suitable cell line, which has been transformed with a DNA sequence, for example, the sequence set forth in SEQ ID NO: 1, and translating the DNA into an aggrecanase protein of the invention, set forth in SEQ ID NO: 2, under the control of known regulatory sequences. The transformed host cells are cultured and the aggrecanase proteins recovered and isolated from the culture medium. The isolated expressed proteins are substantially free from other proteins with which they are co-produced as well as from other contaminants. The recovered isolated protein is contemplated to exhibit proteolytic aggrecanase activity comprising aggrecan cleavage. Thus, the proteins of the invention may be further characterized by the ability to demonstrate aggrecanase proteolytic activity in an assay which determines the presence of an aggrecan-degrading molecule. These assays or the development thereof is within the knowledge of one skilled in the art. Such assays may involve contacting an aggrecan substrate with an aggrecanase molecule and monitoring the production of aggrecan fragments (see for example, Hughes et al., *Biochem J* 305: 799–804 (1995); Mercuri et a., *J Biol. Chem* 274:32387–32395 (1999)). Suitable cells or cell lines may be mammalian cells, such as Chinese hamster ovary cells (CHO). The selection of suitable mammalian host cells and methods for transformation, culturing, amplification, screening, product production and purification are known in the art. (See, e.g., Gething and Sambrook, *Nature,* 293:620–625 (1981); Kaufman et al., *Mol Cell Biol,* 5(7):1750–1759 (1985); Howley et al., U.S. Pat. No. 4,419,446.)) Another suitable mammalian cell line, which is described in the accompanying examples, is the monkey kidney COS-1 cell line. The mammalian CV-1 cells may also be used.

Bacterial cells may also be used as suitable hosts for expression of the proteins or polypeptides of the invention. For example, the various strains of *E. coli* (e.g., HB101, MC1061) are well-known as host cells in the field of biotechnology. Various strains of *B. subtilis, Pseudomonas,* other bacilli and the like may also be employed in the methods of the invention. For expression of the protein in bacterial cells, DNA encoding the propeptide of an aggrecanase is generally not necessary.

Many strains of yeast cells known to those skilled in the art may also be available as host cells for expression of the proteins or polypeptides of the present invention. Additionally, where desired, insect cells may be utilized as host cells in the method of the present invention. See, e.g., Miller et al., *Genetic Engineering,* 8:277–298 (Plenum Press 1986).

Another aspect of the present invention provides vectors for use in a method of expression of these novel aggrecanase proteins. In one embodiment, vectors of the invention contain full length DNA sequences described which encode the novel factors of the invention. Additionally, the vectors contain appropriate expression control sequences permitting expression of the aggrecanase protein sequences. Alternatively, vectors incorporating modified sequences as described above are also embodiments of the present invention. Additionally, the sequence of SEQ ID NO: 1 or other sequences encoding aggrecanase proteins could be manipulated to express composite aggrecanase proteins. Thus, the present invention includes chimeric DNA molecules that encode a recombinant protein including an aggrecanase protein comprising a fragment of SEQ ID NO: 2 linked to a different aggrecanase protein. Such a recombinant or fusion protein can be produced by linking the DNA encoding a fragment of the aggrecanase molecule set forth in SEQ ID NO: 2 in frame with the DNA encoding a different aggrecanase protein. The DNA encoding the aggrecanase protein set forth in SEQ ID NO: 2 or a fragment or variant thereof can be linked either 3' or 5'0 to the DNA encoding a different aggrecanase. Vectors used for the expression of aggrecanase molecules of the invention may be employed in a method of transforming cell lines and usually contain selected regulatory sequences capable of directing the replication and expression of aggrecanase molecules in operative association with DNA sequences of the invention. Regulatory sequences for such vectors are known to those skilled in the art and may be selected depending upon the host cells. Such selection is routine and does not form part of the present invention.

One skilled in the art can construct mammalian expression vectors by employing a sequence comprising, for example, SEQ ID NO: 1 or other DNA sequences encoding aggrecanase-related proteins or other modified sequences and known vectors, such as, for example, pCD (Okayama et al., *Mol Cell Biol,* 2:161–170 (1982)), pJL3, pJL4 (Gough et al., *EMBO J,* 4:645–653 (1985)) and pMT2 CXM. In addition, one skilled in the art can employ a suitable expression vector for expressing a recombinant form of the aggrecanase protein, for example, rA18FS, in an expression system of choice.

The construction of vectors may involve modification of the aggrecanase-related DNA sequences. For instance, aggrecanase cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of aggrecanase or aggrecanase-related proteins. Additionally, the sequence of SEQ ID NO: 1 or other sequences encoding aggrecanases or aggrecanase-related proteins can be manipulated to express a mature aggrecanase or aggrecanase-related protein by deleting aggrecanase encoding propeptide sequences and replacing them with sequences encoding complete propeptides of other aggrecanase proteins.

One skilled in the art can manipulate the sequence of SEQ ID NO: 1 by eliminating or replacing the mammalian regulatory sequences flanking the coding sequence with bacterial sequences to create bacterial vectors for intracellular or extracellular expression by bacterial cells. For example, the coding sequences could be further manipulated (e.g., ligated to other known linkers or modified by deleting non-coding sequences therefrom or altering nucleotides therein by other known techniques). The modified aggrecanase-related coding sequence could then be inserted into a known bacterial vector using procedures such as described in Taniguchi et al., *Proc. Natl. Acad. Sci. USA,* 77:5230–5233 (1980). This exemplary bacterial vector could then be transformed into bacterial host cells and an aggrecanase-related protein expressed thereby. For a strategy for producing extracellular expression of aggrecanase-related proteins in bacterial cells, see, e.g., European patent application EPA 177,343.

Similar manipulations can be performed for the construction of an insect vector (see, e.g. procedures described in published European patent application EPA 155,476) for expression in insect cells. A yeast vector could also be constructed employing yeast regulatory sequences for intracellular or extracellular expression of the factors of the present invention by yeast cells. (See, e.g., procedures described in published PCT application WO 86/00639 and European patent application EPA 123,289.)

A method for producing high levels of a aggrecanase-related protein of the invention in mammalian, bacterial, yeast or insect host cell systems may involve the construction of cells containing multiple copies of the heterologous aggrecanase-related gene. The heterologous gene is linked to an amplifiable marker, e.g., the dihydrofolate reductase (DHFR) gene for which cells containing increased gene copies can be selected for propagation in increasing concentrations of methotrexate (MTX) according to the procedures of Kaufman and Sharp, *J Mol Biol,* 159:601–629 (1982). This approach can be employed with a number of different cell types.

For example, a plasmid containing a DNA sequence for an aggrecanase-related protein of the invention in operative association with other plasmid sequences enabling expression thereof and the DHFR expression plasmid pAdA26SV (A)3 (Kaufman and Sharp, *Mol Cell Biol* 2:1304 (1982)) can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 µM MTX) as described in Kaufman et al., *Mol Cell Biol.,* 5:1750 (1983). Transformants are cloned, and biologically active aggrecanase expression is monitored by the assays described above. Aggrecanase protein expression should increase with increasing levels of MTX resistance. Aggrecanase proteins are characterized using standard techniques known in the art such as pulse labeling with $^{35}$S methionine or cysteine and polyacrylamide gel electrophoresis. Similar procedures can be followed to produce other related aggrecanase-related proteins.

Aggrecanase proteins of the invention can also be expressed as fusion proteins comprising the protein sequence, for example, the sequence set forth in SEQ ID NO: 2 or a fragment or a variant thereof, and for example, a tag, i.e., a second protein or one or more amino acids, from about 2 to 50 amino acids, or from about 50 to about 100 amino acids, which are added to the amino terminus of, the carboxy terminus of, or any point within the amino acid sequence of an aggrecanase protein, or a fragment or variant thereof. Typically, such amino acid tags are made to stabilize the resulting fusion protein or to simplify purification of an expressed recombinant form of the corresponding aggrecanase protein or a fragment or a variant of such protein, including for example, a truncated form of an aggrecanase protein of the invention. Such tags are known in the art. Representative examples of such tags include sequences which encode a series of histidine residues, the epitope tag FLAG, the Herpes simplex glycoprotein D, beta-galactosidase, maltose binding protein, streptavidin tag or glutathione S-transferase.

VI. Generation of Antibodies

The isolated proteins of the present inventions may be used to generate antibodies, either monoclonal or polyclonal, to aggrecanase and/or other aggrecanase-related proteins, using methods of antibody production that are generally known in the art. Thus, the present invention also includes antibodies to aggrecanase or other related proteins. The antibodies include both antibodies that block aggrecanase activity and antibodies that do not. The antibodies may be useful for detection and/or purification of aggrecanase or related proteins, or for inhibiting or preventing the effects of aggrecanase. Aggrecanases of the invention or portions thereof may be utilized to prepare antibodies that specifically bind to aggrecanase.

Antibodies can be made, for example, via traditional hybridoma techniques (Kohler and Milstein, *Nature* 256: 495–499 (1975)), recombinant DNA methods (for example, U.S. Pat. No.4,816,567), or phage display techniques using antibody libraries (Clackson et al., *Nature* 352: 624–628 (1991); Marks et al., *J. Mol. Biol.* 222:581–597 (1991)). For various antibody production techniques, see *Antibodies: A Laboratory Manual*, eds. Harlow et al., Cold Spring Harbor Laboratory (1988).

Proteins are known to have certain biochemical properties including sections which are hydrophobic and sections which are hydrophilic. The hydrophobic sections are most likely to be located in the interior of the structure of the folded protein while the hydrophilic sections are most likely to be located in the exterior of the structure of the folded protein. It is believed that the hydrophilic regions of a protein correspond to antigenic epitopes on the protein. The hydrophobicity of the protein set forth in SEQ ID NO: 2 was determined using the GCG program called plotstructure. The results, as depicted in FIG. 9, indicated that the protein of SEQ ID NO: 2 has several regions that are hydrophilic and therefore, expected to be on the surface of the folded protein. For example, between amino acids 50 and 100, there is a region that is predicted to be hydrophilic as well as antigenic. Such antigenic regions can be employed for the generation of antibodies.

Antibodies of the invention may be used in the treatment of the diseases described below. Antibodies can also be used in the assays and methods of detection described.

VII. Development of Inhibitors

Various conditions such as osteoarthritis are known to be characterized by degradation of aggrecan. Therefore, an aggrecanase protein of the present invention which cleaves aggrecan may be useful for the development of inhibitors of aggrecanase. The invention therefore provides compositions comprising an aggrecanase inhibitor. The inhibitors may be developed using an aggrecanase molecule in screening assays involving a mixture of aggrecan substrate with an inhibitor of aggrecanase activity followed by exposure to aggrecan. Inhibitors can be screened using high throughput processes, such as by screening a library of inhibitors. Inhibitors can also be made using three-dimensional structural analysis and/or computer aided drug design. The method may entail determination of binding sites for inhibitors based on the three dimensional structure of aggrecanase and aggrecan and developing molecules reactive with a binding site on aggrecanase or aggrecan. Candidate molecules are assayed for inhibitory activity. Additional standard methods for developing inhibitors of aggrecanase molecules are known to those skilled in the art. Assays for the inhibitors involve contacting a mixture of aggrecan and an inhibitor with an aggrecanase molecule followed by measurement of the degree of aggrecanase inhibition, for instance by detection and measurement of aggrecan fragments produced by cleavage at an aggrecanase susceptible site. Inhibitors may be proteins, antibodies or small molecules.

VIII. Disease Treatment and Diagnosis

Inhibitors of aggrecanase activity may be used in the treatment of diseases described below. Inhibitors can also be used in the assays and methods of detection described. Various diseases that are contemplated as being treatable by using inhibitors of aggrecanases of the invention include, but are not limited to, osteoarthritis, cancer, inflammatory joint disease, rheumatoid arthritis, septic arthritis, periodontal diseases, corneal ulceration, proteinuria, coronary thrombosis from atherosclerotic plaque rupture, aneurysmal aortic disease, inflammatory bowel disease, Crohn's disease, emphysema, acute respiratory distress syndrome, asthma, chronic obstructive pulmonary disease, Alzheimer's disease, brain and hematopoietic malignancies, osteoporosis, Parkinson's disease, migraine, depression, peripheral neuropathy, Huntington's disease, multiple sclerosis, ocular angiogenesis, macular degeneration, aortic aneurysm, myocardial infarction, autoimmune disorders, degenerative cartilage loss following traumatic joint injury, head trauma, dystrophic epidermolysis bullosa, spinal cord injury, acute and chronic neurodegenerative diseases, osteopenias, tempero mandibular joint disease, demyelating diseases of the nervous system, organ transplant toxicity and rejection, cachexia, allergy, tissue ulcerations, restenosis, and other diseases characterized by altered aggrecanase activity or altered aggrecanase level.

It is contemplated that inhibitors and antibodies of the invention that inhibit activity of aggrecanases and/or compounds that may lower expression of aggrecanases may be used in the treatment of any disease in a mammal that involves degradation of the extracellular matrix proteins, such as aggrecan, by aggrecanases and aggrecanase-related proteins.

IX. Administration

Another aspect of the invention provides pharmaceutical compositions containing a therapeutically effective amount of at least one of aggrecanase antibodies and inhibitors, in a pharmaceutically acceptable vehicle. Aggrecanase-mediated degradation of aggrecan in cartilage has been implicated in osteoarthritis and other inflammatory diseases. Therefore, these compositions of the invention may be used in the treatment of diseases characterized by the degradation of aggrecan and/or an up regulation of aggrecanase activity or level of aggrecanases.

The invention includes methods for treating patients suffering from conditions characterized by a degradation of aggrecan. These methods, according to the invention, entail administering to a patient needing such treatment, an effective amount of a composition comprising an aggrecanase antibody or inhibitor which inhibits the proteolytic activity of an aggrecanase enzyme.

Antibodies and inhibitors of the present invention are useful to diagnose or treat various medical disorders in humans or animals. In one embodiment, the antibodies of the invention can be used to inhibit or reduce one or more activities associated with an aggrecanase protein, relative to an aggrecanase protein not bound by the same antibody. In one embodiment, antibodies and inhibitors of the invention can inhibit or reduce one or more of the activities of an aggrecanase molecule relative to the aggrecanase that is not bound by an antibody. In certain embodiments, an activity of an aggrecanase, when bound by one or more of the presently disclosed antibodies, is inhibited at least 50%, may be inhibited at least 60, 62, 64, 66, 68, 70, 72, 72, 76, 78, 80, 82, 84, 86, or 88%, may be inhibited at least 90, 91, 92, 93, or 94%, or may be inhibited at least 95% to 100% relative to the aggrecanase protein that is not bound by one or more of the presently disclosed antibodies.

Generally, compositions of the present are administered to a patient so that antibodies or their binding fragments are administered at a dose ranging from about 1 µg/kg to about 20 mg/kg, about 1 µg/kg to about 10 mg/kg, about 1 µg/kg to about 1 mg/kg, about 10 µg/kg to about 1 mg/kg, about 10 µg/kg to about 100 µg/kg, about 100 µg to about 1 mg/kg, or about 500 µg/kg to about 1 mg/kg. Antibodies are administered as a bolus dose, to maximize the interval of time that the antibodies can circulate in the patient's body following their administration to the patient. Continuous infusion may also be used after an initial bolus dose.

In another embodiment, the invention is directed to administration of inhibitors of aggrecanases, such as proteins and small molecules. The effective amount of an inhibitor is a dosage which is useful for reducing activity of aggrecanases to achieve a desired biological outcome. Generally, appropriate therapeutic dosages for administering an inhibitor may range, for example, from about 5 mg to about 100 mg, from about 15 mg to about 85 mg, from about 30 mg to about 70 mg, or from about 40 mg to about 60 mg. Inhibitors can be administered in one dose, or at intervals such as once daily, once weekly, or once monthly. Dosage schedules for administration of an aggrecanase inhibitor can be adjusted based on, for example, the affinity of the inhibitor for its aggrecanase target, the half-life of the inhibitor, and the severity of the patient's condition. Generally, inhibitors are administered as a bolus dose, to maximize their circulating levels. Continuous infusions may also be used after the bolus dose.

Toxicity and therapeutic efficacy of such compounds can be determined by standard pharmaceutical procedures in cell culture or experimental animal models, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies and inhibitors, which exhibit large therapeutic indices, are generally preferred.

The data obtained from cell culture assays and animal studies can be used in formulating a range of dosages for use in humans. The dosage of such compounds may lie within a range of circulating concentrations that exhibit an $ED_{50}$ with little or no toxicity. The dosage may vary within this range depending upon the dosage form employed and the route of administration utilized. For any antibody or inhibitor used according to the present invention, a therapeutically effective dose can be estimated initially from cell culture assays.

A dose may be formulated in animal models to achieve a circulating plasma concentration range that exhibits an $IC_{50}$ (i.e., the concentration of the test antibody which achieves a half-maximal inhibition of symptoms) as determined by cell culture assays. Levels in plasma may be measured, for example, by high performance liquid chromatography. The effects of any particular dosage can be monitored by suitable bioassays. Examples of suitable bioassays include DNA replication assays, transcription-based assays, GDF protein/receptor binding assays, creatine kinase assays, assays based on the differentiation of pre-adipocytes, assays based on glucose uptake in adipocytes, and immunological assays.

Therapeutic methods of the invention include administering the aggrecanase inhibitor compositions topically, systemically, or locally as an implant or a device. The dosage regimen will be determined by the attending physician based on various factors which modify the action of the aggrecanase protein, the site of pathology, the severity of disease, the patient's age, sex, and diet, the severity of any inflammation, time of administration and other clinical factors. Generally, systemic or injectable administration will be initiated at a dose which is minimally effective, and the dose will be increased over a preselected time course until a positive effect is observed. Subsequently, incremental increases in dosage will be made limiting to levels that produce a corresponding increase in effect, while taking into account any adverse affects that may appear. The addition of other known factors, to a final composition, may also affect the dosage.

Progress can be monitored by periodic assessment of disease progression. The progress can be monitored, for example, by X-rays, MRI or other imaging modalities, synovial fluid analysis, patient response, and/or clinical examination.

X. Assays and Methods of Detection

The inhibitors and antibodies of the invention can be used in assays and methods of detection to determine the presence or absence of, or quantify aggrecanase in a sample. The inhibitors and antibodies of the present invention may be used to detect aggrecanase proteins, in vivo or in vitro. By correlating the presence or level of these proteins with a disease, one of skill in the art can diagnose the associated disease or determine its severity. Diseases that may be diagnosed by the presently disclosed inhibitors and antibodies are set forth above.

Detection methods for use with antibodies are well known in the art and include ELISA, radioimmunoassay, immunoblot, western blot, immunofluorescence, immuno-precipitation, and other comparable techniques. The antibodies may further be provided in a diagnostic kit that incorporates one or more of these techniques to detect a protein (e.g., an aggrecanase protein). Such a kit may contain other components, packaging, instructions, or other material to aid the detection of an aggrecanase protein, and instructions regarding use of the kit. When protein inhibitors are used in such diagnostic assays, protein-protein interaction assays can be employed.

Where antibodies and inhibitors are intended for diagnostic purposes, it may be desirable to modify them, for example, with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. Other suitable binding partners include biotin and avidin or streptavidin, IgG and protein A, and the numerous receptor-ligand couples known in the art.

EXAMPLES

Example 1

Isolation of DNA

Potential novel aggrecanase family members were identified using a database screening approach. Aggrecanase-1 (*Science* 284:1664–1666 (1999)) has at least six domains: signal, propeptide, catalytic domain, disintegrin, tsp (thrombospondin), and c-terminal. The catalytic domain contains a zinc binding signature region, TAAHELGHVKF (SEQ. ID NO: 6) and a "MET turn" which are responsible for protease activity. Substitutions within the zinc binding region in the number of the positions still allow protease activity, but the histidine (H) and glutamic acid (E) residues must be present. The thrombospondin domain of Aggrecanase-1 is also a critical domain for substrate recognition and cleavage. It is these two domains that determine our classification of a novel aggrecanase family member. The coding region of the aggrecanase-1 DNA sequence was used to query against the GeneBank ESTs focusing on human ESTs using TBLASTN. The resulting sequences were the starting point in an effort to identify a sequence for potential family members. A particular nucleotide sequence of the aggrecanase of the present invention, referred to as ADAMTS-18 or EST18, is depicted in FIGS. 1A and 1B (SEQ ID NO: 1).

The virtual EST18 sequence is set forth in FIGS. 5A and 5B (SEQ ID NO: 5). Based on the initial virtual sequence, a set of PCR primers was designed to amplify approximately 1200 base pairs spanning the pro and catalytic domain of EST18. This primer set was used to screen cDNA molecules from different types of tissue to identify tissue sources for aggrecanase molecules. Once the tissue sources were identified, two overlapping fragments of EST18 were amplified by PCR using the cDNA molecule and the amplified fragments were cloned into vectors for sequencing. Cloned sequences differed from the predicted sequence therefore, multiple replicas of each reaction were cloned and sequenced from three independent tissue sources. Based on sequence analysis of all the clones, a consensus open reading frame (ORF) of 3219 base pairs was determined (SEQ ID NO: 3). It is contemplated that this 3219 bp ORF frame does not represent the full-length gene, as further described below. The obtained sequence may be utilized to screen for and isolate the full length sequence Since the PCR conditions use to amplify the EST18 sequence promoted the introduction of errors, the 3219 bp ORF had to be constructed by amplifying multiple overlapping fragments, digesting them with specific restriction enzymes, followed by final ligation into the mammalian expression vector called pED.

Specifically, marathon-ready™ cDNA, brain, stomach, and thymus (Clontech, Palo Alto, Calif.) was used as a template in all PCR cloning reactions. All the PCR reactions were carried out in a Perkin-Elmer 9600 thermocycler (Wellesley, Mass.) utilizing the following cycling parameters: 94° C. for 30 sec, 5 cycles of 94° C. for 5 sec, 72° C. for 4 min, 5 cycles of 94° C. for 5 sec, 70° C. for 4 min, 30 cycles of 94° C. for 5 sec, 68° C. 4 min. Clontech's Advantage™ GC2 polymerase was used with a final concentration of 0.5 M GC-melt according to the manufacturer's recommendations (Clontech, Palo Alto, Calif.). The various primer sets used for amplifying each fragment of the putative full-length nucleotide for EST18 are depicted in FIG. 6A as the sequences set forth in SEQ ID NOs.: 9, 10, 11 and 12.

PCR products were digested with different enzymes, as shown in FIG. 6B, and then fractionated on a 1 or 1.5% agarose gel. DNA bands corresponding to the indicated digested sizes were recovered from the gel. Ligation reaction included equal molar ratios of the digested DNA fragments and the vector pED pre-digested with EcoRI and SalI. A particular cDNA construction using various amplification fragments was confirmed by DNA sequencing and is set forth in FIG. 3. (SEQ ID NO: 3)

The predicted amino acid sequence (SEQ ID NO: 4) of the aggrecanase of the present invention is set forth in FIG. 4. The cloned sequence appears to have 3 TSP sub-motifs. A TSP sub-motif is described as about 50 amino acids, it starts with signature WXXXXW and contains six cysteine residues. The third sub-motif in the sequence set forth in FIG. 4 consists of 41 amino acids, starts with WXXXXW and contains 4 cysteins. It is therefore contemplated that there are at least 10 additional amino acids, assuming that there are no additional TSP submotifs. The majority of aggrecanase of the invention is found in the three tissue sources: brain, stomach, and thymus.

An aggrecanase molecule according to the invention as set forth in FIG. 4 may be characterized as follows: The pre-pro region signal-sequence,

```
                                           (SEQ ID NO: 13)
LLQALQLCCLCCA- (SEQ ID NO: 14)
SVAAALASDSSSGASGLNDDYVFVTPVEVDSAGSYISHDILHNGRKKRSA
|(signal)      |(mature peptide) 5        18
``` contains three conserved cysteine residues and a furin site. The catalytic domain is characterized by a typical zinc binding motif. It contains 5 conserved cysteine residues upstream of the zinc binding sequence and three residues downstream of the zinc binding sequence. It also contains a conserved methionine "Met-turn" downstream of the zinc binding sequence. The Disintegrin-like domain contains eight conserved cysteine residues. The TSP module contains a heparin binding domain (WXXWXXW); a CD36-binding motif (CSRTCGG) (SEQ ID NO: 15); and six conserved cysteine residues. The cysteine-rich domain is characterized as containing ten conserved cysteines. The spacer domain is characterized by TSP-repeats wherein two and one half have been cloned. The N-terminal portion of the aggrecanases can be cloned using the sequences described. The TSP sub-motifs start with signature WXXXXW and contain six cysteins. The third motif in FIG. 4 has 4 cysteines.

The ADAMTS-18 nucleotide sequence was extended beyond the original sequence by 5' and 3' RACE. Thymus Marathon-Ready™ cDNA was purchased from Clontech (Palo Alto, Calif.) for use as a template in PCR cloning reactions. The antisense primer 5' TGGTATGATTCAC-GACGGAGAAGGG (SEQ ID NO: 16) was used in a first round 5' RACE reaction and the sense primer 5' CGGGT-CACCATCCTCACGTACTGTA (SEQ ID NO: 17) was used in the first round 3' RACE reaction, both in combination with the AP-1 end primers specific to the Marathon cDNAs. Clontech Advantage™ GC2 polymerase reagents (Clontech, Palo Alto, Calif.) were used according to the manufacturer's recommendations. All amplifications were carried out in a Perkin-Elmer 9600 thermocycler (Perkin Elmer, Wellesley, Mass.). Cycling parameters were 94° C. for 30 sec., 5 cycles of 94° C. for 5 sec., 72° C. for 4 mins., 5 cycles of 94° C. for 5 sec, 70° C. for 4 mins., 30 cycles of 94° C. for 5 sec, 68° C. for 4 min. The first round reactions were diluted 10 fold in TE, and 5 µl of the reaction mixture was used as a template for a second round of PCR. The antisense primer 5' AACCCTCGTGGTGGCAGACAAG (SEQ ID NO: 18) was used for second round 5' RACE and the sense primer 5' TCATTCCAGCTGGCGCCCGAAG-CAT (SEQ ID NO: 19) was used for second round 3' RACE utilizing the identical parameters as described for the first round, except with the AP-2 end primers specific to the Marathon cDNAs. Aliquots of each reaction were fractionated on a 1% agarose gel and then transfer to nitrocellulose for Southern analysis. The nitrocellulose membrane was prehybridized in Clontech ExpressHyb™ (Clontech, Palo Alto, Calif.) for 30 min. at 37° C. according to the manufacture recommendations. The membrane was then incubated with 1×106 CPM of α-ATP end-labeled oligos 5' CTGCCTCTGCTGTGCGTCGGTCGC (SEQ ID NO: 11) (5' RACE) or 5' GATAACTTTCCCAGAGCGAAGATGC (SEQ ID NO: 20) (3' RACE) at 37° C. for 1 hour. Unbound probe was removed by two washes at room temperature with 2×SSC/0.05% SDS followed by two additional washes at room temperature with 0.1×SSC/0.1% SDS. Duplicate agarose gels were run and the PCR products that corresponded with positive signals on the autoradiographs were excised out of the agarose gel and DNA was recovered from the gel matrix via BioRad's Prep-A-Gene DNA purification System. (Biorad, Hercules, Calif.). The recovered DNA was ligated into Stratagene's PCR-Script® Amp Cloning (Stratagene, La Jolla, Calif.) according to the manufacturer's instructions.

An aliquot of the ligation mixtures were transformed into Gibco Technologies Electromax DH10B cells according to the manufacturer's instructions. (Carlsbad, Calif.). Plasmid DNA was subsequently isolated from the resulting recombinant bacteria and the DNA was sequenced. In one experiment, the 5' RACE reactions yielded a total of 1065 bases, 156 bases of the 5' UTR, followed by a methionine that initiated the 909 base pairs of an open reading frame ending in the sequence that is described as the second round antisense primer (SEQ ID NO: 18). The 3' RACE reactions produced a total of 2368 bases, 1358 bases of coding sequence beginning with the sequence described as the second round sense primer (SEQ ID NO: 19), ending with a translational stop codon followed by 1007 base pairs of 3' UTR.

Example 2

EST18 Tissue Expression

A Clontech human multiple tissue expression array MTE™ (Clontech Catalog #: 7776-1) was probed with a 533 base pair α-$^{32}$P dCTP-labeled cDNA probe according to the manufacturer's guidelines. Probe labeling and hybridization were performed as follows: 5 µg of A18FS plasmid (described below) was digested with EcoRI enzyme in its optimal buffer according to the vendor's recommendations. The restriction digest was fractionated on a 1% agarose gel and a 533 base pair fragment encoding EST18 protein sequence including amino acid #1 (methionine) through amino acid #174 (asparagine) of SEQ ID NO: 2 was recovered from the agarose gel as outlined above. An α-$^{32}$P dCTP-labeled probe was made utilizing Amersham Pharmacia's Ready-To-Go kit (Catalog #: 27-9240-01, Pharmacia,). Briefly, 30 ng of heat-denatured DNA was incubated at 37° C. for 15 minutes with 50 µCi of α-$^{32}$P dCTP and one labeling bead. Following the incubation, the reaction mix was applied to a pre-equilibrated Pharmacia NICK column (Catalog #: 17-0855-02) to remove unincorporated α-$^{32}$P dCTP from the labeled probe. The desalted probe was assayed and 15×10$^6$ cpm was added to 5 ml of pre-warmed ExpressHyb. The hybridization mix was then transferred to a prehybridized MTE. Hybridization was allowed to proceed overnight with agitation at 65° C.

Probe detection: Following hybridization, the MTE was washed in a series of buffers accordingly to the manufacturer's guidelines. The MTE was then placed in a X-ray cassette with Kodak BioMax MS film (Kodak) and one intensifying screen. The cassette was then stored at −70° C. Individual films were developed after either 20 or 76 hours. The results after either exposure were identical. Expression was restricted to left and right cerebellum, corpus callosum and placenta.

Example 3

Expression of a Truncated Form the Aggrecanase Protein

A truncated form of protein encoded by the EST18 nucleotide sequence was expressed as a fusion protein. One such truncated protein, A18FS, refers to the first 650 amino acids, from amino acid #1 (methionine) to amino acid #650 (phenylalanine) encoded by the EST18 nucleotide sequence. The expression construct was generated in two steps. First, the 5' end of EST18 nucleotide sequence was modified to include the additional coding nucleotide sequence identified by 5' RACE. Second, the construct had an open reading frame, such that it ended at the codon for phenylalanine. A Streptavidin-Tag sequence was added to aid in purification of the recombinant protein.

Modification of the 5' end: The six synthetic oligonucleotides listed below were designed to anneal together to form a DNA sequence flanked by an EcoRI site on the 5' end and a SacII site on the 3' end. The cloned EST18 sequence was digested with EcoRI and SacII enzymes. The digested vector was fractionated on a 1% agarose gel and the recovered DNA was ligated with the synthetic oligonucleotides. The oligonucleotides are depicted below:

```
5' AATTCCCACCATGGAGTGCGCCCTCCTGCTCGCGTGTGCCT 3';        (SEQ ID NO: 21)

5' CCCACCATGGAGTGCGCCCTCCTGCTCGCGTGTGCCTTCCCGGCTGCG 3'; (SEQ ID NO: 22)

5' TCCCGGCTGCGGGTTCGGGCCCGCCGAGGGGCCTGGCGGGACTGGGGCGC   (SEQ ID NO: 23)

GTGGCCAAG 3';
```

```
5' GGTTCGGGCCCGCCGAGGGGCCTGGCGGGACTGGGGCGCGTGGCCAAGGC    (SEQ ID NO: 24)

GCTCCAGCT 3';

5' GCGCTCCAGCTGTGCTGCCTCTGCTGTGCGTCGGTCGCCGC 3';         (SEQ ID NO: 25)
and

5' GTGCTGCCTCTGCTGTGCGTCGGTCGCC 3'.                       (SEQ ID NO: 26)
```

An aliquot of the ligation mix was transformed into Gibco Life Technologies ElectroMax DH10B cells and the sequence of the recombinant plasmid was confirmed by sequencing.

A18FS truncation and Streptavidin-Tagging: A18FS was PCR amplified using the following primer pair Forward primer 5' CTCGCGGTTGAGGACAAACTCT-TCG 3' (SEQ ID NO: 27) and Reverse primer

```
                                                         (SEQ ID NO: 28)
5'CCCTTGCAATGAAAATAGCTTGGATTTTGGAAGCGCTTGGAGCCACCC

GCAGTTCGAAAAATAAGGCGGCCGCCGCAAA 3'
``` and the EST18 nucleotide sequence as template. The forward primer contained the unique restriction site BglII and the reverse primer contained the unique restriction sites NotI to allow for directional cloning into the pre-digested expression vector. The reverse primer also included the resulting protein sequence GSAWSHPQFEK (SEQ ID NO: 29) that functions as an epitope tag.

PCR amplification was preformed in a 50 µl volume reaction containing: 5 µl 10× PCR reaction buffer; 1 µl dNTP mix up to the final concentration of 0.2 mM; 10 pmoles of the forward primer (SEQ ID NO: 27; 10 pmoles of the reverse primer ((SEQ ID NO: 28); 1 ng of the EST18 full-length nucleotide template as depicted in SEQ ID NO: 1; 2.5 units of the Stratagene Pfu Turbo Hotstart polymerase (Catalog # 600320); and distilled $H_2O$ up to 50 µl. Amplification reaction conditions were 94° C. for 2 mins; 94° C. for 15 secs; amplification at 70° C. for 3 mins for a total of 22 cycles; and extension at 72° C. for 5 mins followed by chilling at 4° C. The nucleotide sequence encoding the truncated form of aggrecanase protein including a Streptavidin tag is disclosed in SEQ ID NO: 7.

Example 4

Expression of Aggrecanase in CHO cells

In order to produce murine, human or other mammalian aggrecanase-related proteins, the DNA encoding an aggrecanase protein is cloned into an appropriate expression vector and introduced into mammalian cells or other preferred eukaryotic or prokaryotic hosts, including insect host cell culture systems, using conventional genetic engineering techniques. Expression systems for biologically active recombinant human aggrecanase are contemplated to include stably transformed mammalian, insect, yeast or bacterial cells.

The mammalian expression vector pMT2 CXM is a derivative of p91023(b) (Wong et al., *Science* 228:810–815 (1985)) and differs from the latter in that it contains an ampicillin resistance gene in place of a tetracycline resistance gene and further contains a XhoI site for insertion of cDNA molecules into the vector. The functional elements of pMT2 CXM have been described (Kaufman, *Proc. Natl. Acad. Sci. USA* 82:689–693 (1985)) and include adenovirus VA genes, the SV40 origin of replication including the 72 bp enhancer, the adenovirus major late promoter including a 5' splice site and majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM was obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 which are then resistant to ampicillin. Plasmid pMT2 DNA can be prepared by conventional methods. pMT2 CXM is then constructed using loopout/in mutagenesis technique (Morinaga, et al., *Biotechnology* 84: 636 (1984)). This removes bases 1075 to 1145 relative to the Hind III site near the SV40 origin of replication and enhancer sequences of pMT2. In addition it inserts the following sequence: 5' CATGGGCAGCTCGAG 3' (SEQ. ID NO: 30 ) at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 was derived from pMT2 which is derived from pMT2-VWF. As described above, EcoRI digestion excises the cDNA insert present in pMT-VWF, yielding pMT2 in linear form which subsequently can be ligated and used to transform *E. Coli* HB 101 or DH-5 resulting in ampicillin resistance. Plasmid pMT2 DNA can be prepared by conventional methods.

pMT21 was derived from pMT2 through the following two modifications. First, 76 bp of the 5' untranslated region of the DHFR cDNA, including a stretch of 19 G residues from G/C tailing for cDNA cloning, is deleted. In this process, a XhoI site was inserted to obtain the following sequence immediately upstream from DHFR:

```
                                                        (SEQ. ID NO: 31)
                         5' CTGCAGGCGAGCCTGAATTCCTCGAGCCATCATG3'

PstI        Eco RI XhoI
```

Second, a unique ClaI site was introduced by digestion with EcoRV and XbaI, treatment with Klenow fragment of DNA polymerase I, and ligation to a ClaI linker (CATC-GATG). This deletes a 250 bp segment from the adenovirus associated RNA (VAI) region but does not interfere with VAI RNA gene expression or function. pMT21 was digested with EcoRI and XhoI, and used to derive the vector pEMC2B1.

A portion of the EMCV leader was obtained from pMT2-ECAT1 (S. K. Jung, et a., *J. Virol* 63:1651–1660 (1989)) by digestion with Eco RI and PstI, resulting in a 2752 bp fragment. This fragment was digested with TaqI yielding an Eco RI-TaqI fragment of 508 bp which was isolated by electrophoresis on low melting agarose gel. A 68 bp adapter and its complementary strand were synthesized with a 5' TaqI protruding end and a 3' XhoI protruding end which has the following sequence:

```
5 CGAGGTTAAAAAACGTCTAGGCCCCCCGAACCACGGGGACGTGGTTTTCCTTT  (SEQ. ID NO: 32)
  TaqI

GAAAAACACGATTGC3'
          XhoI
```

This sequence matches the EMC virus leader sequence from nucleotide 763 to 827. It also changes the ATG at position 10 within the EMC virus leader to an ATT and was followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

In one example, the aggrecanase nucleotide sequence of the present invention set forth in SEQ ID NO: 1 may be cloned into the expression vector pED6 (Kaufman et al., *Nucleic Acid Res* 19:44885–4490 (1991)). COS and CHO DUKX B11 cells were transiently transfected with the aggrecanase sequence of the invention (+/− co-transfection of PACE on a separate pED6 plasmid) by lipofection (LF2000, Invitrogen, Carlsbad, Calif.)). Duplicate transfections were performed for each gene of interest: (a) one for harvesting conditioned media for activity assay and (b) one for $^{35}S$ methionine/cysteine metabolic labeling.

On day one, media was changed to DME(COS)or alpha (CHO) media+1% heat-inactivated fetal calf serum +/− 100 μg/ml heparin for one set of transfections (a) to be harvested for activity assay. After 48 h (day 4), conditioned media was harvested for activity assays.

On day 3, the medium for cells of the duplicate set of transfections (b) was changed to MEM (methionine-free/cysteine free) media+1% heat-inactivated fetal calf serum+ 100 μg/ml heparin+100 μCi/ml 35S-methioine/cysteine (Redivue™ Pro mix, Amersham, Piscataway, N.J.). Following a 6 h incubation at 37° C., conditioned media was harvested and run on SDS-PAGE gels under reducing conditions. Proteins were visualized by autoradiography.

In another example, the aggrecanase nucleotide sequence of the present invention set forth in SEQ ID NO: 1 may be cloned into expression vector pHTop, a derivative of pED (Kaufman et al., 1991 NAR 19:4485–4490) in which the majority of the adenomajor late promoter was replaced by six repeats of the tet operator (described in Gossen et al., 1992, *Proc. Natl. Acad. Sci. USA* 89:5547–5551). This vector contains the dihydrofolate reductase gene and when introduced in the cell line CHO/A2 (see, description below) functions very efficiently and high expressors can be selected by isolating cells surviving in high methotrexate concentrations.

Similarly, the recombinant aggrecanase protein set forth in SEQ ID NO: 8 and as expressed using a method described can be cloned into a pHTop vector.

Establishment of CHO stable cell lines: The CHO/A2 cell line was derived from CHO DUKX B11 (Urlaub and Chasin, 1980, *Proc. Natl. Acad. Sci. USA* 77:4216–4220) by stably integrating a transcriptional activator (tTA), a fusion protein between the Tet repressor and the herpes virus VP16 transcriptional domain (Gossen et al., 1992, *Proc. Natl. Acad. Sci. USA* 89: 5547–5551). A CHO cell line expressing extracellular ADAMTS-18 was established by transfecting (lipofection) pHTopADAMTS8-Streptavidin tagged DNA into CHO/A2 cells and selecting clones in 0.02, 0.05 and 0.01 μM methotrexate.

Screening of CHO stable cell lines: Multiple clones were screened by Western Blot using a streptavidin HRP antibody. The best clone was determined by virtue of its high expression and was one which resulted from 0.02 μM MTX selection and was chosen to be scaled up for roller bottle conditioned media production (4 Liters). The cell line was sent for large scale production.

Example 5

Biological Activity of Expressed Aggrecanase

To measure the biological activity of the expressed aggrecanase-related proteins, for example, proteins obtained in Example 4 above, the proteins are recovered from the cell culture and purified by isolating the aggrecanase-related proteins from other proteinaceous materials with which they are co-produced as well as from other contaminants. Purification is carried out using standard techniques known to those skilled in the art. The isolated protein may be assayed in accordance with the following assays:

Assays specifically to determine if the protein is an enzyme capable of cleaving aggrecan at the aggrecanase cleavage site:

1: Fluorescent peptide assay: Expressed protein is incubated with a synthetic peptide which encompasses amino acids at the aggrecanase cleavage site of aggrecan. Either the N-terminus or the C-terminus of the synthetic peptide is labeled with a flourophore and the other terminus includes a quencher. Cleavage of the peptide separates the flourophore and quencher and elicits flourescence. From this assay it is determined that the expressed aggrecanase protein can cleave aggrecan at the aggrecanase site, and relative fluorescence is a determination the relative activity of the expressed protein.

2. Neoepitope western: Expressed aggrecanase protein is incubated with intact aggrecan. After several biochemical manipulations of the resulting sample (dialysis, chondroitinase treatment, lyophilization and reconstitution) the sample is run on an SDS PAGE gel. The gel is incubated with an antibody that is specific to a site on aggrecan which is only exposed after aggrecanase cleavage. The gel is transferred onto nitrocellulose paper and developed using a secondary antibody (called a western assay) which subsequently results in a banding pattern indicative of products with a molecular weight consistent with aggrecanase generated cleavage products of aggrecan. This assay results in the finding that the expressed aggrecanase protein cleaved native aggrecan at the aggrecanase cleavage site, and also gives the molecular weight of the cleavage products. Relative density of the bands can give an indication of relative aggrecanase activity.

Assay to determine if an expressed protein can cleave aggrecan anywhere in the protein (not specific to the aggrecanase site):

3. Aggrecan ELISA: Expressed protein is incubated with intact aggrecan which had been previously adhered to plastic wells. The wells are washed and then incubated with an antibody that detects aggrecan. The wells are developed with a secondary antibody. If the original amount of aggrecan remains in the wells, the antibody staining is dense. Whereas, if aggrecan was digested by aggrecanase activity of the expressed aggrecanase protein, the aggrecan comes off the plate and the subsequent staining of the aggrecan coated wells by the antibody is reduced. This assay tells whether an expressed protein is capable of cleaving aggrecan (anywhere in the protein, not only at the aggrecanase site) and can further determine relative aggrecan cleavage.

Protein analysis of the isolated proteins is conducted using standard techniques such as SDS-PAGE acrylamide (Laemmli, *Nature* 227:680 (1970)) stained with silver (Oakley, et al., *Anal Biochem.* 105:361 (1980)) and by immunoblot (Towbin, et al., *Proc. Natl. Acad. Sci. USA* 76:4350 (1979)). Using the above described assays, expressed aggrecanase-related proteins are evaluated for their activity and useful aggrecanase-related molecules are identified.

Example 6

Aggrecanase Activity of ADAMTS-18

Figure 10:
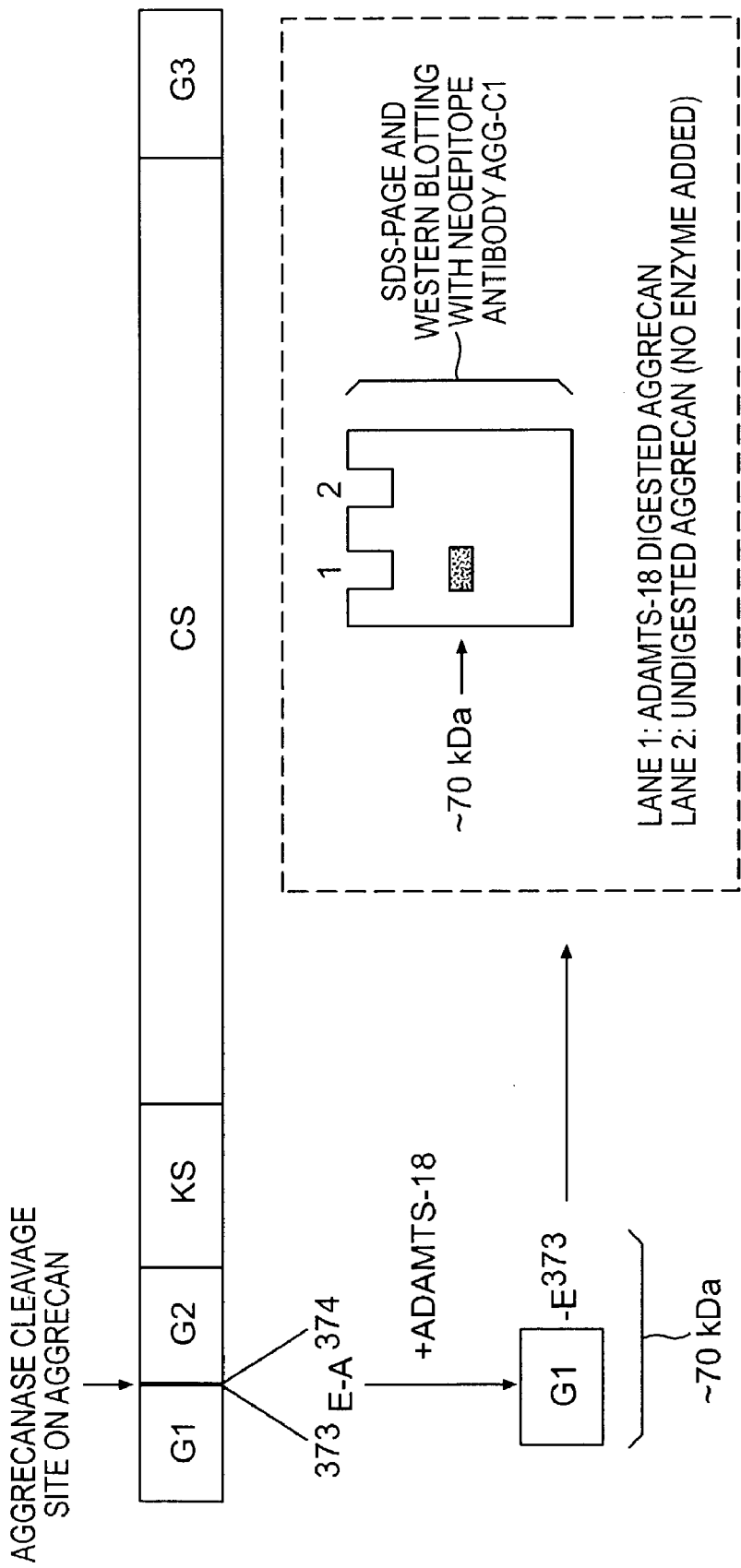
FIG. 10 shows a schematic representation of an assay for detecting aggrecanase activity.

Bovine articular cartilage was incubated with isolated ADAMTS-18 for 16 h at 37° C. in 50 mM Tris, pH 7.3, containing 100 mM NaCl and 5 mM $CaCl_2$. Digestion products were deglycosylated by incubation for 2 h at 37° C. in the presence of chondroitinase ABC (Seikagaku America, Falmouth, Mass.; 1 mU/μg aggrecan), keratinase (Seikagaku, 1 mU/μg aggrecan) and keratanase II (Seikagaku; 0.02 mU/μg aggrecan). After separation by SDS-PAGE, digestion products were transferred to nitrocellulose and detected by Western immunoblotting with the neoepitope (monoclonal) antibody AGG-C1 which recognizes the C-terminal neoepitope sequence-NITEGE$^{373}$ (SEQ ID NO: 33) generated by cleavage of the aggrecanase-susceptible $E^{373}$-$A^{374}$ peptide bond located between the G1 and G2 domains of aggrecan. (FIG. 10).

Example 7

Preparation of Antibodies

An antibody against a novel aggrecanase molecule is prepared. To develop an antibody capable of inhibiting aggrecanase activity, a group of mice are immunized every two weeks with a novel aggrecanase protein mixed in Freunds complete adjuvant for the first two immunizations, and incomplete Freunds adjuvant thereafter. Throughout the immunization period, blood is sampled and tested for the presence of circulating antibodies. At week 9, an animal with circulating antibodies is selected, immunized for three consecutive days, and sacrificed. The spleen is removed and homogenized into cells. The spleen cells are fused to a myeloma fusion partner (cell line P3-x63-Ag8.653-]) using 50% PEG 1500 by an established procedure (Oi & Herzenberg, *Selected Methods in Cellular Immunology*, W. J. Freeman Co., San Francisco, Calif., at 351 (1980)). The fused cells are plated into 96-well microtiter plates at a density of $2×10^5$ cells/well. After 24 hours, the cells are subjected to HAT selection (Littlefield, *Science,* 145: 709 (1964)) effectively killing any unfused and unproductively fused myeloma cells.

Successfully fused hybridoma cells secreting anti-aggrecanase antibodies are identified by solid and solution phase ELISAs. Novel aggrecanase protein is prepared from CHO cells as described above and coated on polystyrene (for solid phase assays) or biotinylated plates (for a solution based assay). Neutralizing assays are also employed where aggrecan is coated on a polystyrene plate and biotin aggrecanase activity is inhibited by the addition of hybridoma supernatant. Results identify hybridomas expressing aggrecanase antibodies. These positive clones are cultured and expanded for further study. These cultures remain stable when expanded and cell lines are cloned by limiting dilution techniques and subsequently cryopreserved.

From these cell cultures, a panel of antibodies is developed that specifically recognize aggrecanase proteins. Isotype of the antibodies is determined using a mouse immunoglobulin isotyping kit (Zymed™ Laboratories, Inc., San Francisco, Calif.).

Example 8

Method of Detecting Level of Aggrecanase

An anti-aggrecanase antibody prepared according to the invention as described, can be used to detect level of aggrecanases in a sample. An antibody can be used in an ELISA, for example, to identify the presence or absence, or quantify the amount of, an aggrecanase in a sample, to which the antibody binds. The antibody can be labeled with a fluorescent tag. In general, the level of aggrecanase in a sample can be determined using any of the assays disclosed.

Example 9

Method of Treating a Patient

Antibodies developed according to methods disclosed can be administered to patients suffering from a disease or disorder related to the loss of aggrecan, or an increase in aggrecanase activity. Patients may need to take a composition of the invention as a once time administration or at intervals, such as once daily, until the symptoms and signs of their disease or disorder improve. For example, subsequent to the administration of a composition of the invention to a patient, loss of aggrecan decreases or ceases and degradation of articular cartilage decreases or ceases. It is expected that symptoms of osteoarthritis would be reduced or eliminated. This would show that compositions of the invention would be useful for the treatment of diseases or disorders related to the loss of aggrecan, or an increase in the levels and/or activity of aggrecanases. Antibodies can also be used with patients that are susceptible to osteoarthritis, such as those who have a family history or markers of the disease, but are asymptomatic. The following results would be expected for treatment of patients.

| Patient's Condition | Route of Administration | Dosage | Frequency | Predicted Results |
|---|---|---|---|---|
| Osteoarthritis | Subcutaneous | 500 µg/kg | Daily | Decrease in symptoms |
| " | " | 1 mg/kg | Weekly | Decrease in symptoms |
| " | Intramuscular | 500 µg/kg | Daily | Decrease in symptoms |
| " | " | 1 mg/kg | Weekly | Decrease in symptoms |
| " | Intravenous | 500 µg/kg | Daily | Decrease in symptoms |
| " | " | 1 mg/kg | Weekly | Decrease in symptoms |
| Family History of Osteoarthritis | Subcutaneous | 500 µg/kg | Daily | Prevention of condition |
| Family History of Osteoarthritis | Intramuscular | 500 µg/kg | Daily | Prevention of condition |
| Family History of Osteoarthritis | Intravenous | 500 µg/kg | Daily | Prevention of condition |

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto. All of the documents cited in this application are incorporated by reference in their entirety. Additionally, all sequences cited in databases and all references disclosed are incorporated by reference in their entirety.

What is claimed is:

1. An isolated aggrecanase protein comprising amino acids 1–650 SEQ ID NO: 2.

2. An isolated aggrecanase protein produced by the steps of
   a) culturing a cell transformed with a DNA molecule encoding an aggrecanase protein comprising amino acids 1–650 of SEQ ID NO:2; and
   b) recovering and purifying the aggrecanase protein from said culture.

3. The aggrecanase protein of claim 1, wherein the aggrecanase protein comprises amino acids 1–1221 of SEQ ID NO: 2.

4. A fusion protein comprising the aggrecanase protein of claim 1 fused to a tag.

* * * * *

UNITED STATES PATENT AND TRADEMARK OFFICE
CERTIFICATE OF CORRECTION

PATENT NO. : 7,078,217 B2 Page 1 of 1
APPLICATION NO. : 10/354983
DATED : July 18, 2006
INVENTOR(S) : Corcoran et al.

It is certified that error appears in the above-identified patent and that said Letters Patent is hereby corrected as shown below:

Column 75, Line 59
Claim 1, line 60, after "1-650" insert -- of --.

Signed and Sealed this

Twelfth Day of September, 2006

JON W. DUDAS
*Director of the United States Patent and Trademark Office*

SEQUENCE LISTING

<160> NUMBER OF SEQ ID NOS: 32

<210> SEQ ID NO 1
<211> LENGTH: 3663
<212> TYPE: DNA
<213> ORGANISM: Homo sapiens

<400> SEQUENCE: 1

```
atggagtgcg ccctcctgct cgcgtgtgcc ttcccggctg cgggttcggg cccgccgagg      60
ggcctggcgg gactggggcg cgtggccaag gcgctccagc tgtgctgcct ctgctgtgcg     120
tcggtcgccg cggccttagc cagtgacagc agcagcggcg ccagcggatt aaatgatgat     180
tacgtctttg tcacgccagt agaagtagac tcagccgggt catatatttc acacgacatt     240
ttgcacaacg gcaggaaaaa gcgatcggcg cagaatgcca gaagctccct gcactaccga     300 tttttcagcat ttggacagga actgcactta gaacttaagc cctcggcgat tttgagcagt     360
cactttattg tccaggtact tggaaaagat ggtgcttcag agactcagaa acccgaggtg     420
cagcaatgct tctatcaggg atttatcaga aatgacagct cctcctctgt cgctgtgtct     480
acgtgtgctg gcttgtcagg tttaataagg acacgaaaaa atgaattcct catctcgcca     540
ttacctcagc ttctggccca ggaacacaac cacagctccc ctgcgggtca ccatcctcac     600
gtactgtaca aaggacagc agaggagaag atccagcggt accgtggcta ccccggctct     660
ggccggaatt atcctggtta ctccccaagt cacattcccc atgcatctca gagtcgagag     720
acagagtatc accatcgaag gttgcaaaag cagcattttt gtggacgacg caagaaatat     780
gctcccaagc ctcccacaga ggacacctat ctaaggtttg atgaatatgg gagctctggg     840
cgacccagaa gatcagctgg aaaatcacaa aagggcctca atgtggaaac cctcgtggtg     900
gcagacaaga aaatggtgga aaagcatggc aagggaaatg tcaccacata cattctcaca    960
gtaatgaaca tggtttctgg cctatttaaa gatgggacta ttggaagtga cataaacgtg   1020
gttgtggtga gcctaattct tctggaacaa gaacctggag gattattgat caaccatcat   1080
gcagaccagt ctctgaatag tttttgtcaa tggcagtctg ccctcattgg aaagaatggc  1140
```

```
aagagacatg atcatgccat cttactaaca ggatttgata tttgttcttg gaagaatgaa   1200
ccatgtgaca ctctagggtt tgccccatc agtggaatgt gctctaagta ccgaagttgt    1260
accatcaatg aggacacagg acttggcctt gccttcacca tcgctcatga gtcagggcac   1320
aactttggta tgattcacga cggagaaggg aatccctgca gaaaggctga aggcaatatc   1380
atgtctccca cactgaccgg aaacaatgga gtgttttcat ggtcttcttg cagccgccag   1440
tatctcaaga aattcctcag cacacctcag gcggggtgtc tagtggatga gcccaagcaa   1500
gcaggacagt ataaatatcc ggacaaacta ccaggacaga tttatgatgc tgacacacag   1560
tgtaaatggc aatttggagc aaaagccaag ttatgcagcc ttggttttgt gaaggatatt   1620
tgcaaatcac tttggtgcca ccgagtaggc acaggtgtg agaccaagtt tatgcccgca    1680
gcagaaggga ccgtttgtgg cttgagtatg tggtgtcggc aaggccagtg cgtaaagttt   1740
ggggagctcg ggccccggcc catccacggc cagtggtccg cctggtcgaa gtggtcagaa   1800
tgttcccgga catgtggtgg aggagtcaag ttccaggaga cactgcaa taaccccaag     1860 cctcagtatg gtggcatatt ctgtccaggt tctagccgta tttatcagct gtgcaatatt   1920
aacccttgca atgaaaatag cttggatttt cgggcccaac agtgtgcaga atataacagc   1980
aaacctttcc gtggatggtt ctaccagtgg aaaccctata caaaagtgga agaggaagat   2040
cgatgcaaac tgtactgcaa ggctgagaac tttgaatttt ttttgcaat gtccggcaaa    2100 gtgaaagatg gaactccctg ctcccaaac agaaatgatg tttgtattga cggggtttgt    2160
gaactagtgg gatgtgatca tgaactaggc tctaaagcag tttcagatgc ttgtggcgtt   2220
tgcaaaggtg ataattcaac ttgcaagttt tataaaggcc tgtacctcaa ccagcataaa   2280
gcaaatgaat attatccggt ggtcatcatt ccagctggcg cccgaagcat cgaaatccag   2340
gagctgcagg tttcctccag ttacctcgca gttcgaagcc tcagtcaaaa gtattacctc   2400
accgggggct ggagcatcga ctggcctggg gagttcccct tcgctgggac cacgtttgaa   2460
taccagcgct ctttcaaccg cccggaacgt ctgtacgcgc cagggcccac aaatgagacg   2520
ctggtctttg aaattctgat gcaaggcaaa atccaggga tagcttggaa gtatgcactt    2580
cccaaggtca tgaatggaac tccaccagcc acaaaaagac ctgcctatac ctggagtatc   2640
gtgcagtcag agtgctccgt ctcctgtggt ggaggttaca taaatgtaaa ggccatttgc   2700
ttgcgagatc aaaatactca agtcaattcc tcattctgca gtgcaaaaac caagccagta   2760
actgagccca aaatctgcaa cgcttttctcc tgcccggctt actggatgcc aggtgaatgg   2820
agtacatgta gcaaggcctg tgctggaggc cagcagagcc gaaagatcca gtgtgtgcaa   2880
aagaagccct tccaaaagga ggaagcagtg ttgcattctc tctgtccagt gagcacaccc   2940
actcaggtcc aagcctgcaa cagccatgcc tgtcctccac aatggagcct tggaccctgg   3000
tctcagtgtt ccaagacctg tggacgaggg gtgaggaagc gtgaactcct ctgcaagggc   3060
tctgccgcag aaaccctccc cgagagccag tgtaccagtc tccccagacc tgagctgcag   3120
gagggctgtg tgcttggacg atgccccaag aacagccggc tacagtgggt cgcttcttcg   3180
tggagcgagt gttctgcaac ctgtggtttg ggtgtgagga agagggagat gaagtgcagc   3240
gagaagggct tccagggaaa gctgataact ttcccagagc gaagatgccg taatattaag   3300
aaaccaaatc tggacttgga agagacctgc aaccgacggg cttgcccagc ccatccagtg   3360
tacaacatgg tagctggatg gtattcattg ccgtggcagc agtgcacagt cacctgtggg   3420
ggaggggtcc agacccggtc agtccactgt gttcagcaag gccggccttc ctcaagttgt   3480
```

```
ctgctccatc agaaacctcc ggtgctacga gcctgtaata caaacttctg tccagctcct    3540
gaaaagagag aggatccatc ctgcgtagat ttcttcaact ggtgtcacct agttcctcag    3600
catggtgtct gcaaccacaa gttttacgga aaacaatgct gcaagtcatg cacaaggaag    3660
atc                                                                  3663
```

<210> SEQ ID NO 2
<211> LENGTH: 1221
<212> TYPE: PRT
<213> ORGANISM: Homo sapiens

<400> SEQUENCE: 2

```
Met Glu Cys Ala Leu Leu Ala Cys Ala Phe Pro Ala Ala Gly Ser
 1               5                  10                  15

Gly Pro Pro Arg Gly Leu Ala Gly Leu Gly Arg Val Ala Lys Ala Leu
                20                  25                  30

Gln Leu Cys Cys Leu Cys Cys Ala Ser Val Ala Ala Leu Ala Ser
             35                  40                  45

Asp Ser Ser Gly Ala Ser Gly Leu Asn Asp Asp Tyr Val Phe Val
         50                  55                  60

Thr Pro Val Glu Val Asp Ser Ala Gly Ser Tyr Ile Ser His Asp Ile
 65                  70                  75                  80

Leu His Asn Gly Arg Lys Lys Arg Ser Ala Gln Asn Ala Arg Ser Ser
                 85                  90                  95

Leu His Tyr Arg Phe Ser Ala Phe Gly Gln Glu Leu His Leu Glu Leu
                100                 105                 110

Lys Pro Ser Ala Ile Leu Ser Ser His Phe Ile Val Gln Val Leu Gly
             115                 120                 125

Lys Asp Gly Ala Ser Glu Thr Gln Lys Pro Glu Val Gln Gln Cys Phe
         130                 135                 140

Tyr Gln Gly Phe Ile Arg Asn Asp Ser Ser Ser Val Ala Val Ser
145                 150                 155                 160

Thr Cys Ala Gly Leu Ser Gly Leu Ile Arg Thr Arg Lys Asn Glu Phe
                165                 170                 175

Leu Ile Ser Pro Leu Pro Gln Leu Leu Ala Gln Glu His Asn His Ser
            180                 185                 190

Ser Pro Ala Gly His His Pro His Val Leu Tyr Lys Arg Thr Ala Glu
        195                 200                 205

Glu Lys Ile Gln Arg Tyr Arg Gly Tyr Pro Gly Ser Gly Arg Asn Tyr
    210                 215                 220

Pro Gly Tyr Ser Pro Ser His Ile Pro His Ala Ser Gln Ser Arg Glu
225                 230                 235                 240

Thr Glu Tyr His His Arg Arg Leu Gln Lys Gln His Phe Cys Gly Arg
                245                 250                 255

Arg Lys Lys Tyr Ala Pro Lys Pro Pro Thr Glu Asp Thr Tyr Leu Arg
            260                 265                 270

Phe Asp Glu Tyr Gly Ser Ser Gly Arg Pro Arg Arg Ser Ala Gly Lys
        275                 280                 285

Ser Gln Lys Gly Leu Asn Val Glu Thr Leu Val Val Ala Asp Lys Lys
    290                 295                 300

Met Val Glu Lys His Gly Lys Gly Asn Val Thr Thr Tyr Ile Leu Thr
305                 310                 315                 320

Val Met Asn Met Val Ser Gly Leu Phe Lys Asp Gly Thr Ile Gly Ser
                325                 330                 335
```

```
                                    -continued

Asp Ile Asn Val Val Val Ser Leu Ile Leu Glu Gln Glu Pro
            340                 345             350

Gly Gly Leu Leu Ile Asn His His Ala Asp Gln Ser Leu Asn Ser Phe
        355                 360             365

Cys Gln Trp Gln Ser Ala Leu Ile Gly Lys Asn Gly Lys Arg His Asp
    370                 375                 380

His Ala Ile Leu Leu Thr Gly Phe Asp Ile Cys Ser Trp Lys Asn Glu
385                 390                 395                 400

Pro Cys Asp Thr Leu Gly Phe Ala Pro Ile Ser Gly Met Cys Ser Lys
                405                 410                 415

Tyr Arg Ser Cys Thr Ile Asn Glu Asp Thr Gly Leu Gly Leu Ala Phe
            420                 425                 430

Thr Ile Ala His Glu Ser Gly His Asn Phe Gly Met Ile His Asp Gly
            435                 440                 445

Glu Gly Asn Pro Cys Arg Lys Ala Glu Gly Asn Ile Met Ser Pro Thr
450                 455                 460

Leu Thr Gly Asn Asn Gly Val Phe Ser Trp Ser Ser Cys Ser Arg Gln
465                 470                 475                 480

Tyr Leu Lys Lys Phe Leu Ser Thr Pro Gln Ala Gly Cys Leu Val Asp
                485                 490                 495

Glu Pro Lys Gln Ala Gly Gln Tyr Lys Tyr Pro Asp Lys Leu Pro Gly
            500                 505                 510

Gln Ile Tyr Asp Ala Asp Thr Gln Cys Lys Trp Gln Phe Gly Ala Lys
        515                 520                 525

Ala Lys Leu Cys Ser Leu Gly Phe Val Lys Asp Ile Cys Lys Ser Leu
    530                 535                 540

Trp Cys His Arg Val Gly His Arg Cys Glu Thr Lys Phe Met Pro Ala
545                 550                 555                 560

Ala Glu Gly Thr Val Cys Gly Leu Ser Met Trp Cys Arg Gln Gly Gln
                565                 570                 575

Cys Val Lys Phe Gly Glu Leu Gly Pro Arg Pro Ile His Gly Gln Trp
            580                 585                 590

Ser Ala Trp Ser Lys Trp Ser Glu Cys Ser Arg Thr Cys Gly Gly Gly
        595                 600                 605

Val Lys Phe Gln Glu Arg His Cys Asn Asn Pro Lys Pro Gln Tyr Gly
    610                 615                 620

Gly Ile Phe Cys Pro Gly Ser Ser Arg Ile Tyr Gln Leu Cys Asn Ile
625                 630                 635                 640

Asn Pro Cys Asn Glu Asn Ser Leu Asp Phe Arg Ala Gln Gln Cys Ala
                645                 650                 655

Glu Tyr Asn Ser Lys Pro Phe Arg Gly Trp Phe Tyr Gln Trp Lys Pro
            660                 665                 670

Tyr Thr Lys Val Glu Glu Asp Arg Cys Lys Leu Tyr Cys Lys Ala
        675                 680                 685

Glu Asn Phe Glu Phe Phe Ala Met Ser Gly Lys Val Lys Asp Gly
    690                 695                 700

Thr Pro Cys Ser Pro Asn Arg Asn Asp Val Cys Ile Asp Gly Val Cys
705                 710                 715                 720

Glu Leu Val Gly Cys Asp His Glu Leu Gly Ser Lys Ala Val Ser Asp
                725                 730                 735

Ala Cys Gly Val Cys Lys Gly Asp Asn Ser Thr Cys Lys Phe Tyr Lys
            740                 745                 750

Gly Leu Tyr Leu Asn Gln His Lys Ala Asn Glu Tyr Tyr Pro Val Val
```

-continued

```
                755                 760                 765
Ile Ile Pro Ala Gly Ala Arg Ser Ile Glu Ile Gln Glu Leu Gln Val
770                 775                 780

Ser Ser Ser Tyr Leu Ala Val Arg Ser Leu Ser Gln Lys Tyr Tyr Leu
785                 790                 795                 800

Thr Gly Gly Trp Ser Ile Asp Trp Pro Gly Glu Phe Pro Phe Ala Gly
                805                 810                 815

Thr Thr Phe Glu Tyr Gln Arg Ser Phe Asn Arg Pro Glu Arg Leu Tyr
                820                 825                 830

Ala Pro Gly Pro Thr Asn Glu Thr Leu Val Phe Glu Ile Leu Met Gln
                835                 840                 845

Gly Lys Asn Pro Gly Ile Ala Trp Lys Tyr Ala Leu Pro Lys Val Met
850                 855                 860

Asn Gly Thr Pro Pro Ala Thr Lys Arg Pro Ala Tyr Thr Trp Ser Ile
865                 870                 875                 880

Val Gln Ser Glu Cys Ser Val Ser Cys Gly Gly Gly Tyr Ile Asn Val
                885                 890                 895

Lys Ala Ile Cys Leu Arg Asp Gln Asn Thr Gln Val Asn Ser Ser Phe
                900                 905                 910

Cys Ser Ala Lys Thr Lys Pro Val Thr Glu Pro Lys Ile Cys Asn Ala
                915                 920                 925

Phe Ser Cys Pro Ala Tyr Trp Met Pro Gly Glu Trp Ser Thr Cys Ser
                930                 935                 940

Lys Ala Cys Ala Gly Gly Gln Gln Ser Arg Lys Ile Gln Cys Val Gln
945                 950                 955                 960

Lys Lys Pro Phe Gln Lys Glu Glu Ala Val Leu His Ser Leu Cys Pro
                965                 970                 975

Val Ser Thr Pro Thr Gln Val Gln Ala Cys Asn Ser His Ala Cys Pro
                980                 985                 990

Pro Gln Trp Ser Leu Gly Pro Trp Ser Gln Cys Ser Lys Thr Cys Gly
                995                 1000                1005

Arg Gly Val Arg Lys Arg Glu Leu Leu Cys Lys Gly Ser Ala Ala Glu
    1010                1015                1020

Thr Leu Pro Glu Ser Gln Cys Thr Ser Leu Pro Arg Pro Glu Leu Gln
1025                1030                1035                1040

Glu Gly Cys Val Leu Gly Arg Cys Pro Lys Asn Ser Arg Leu Gln Trp
            1045                1050                1055

Val Ala Ser Ser Trp Ser Glu Cys Ser Ala Thr Cys Gly Leu Gly Val
            1060                1065                1070

Arg Lys Arg Glu Met Lys Cys Ser Glu Lys Gly Phe Gln Gly Lys Leu
    1075                1080                1085

Ile Thr Phe Pro Glu Arg Arg Cys Arg Asn Ile Lys Lys Pro Asn Leu
    1090                1095                1100

Asp Leu Glu Glu Thr Cys Asn Arg Arg Ala Cys Pro Ala His Pro Val
1105                1110                1115                1120

Tyr Asn Met Val Ala Gly Trp Tyr Ser Leu Pro Trp Gln Gln Cys Thr
            1125                1130                1135

Val Thr Cys Gly Gly Gly Val Gln Thr Arg Ser Val His Cys Val Gln
        1140                1145                1150

Gln Gly Arg Pro Ser Ser Ser Cys Leu Leu His Gln Lys Pro Pro Val
    1155                1160                1165

Leu Arg Ala Cys Asn Thr Asn Phe Cys Pro Ala Pro Glu Lys Arg Glu
1170                1175                1180
```

Asp Pro Ser Cys Val Asp Phe Phe Asn Trp Cys His Leu Val Pro Gln
1185                1190                1195                1200

His Gly Val Cys Asn His Lys Phe Tyr Gly Lys Gln Cys Cys Lys Ser
            1205                1210                1215

Cys Thr Arg Lys Ile
        1220

<210> SEQ ID NO 3
<211> LENGTH: 3219
<212> TYPE: DNA
<213> ORGANISM: Homo sapiens

<400> SEQUENCE: 3

| | | | | |
|---|---|---|---|---|
| atgtcacctt | ttctcttgca | ggcgctccag | ctgtgctgcc | tctgctgtgc gtcggtcgcc | 60 |
| gcggccttag | ccagtgacag | cagcagcggc | gccagcggat | aaatgatga ttacgtcttt | 120 |
| gtcacgccag | tagaagtaga | ctcagccggg | tcatatattt | cacacgacat tttgcacaac | 180 |
| ggcaggaaaa | agcgatcggc | gcagaatgcc | agaagctccc | tgcactaccg atttcagca | 240 |
| tttggacagt | aactgcactt | agaacttaag | ccctcggcga | ttttgagcag tcactttatt | 300 |
| gtccaggtac | ttgaaaaga | tggtgcttca | gagactcaga | acccgaggt gcagcaatgc | 360 |
| ttctatcagg | gatttatcag | aaatgacagc | tcctcctctg | tcgctgtgtc tacgtgtgct | 420 |
| ggcttgtcag | gtttaataag | gacacgaaaa | atgaattcc | tcatctcgcc attacctcag | 480 |
| cttctggccc | aggaacacaa | ccacagctcc | cctgcgggtc | accatcctca cgtactgtac | 540 |
| aaaaggacag | cagaggagaa | gatccagcgg | taccgtggct | accccggctc tggccggaat | 600 |
| tatcctggtt | actccccaag | tcacattccc | catgcatctc | agagtcgaga cagagtat | 660 |
| caccatcgaa | ggttgcaaaa | gcagcatttt | tgtggacgac | gcaagaaata tgctcccaag | 720 |
| cctcccacag | aggacaccta | tctaaggttt | gatgaatatg | ggagctctgg gcgacccaga | 780 |
| agatcagctg | gaaaatcaca | aaagggcctc | aatgtggaaa | ccctcgtggt ggcagacaag | 840 |
| aaaatggtgg | aaaagcatgg | caagggaaat | gtcaccacat | acattctcac agtaatgaac | 900 |
| atggtttctg | gcctatttaa | agatgggact | attggaagtg | acataaacgt ggttgtggtg | 960 |
| agcctaattc | ttctggaaca | agaacctgga | ggattattga | tcaaccatca tgcagaccag | 1020 |
| tctctgaata | gttttgtca | atggcagtct | gccctcattg | gaaagaatgg caagagacat | 1080 |
| gatcatgcca | tcttactaac | aggatttgat | atttgttctt | ggaagaatga accatgtgac | 1140 |
| actctagggt | ttgcccccat | cagtggaatg | tgctctaagt | accgaagttg taccatcaat | 1200 |
| gaggacacag | gacttggcct | tgccttcacc | atcgctcatg | agtcagggca caactttggt | 1260 |
| atgattcacg | acggagaagg | gaatccctgc | agaaaggctg | aaggcaatat catgtctccc | 1320 |
| acactgaccg | gaaacaatgg | agtgtttca | tggtcttctt | gcagccgcca gtatctcaag | 1380 |
| aaattcctca | gcacacctca | ggcggggtgt | ctagtggatg | agcccaagca agcaggacga | 1440 |
| tataaatatc | cggacaaact | accaggacag | atttatgatg | ctgacacaca gtgtaaatgg | 1500 |
| caatttggag | caaaagccaa | gttatgcagc | cttggttttg | tgaaggatat ttgcaaatca | 1560 |
| ctttggtgcc | accgagtagg | ccacaggtgt | gagaccaagt | ttatgcccgc agcagaaggg | 1620 |
| accgtttgtg | gcttgagtat | gtggtgtcgg | caaggccagt | gcgtaaagtt tggggagctc | 1680 |
| gggccccggc | ccatccacgg | ccagtggtcc | gcctggtcga | agtggtcaga atgttcccgg | 1740 |
| acatgtggtg | gaggagtcaa | gttccaggag | agacactgca | ataaccccaa gcctcagtat | 1800 |
| ggtggcatat | tctgtccagg | ttctagccgt | atttatcagc | tgtgcaatat taacccttgc | 1860 |

-continued

```
aatgaaaata gcttggattt tcgggcccaa cagtgtgcag aatataacag caaacctttc    1920
cgtggatggt tctaccagtg gaaaccctat acaaaagtgg aagaggaaga tcgatgcaaa    1980
ctgtactgca aggctgagaa ctttgaattt tttttttgcaa tgtccggcaa agtgaaagat    2040
ggaactccct gctccccaaa cagaaatgat gtttgtattg acggggtttg tgaactagtg    2100
ggatgtgatc atgaactagg ctctaaagca gtttcagatg cttgtggcgt ttgcaaaggt    2160
gataattcaa cttgcaagtt ttataaaggc ctgtacctca accagcataa agcaaatgaa    2220
tattatccgg tggtcatcat tccagctggc gcccgaagca tcgaaatcca ggagctgcag    2280
gtttcctcca gttacctcgc agttcgaagc ctcagtcaaa agtattacct caccgggggc    2340
tggagcatcg actggcctgg ggagttcccc ttcgctggga ccacgtttga ataccagcgc    2400
tctttcaacc gcccggaacg tctgtacgcg ccagggccca caaatgagac gctggtcttt    2460
gaaattctga tgcaaggcaa aaatccaggg atagcttgga agtatgcact tcccaaggtc    2520
atgaatggaa ctccaccagc cacaaaaaga cctgcctata cctggagtat cgtgcagtca    2580
gagtgctccg tctcctgtgg tggaggttac ataaatgtaa aggccatttg cttgcgagat    2640
caaaatactc aagtcaattc ctcattctgc agtgcaaaaa ccaagccagt aactgagccc    2700
aaaatctgca acgctttctc ctgcccggct tactggatgc caggtgaatg gagtacatgt    2760
agcaaggcct gtgctggagg ccagcagagc cgaaagatcc agtgtgtgca aaagaagccc    2820
ttccaaaagg aggaagcagt gttgcattct ctctgtccag tgagcacacc cactcaggtc    2880
caagcctgca acagccatgc ctgtcctcca caatggagcc ttggaccctg gtctcagtgt    2940
tccaagacct gtggacgagg ggtgaggaag cgtgaactcc tctgcaaggg ctctgccgca    3000
gaaaccctcc ccgagagcca gtgtaccagt ctcccccagac ctgagctgca ggagggctgt    3060
gtgcttggac gatgccccaa gaacagccgg ctacagtggg tcgcttcttc gtggagcgag    3120
tgttctgcaa cctgtggttt gggtgtgagg aagaggaga tgaagtgcag cgagaagggc    3180
ttccagggaa agctgataac tttcccagag cgaagatgc                         3219
```

<210> SEQ ID NO 4
<211> LENGTH: 1071
<212> TYPE: PRT
<213> ORGANISM: Homo sapiens

<400> SEQUENCE: 4

```
Met Ser Pro Phe Leu Leu Gln Ala Leu Gln Leu Cys Cys Leu Cys Cys
  1               5                  10                  15

Ala Ser Val Ala Ala Ala Leu Ala Ser Asp Ser Ser Gly Ala Ser
             20                  25                  30

Gly Leu Asn Asp Asp Tyr Val Phe Val Thr Pro Val Glu Val Asp Ser
         35                  40                  45

Ala Gly Ser Tyr Ile Ser His Asp Ile Leu His Asn Gly Arg Lys Lys
     50                  55                  60

Arg Ser Ala Gln Asn Ala Arg Ser Ser Leu His Tyr Arg Phe Ser Ala
 65                  70                  75                  80

Phe Gly Gln Glu Leu His Leu Glu Leu Lys Pro Ser Ala Ile Leu Ser
                 85                  90                  95

Ser His Phe Ile Val Gln Val Leu Gly Lys Asp Gly Ala Ser Glu Thr
            100                 105                 110

Gln Lys Pro Glu Val Gln Gln Cys Phe Tyr Gln Gly Phe Ile Arg Asn
        115                 120                 125
```

```
Asp Ser Ser Ser Val Ala Val Ser Thr Cys Ala Gly Leu Ser Gly
130                 135                 140

Leu Ile Arg Thr Arg Lys Asn Glu Phe Leu Ile Ser Pro Leu Pro Gln
145                 150                 155                 160

Leu Leu Ala Gln Glu His Asn His Ser Ser Pro Ala Gly His His Pro
                165                 170                 175

His Val Leu Tyr Lys Arg Thr Ala Glu Glu Lys Ile Gln Arg Tyr Arg
            180                 185                 190

Gly Tyr Pro Gly Ser Gly Arg Asn Tyr Pro Gly Tyr Ser Pro Ser His
            195                 200                 205

Ile Pro His Ala Ser Gln Ser Arg Glu Thr Glu Tyr His His Arg Arg
210                 215                 220

Leu Gln Lys Gln His Phe Cys Gly Arg Arg Lys Lys Tyr Ala Pro Lys
225                 230                 235                 240

Pro Pro Thr Glu Asp Thr Tyr Leu Arg Phe Asp Glu Tyr Gly Ser Ser
            245                 250                 255

Gly Arg Pro Arg Arg Ser Ala Gly Lys Ser Gln Lys Gly Leu Asn Val
            260                 265                 270

Glu Thr Leu Val Val Ala Asp Lys Lys Met Val Glu Lys His Gly Lys
            275                 280                 285

Gly Asn Val Thr Thr Tyr Ile Leu Thr Val Met Asn Met Val Ser Gly
            290                 295                 300

Leu Phe Lys Asp Gly Thr Ile Gly Ser Asp Ile Asn Val Val Val Val
305                 310                 315                 320

Ser Leu Ile Leu Leu Glu Gln Glu Pro Gly Gly Leu Leu Ile Asn His
                325                 330                 335

His Ala Asp Gln Ser Leu Asn Ser Phe Cys Gln Trp Gln Ser Ala Leu
            340                 345                 350

Ile Gly Lys Asn Gly Lys Arg His Asp His Ala Ile Leu Leu Thr Gly
            355                 360                 365

Phe Asp Ile Cys Ser Trp Lys Asn Glu Pro Cys Asp Thr Leu Gly Phe
370                 375                 380

Ala Pro Ile Ser Gly Met Cys Ser Lys Tyr Arg Ser Cys Thr Ile Asn
385                 390                 395                 400

Glu Asp Thr Gly Leu Gly Leu Ala Phe Thr Ile Ala His Glu Ser Gly
            405                 410                 415

His Asn Phe Gly Met Ile His Asp Gly Glu Gly Asn Pro Cys Arg Lys
            420                 425                 430

Ala Glu Gly Asn Ile Met Ser Pro Thr Leu Thr Gly Asn Asn Gly Val
            435                 440                 445

Phe Ser Trp Ser Cys Ser Arg Gln Tyr Leu Lys Lys Phe Leu Ser
450                 455                 460

Thr Pro Gln Ala Gly Cys Leu Val Asp Glu Pro Lys Gln Ala Gly Gln
465                 470                 475                 480

Tyr Lys Tyr Pro Asp Lys Leu Pro Gly Gln Ile Tyr Asp Ala Asp Thr
            485                 490                 495

Gln Cys Lys Trp Gln Phe Gly Ala Lys Ala Lys Leu Cys Ser Leu Gly
            500                 505                 510

Phe Val Lys Asp Ile Cys Lys Ser Leu Trp Cys His Arg Val Gly His
            515                 520                 525

Arg Cys Glu Thr Lys Phe Met Pro Ala Ala Glu Gly Thr Val Cys Gly
530                 535                 540

Leu Ser Met Trp Cys Arg Gln Gly Gln Cys Val Lys Phe Gly Leu Gly
```

-continued

```
      545                 550                 555                 560
Pro Arg Pro Ile His Gly Gln Trp Ser Ala Trp Ser Lys Trp Ser Glu
                565                 570                 575
Cys Ser Arg Thr Cys Gly Gly Val Lys Phe Gln Glu Arg His Cys
                580                 585                 590
Asn Asn Pro Lys Pro Gln Tyr Gly Gly Ile Phe Cys Pro Gly Ser Ser
                595                 600                 605
Arg Ile Tyr Gln Leu Cys Asn Ile Asn Pro Cys Asn Glu Asn Ser Leu
                610                 615                 620
Asp Phe Arg Ala Gln Gln Cys Ala Glu Tyr Asn Ser Lys Pro Phe Arg
625                 630                 635                 640
Gly Trp Phe Tyr Gln Trp Lys Pro Tyr Thr Lys Val Glu Glu Asp
                645                 650                 655
Arg Cys Lys Leu Tyr Cys Lys Ala Glu Asn Phe Glu Phe Phe Ala
                660                 665                 670
Met Ser Gly Lys Val Lys Asp Gly Thr Pro Cys Ser Pro Asn Arg Asn
                675                 680                 685
Asp Val Cys Ile Asp Gly Val Cys Glu Leu Val Gly Cys Asp His Glu
                690                 695                 700
Leu Gly Ser Lys Ala Val Ser Asp Ala Cys Gly Val Cys Gly Asp Asn
705                 710                 715                 720
Ser Thr Cys Lys Phe Tyr Lys Gly Leu Tyr Leu Asn Gln His Lys Ala
                725                 730                 735
Asn Glu Tyr Tyr Pro Val Val Ile Ile Pro Ala Gly Ala Arg Ser Ile
                740                 745                 750
Glu Ile Gln Glu Leu Gln Val Ser Ser Tyr Leu Ala Val Arg Ser
                755                 760                 765
Leu Ser Gln Lys Tyr Tyr Leu Thr Gly Gly Trp Ser Ile Asp Trp Pro
770                 775                 780
Gly Glu Phe Pro Phe Ala Gly Thr Thr Phe Glu Tyr Gln Arg Ser Phe
785                 790                 795                 800
Asn Arg Pro Glu Arg Leu Tyr Ala Pro Gly Pro Thr Asn Glu Thr Leu
                805                 810                 815
Val Phe Glu Ile Leu Met Gln Gly Lys Asn Pro Gly Ile Ala Trp Lys
                820                 825                 830
Tyr Ala Leu Pro Lys Val Met Asn Gly Thr Pro Pro Ala Thr Lys Arg
                835                 840                 845
Pro Ala Tyr Thr Trp Ser Ile Val Gln Ser Glu Cys Ser Val Ser Cys
                850                 855                 860
Gly Gly Gly Tyr Ile Asn Val Lys Ala Ile Cys Leu Arg Asp Gln Asn
865                 870                 875                 880
Thr Gln Val Asn Ser Ser Phe Cys Ser Ala Lys Thr Lys Pro Val Thr
                885                 890                 895
Glu Pro Lys Ile Cys Asn Ala Phe Ser Cys Pro Ala Tyr Trp Met Pro
                900                 905                 910
Gly Glu Trp Ser Thr Cys Ser Lys Ala Cys Ala Gly Gly Gln Gln Ser
                915                 920                 925
Arg Lys Ile Gln Cys Val Gln Lys Pro Phe Gln Lys Glu Glu Ala
                930                 935                 940
Val Leu His Ser Leu Cys Pro Val Ser Thr Pro Thr Gln Val Gln Ala
945                 950                 955                 960
Cys Asn Ser His Ala Cys Pro Pro Gln Trp Ser Leu Gly Pro Trp Ser
                965                 970                 975
```

-continued

Gln Cys Ser Lys Thr Cys Gly Arg Gly Val Arg Lys Arg Glu Leu Leu
            980                 985                 990

Cys Lys Gly Ser Ala Ala Glu Thr Leu Pro Glu Ser Gln Cys Thr Ser
            995                 1000                1005

Leu Pro Arg Pro Glu Leu Gln Glu Gly Cys Val Leu Gly Arg Cys Pro
    1010                1015                1020

Lys Asn Ser Arg Leu Gln Trp Val Ala Ser Ser Trp Ser Glu Cys Ser
1025                1030                1035                1040

Ala Thr Cys Gly Leu Gly Val Arg Lys Arg Glu Met Lys Cys Ser Glu
            1045                1050                1055

Lys Gly Phe Gln Gly Lys Leu Ile Thr Phe Pro Glu Arg Arg Cys
            1060                1065                1070

<210> SEQ ID NO 5
<211> LENGTH: 3954
<212> TYPE: DNA
<213> ORGANISM: Homo sapiens

<400> SEQUENCE: 5

| | |
|---|---|
| atgtcacctt ttctcttgca ggcgctccag ctgtgctgcc tctgctgtgc gtcggtcgcc | 60 |
| gcggccttag ccagtgacag cagcagcggc gccagcggat taaatgatgg ttcgtatttg | 120 |
| ccccccatcc ccaagaaggg cctttcgcag cactttgacc cttccttccc ccaaagagag | 180 |
| aaaagatgga aaagcgcacc ccctaacctg gcagattacg tctttgtcac gccagtagaa | 240 |
| gtagactcag ccgggtcata tatttcacac gacattttgc acaacggcag gaaaaagcga | 300 |
| tcggcgcaga atgccagaag ctccctgcac taccgatttt cagcatttgg acaggaactg | 360 |
| cacttagaac ttaagccctc ggcgattttg agcagtcact ttattgtcca ggtacttgga | 420 |
| aaagatggtg cttcagagac tcagaaaccc gaggtgcagc aatgcttcta tcagggattt | 480 |
| atcagaaatg acagctcctc ctctgtcgct gtgtctacgt gtgctggctt gatgatcccc | 540 |
| aaggaaatta acttgatgga tgccattcgc tttgtaatgt cccgggagac caggcattct | 600 |
| ataaatctaa caagcttcat gcgtctacat ggctttgaaa tgggaaaact gtatttcaat | 660 |
| gcgaaattgc attcagcagc actgtttaat aaaggaaaga aaagcttcac ctatggggga | 720 |
| ctcagagtca ttgtcctcaa ggtgtctgaa caggaccttc agtggaaacg agactgcctg | 780 |
| aacctctctg ggagagttgt ttttgctttg tggaatgcat cacaccatct catggcttta | 840 |
| catatgaatt cctcatctcg ccattacctc agcttctggc caggaacaca aactacagct | 900 |
| cccctgcggg tcaccatcct cacgtactgt acaaaaggac agcagaggag aagatccagc | 960 |
| ggtaccgtgg ctaccccggc tctggccgga attatcctgg ttactcccca agtcacattc | 1020 |
| cccatgcatc tcagagtcga gagacagagt atcaccatcg aaggttgcaa agcagcatt | 1080 |
| tttgtggacg acgcaagaaa tgtatttttct ctctcaactg tcttatccag atattctcta | 1140 |
| atatcccttc caaatgctct tctgttcatc gtagatgctc ccaagcctcc cacagaggac | 1200 |
| acctatctaa ggtttgatga atatgggagc tctgggcgac ccagaagatc agctggaaaa | 1260 |
| tcacaaaagg gcctcaatgt ggaaaccctc gtggtggcag acaagaaaat ggtggaaaag | 1320 |
| catggcaagg gaaatgtcac cacatacatt ctcacagtaa tgaacatggt ttctggccta | 1380 |
| tttaaagatg ggactattgg aagtgacata aacgtggttg tggtgagcct aattcttctg | 1440 |
| gaacaagaac ctgggaggat tattgatcaa catcatgcag accagtctct gaatagtttt | 1500 |
| tgtcaatggc agtctgccct cattggaaag aatggcaaga gacatgatca tgccatctta | 1560 |

```
ctaacaggat tgatatttg ttcttggaag aatgaaccat gtgacactct agggtttgcc    1620
cccatcagtg gaatgtgctc taagtaccga agttgtacca tcaatgagga cacaggactt   1680
ggccttgcct tcaccatcgc tcatgagtca gggcacaact ttggtatgat tcacgacgga   1740
gaagggaatc cctgcagaaa ggctgaaggc aatatcatgt ctcccacact gaccggaaac   1800
aatggagtgt tttcatggtc ttcctgcagc cgccagtatc tcaagaaatt cctcagcaca   1860
cctcaggcgg ggtgtctagt ggatgagccc aagcaagcag gacagtataa atatccggac   1920
aaactaccag gacagattta tgatgctgac acacagtgta aatggcaatt tggagcaaaa   1980
gccaagttat gcagccttgg ttttgtgaag tggtgtcggc aaggccagtg cgtaaagttt   2040
ggggagctcg ggccccggcc catccacggc cagtggtccg cctggtcgaa gtggtcagaa   2100
tgttcccgga catgtggtgg aggagtcaag ttccaggaga gacactgcaa taaccccaat   2160
aacaatcaac cagagtttta ctgtttgcat ataaagtcca tgtgcaccga gggaaggtat   2220
ggtgggcaga accaaaaaca cagcagagga gtcattctct acgggactgt gatgatccag   2280
cctcagtatg gtggcttatt ctgtccaggt tctagccgta tttatcagct gtgcaatatt   2340
aacccttgca atgaaaatag cttggatttt cgggctcaac agtgtgcaga atataacagc   2400 aaaccttttcc gtggatggtt ctaccagtgg aaaccctata caaaagtgga agaggaagat   2460
cgatgcaaac tgtactgcaa ggctgagaac tttgaatttt tttttgcaat gtccggcaaa   2520
gtgaaagatg gaactccctg ctccccaaac aaaaatgatg tttgtattga cggggtttgt   2580
gaactagtgg gatgtgatca tgaactaggc tctaaagcag tttcagatgc ttgtggcgtt   2640
tgcaaaggtg ataattcaac ttgcaagttt tataaaggcc tgtacctcaa ccagcataaa   2700
gcaaatgaat attatccggt ggtcctcatt ccagctggcg cccgaagcat cgaaatccag   2760
gagctgcagg tttcctccag ttacctcgca gttcgaagcc tcagtcaaaa gtattacctc   2820
accgggggct ggagcatcga ctggcctggg gagttcccct tcgctgggac cacgtttgaa   2880
taccagcgct ctttcaaccg cccggaacgt ctgtacgcgc cagggcccac aaatgagacg   2940
ctggtctttg aagtaagccc cttctgtgta ttcagttctc agtgcttctt gctacattta   3000
tatcgtatgg atatcccctc agggtaagg tcagcaaagg ttctctcact agaggaatgg   3060
attaaatctg agacaaccct tgcaaggaag aacaacagc aaccatctac tggctggatg   3120
ccaggtgaat ggagtacatg cagcaagtcc tgtgctggag gccagcagag ccgaaagatc   3180
cagtgtgtgc aaaagaagcc cttccaaaag gaggaagcag tgttgcattc tctctgtcca   3240
gtaagcacac ccactcaggt ccaagcctgc aacagccatg cctgccctcc acaatggagc   3300 cttggacccct ggtctcagtg ttccaagacc tgtggacgag gggtgaggaa gcgtgaactc   3360
ctctgcaagg gctctgccgc agaaaccctc cccgagagcc agtgtaccag tctccccaga   3420
cctgagctgc aggagggctg tgtgcttgga cgatgcccca agaacagccg gctacagtgg   3480
gtcgcttctt cgtggagcga gtgttctgca acctgtggtt tgggtgtgag gaagagggag   3540
atgaagtgca gcgagaaggg cttccaggga aagctgataa ctttcccaga gcgaagatgc   3600
cgtaatatta agaaaccaaa tctggacttg gaagagacct gcaaccgacg ggcttgccca   3660
gcccatccag tgtacaacat ggtagctgga tggtattcat tgccgtggca gcagtgcaca   3720
gtcacctgtg ggggagggt ccagacccgg tcagtccact gtgttcagca aggccggcct   3780
tcctcaagtt gtctgctcca tcagaaacct ccggtgctac gagcctgtaa tacaaacttc   3840
tgtccagctc ctgaaaagag agatcttaat tccttgaata cctctatggt ctccactggt   3900
gctgagggtc aacacctaag acggttttcg tcagtcaccc ctggatctgg gtga         3954
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic zinc binding signature peptide sequence

<400> SEQUENCE: 6

Thr Ala Ala His Glu Leu Gly His Val Lys Phe
 1               5                  10

<210> SEQ ID NO 7
<211> LENGTH: 1986
<212> TYPE: DNA
<213> ORGANISM: Homo sapiens

<400> SEQUENCE: 7

| | | | | | |
|---|---|---|---|---|---|
| atggagtgcg | ccctcctgct | cgcgtgtgcc | ttcccggctg | cgggttcggg | cccgccgagg | 60 |
| ggcctggcgg | gactggggcg | cgtggccaag | gcgctccagc | tgtgctgcct | ctgctgtgcg | 120 |
| tcggtcgccg | cggccttagc | cagtgacagc | agcagcggcg | ccagcggatt | aaatgatgat | 180 |
| tacgtctttg | tcacgccagt | agaagtagac | tcagccgggt | catatatttc | acacgacatt | 240 |
| ttgcacaacg | gcaggaaaaa | gcgatcggcg | cagaatgcca | aagctccct | gcactaccga | 300 |
| ttttcagcat | ttggacagga | actgcactta | gaacttaagc | cctcggcgat | tttgagcagt | 360 |
| cactttattg | tccaggtact | tggaaaagat | ggtgcttcag | agactcagaa | acccgaggtg | 420 |
| cagcaatgct | tctatcaggg | atttatcaga | aatgacagct | cctcctctgt | cgctgtgtct | 480 |
| acgtgtgctg | gcttgtcagg | tttaataagg | acacgaaaaa | atgaattcct | catctcgcca | 540 |
| ttacctcagc | ttctggccca | ggaacacaac | cacagctccc | ctgcgggtca | ccatcctcac | 600 |
| gtactgtaca | aaaggacagc | agaggagaag | atccagcgt | accgtggcta | ccccggctct | 660 |
| ggccggaatt | atcctggtta | ctccccaagt | cacattcccc | atgcatctca | gagtcgagag | 720 |
| acagagtatc | accatcgaag | gttgcaaaag | cagcattttt | gtggacgacg | caagaaatat | 780 |
| gctcccaagc | ctcccacaga | ggacacctat | ctaaggtttg | atgaatatgg | gagctctggg | 840 |
| cgacccagaa | gatcagctgg | aaaatcacaa | aagggcctca | atgtggaaac | cctcgtggtg | 900 |
| gcagacaaga | aaatggtgga | aaagcatggc | aagggaaatg | tcaccacata | cattctcaca | 960 |
| gtaatgaaca | tggtttctgg | cctatttaaa | gatgggacta | ttggaagtga | cataaacgtg | 1020 |
| gttgtggtga | gcctaattct | tctggaacaa | gaacctggag | gattattgat | caaccatcat | 1080 |
| gcagaccagt | ctctgaatag | tttttgtcaa | tggcagtctg | ccctcattgg | aaagaatggc | 1140 |
| aagagacatg | atcatgccat | cttactaaca | ggatttgata | tttgttcttg | gaagaatgaa | 1200 |
| ccatgtgaca | ctctaggggtt | tgcccccatc | agtggaatgt | gctctaagta | ccgaagttgt | 1260 |
| accatcaatg | aggacacagg | acttggcctt | gccttcacca | tcgctcatga | gtcagggcac | 1320 |
| aactttggta | tgattcacga | cggagaaggg | aatccctgca | gaaaggctga | aggcaatatc | 1380 |
| atgtctccca | cactgaccgg | aaacaatgga | gtgttttcat | ggtcttcttg | cagccgccag | 1440 |
| tatctcaaga | aattcctcag | cacacctcag | gcggggtgtc | tagtggatga | gcccaagcaa | 1500 |
| gcaggacagt | ataaatatcc | ggacaaacta | ccaggacaga | tttatgatgc | tgacacacag | 1560 |
| tgtaaatggc | aatttggagc | aaaagccaag | ttatgcagcc | ttggttttgt | gaaggatatt | 1620 |
| tgcaaatcac | tttggtgcca | ccgagtaggc | cacaggtgtg | agaccaagtt | tatgcccgca | 1680 |

-continued

```
gcagaaggga ccgtttgtgg cttgagtatg tggtgtcggc aaggccagtg cgtaaagttt    1740
ggggagctcg ggccccggcc catccacggc cagtggtccg cctggtcgaa gtggtcagaa    1800
tgttcccgga catgtggtgg aggagtcaag ttccaggaga gacactgcaa taacccaag     1860 cctcagtatg gtggcatatt ctgtccaggt tctagccgta tttatcagct gtgcaatatt    1920 aaccttgca atgaaatag cttggatttt ggaagcgctt ggagccaccc gcagttcgaa      1980
aaataa                                                               1986
```

<210> SEQ ID NO 8
<211> LENGTH: 661
<212> TYPE: PRT
<213> ORGANISM: Homo sapiens

<400> SEQUENCE: 8

```
Met Glu Cys Ala Leu Leu Ala Cys Ala Phe Pro Ala Ala Gly Ser
  1               5                  10                  15

Gly Pro Pro Arg Gly Leu Ala Gly Leu Gly Arg Val Ala Lys Ala Leu
                 20                  25                  30

Gln Leu Cys Cys Leu Cys Cys Ala Ser Val Ala Ala Leu Ala Ser
             35                  40                  45

Asp Ser Ser Ser Gly Ala Ser Gly Leu Asn Asp Asp Tyr Val Phe Val
         50                  55                  60

Thr Pro Val Glu Val Asp Ser Ala Gly Ser Tyr Ile Ser His Asp Ile
 65                  70                  75                  80

Leu His Asn Gly Arg Lys Lys Arg Ser Ala Gln Asn Ala Arg Ser Ser
                 85                  90                  95

Leu His Tyr Arg Phe Ser Ala Phe Gly Gln Glu Leu His Leu Glu Leu
            100                 105                 110

Lys Pro Ser Ala Ile Leu Ser Ser His Phe Ile Val Gln Val Leu Gly
        115                 120                 125

Lys Asp Gly Ala Ser Glu Thr Gln Lys Pro Glu Val Gln Gln Cys Phe
    130                 135                 140

Tyr Gln Gly Phe Ile Arg Asn Asp Ser Ser Ser Val Ala Val Ser
145                 150                 155                 160

Thr Cys Ala Gly Leu Ser Gly Leu Ile Arg Thr Arg Lys Asn Glu Phe
                165                 170                 175

Leu Ile Ser Pro Leu Pro Gln Leu Leu Ala Gln Glu His Asn His Ser
            180                 185                 190

Ser Pro Ala Gly His His Pro His Val Leu Tyr Lys Arg Thr Ala Glu
        195                 200                 205

Glu Lys Ile Gln Arg Tyr Arg Gly Tyr Pro Gly Ser Gly Arg Asn Tyr
    210                 215                 220

Pro Gly Tyr Ser Pro Ser His Ile Pro His Ala Ser Gln Ser Arg Glu
225                 230                 235                 240

Thr Glu Tyr His His Arg Arg Leu Gln Lys Gln His Phe Cys Gly Arg
                245                 250                 255

Arg Lys Lys Tyr Ala Pro Lys Pro Pro Thr Glu Asp Thr Tyr Leu Arg
            260                 265                 270

Phe Asp Glu Tyr Gly Ser Ser Gly Arg Pro Arg Arg Ser Ala Gly Lys
        275                 280                 285

Ser Gln Lys Gly Leu Asn Val Glu Thr Leu Val Val Ala Asp Lys Lys
    290                 295                 300

Met Val Glu Lys His Gly Lys Gly Asn Val Thr Thr Tyr Ile Leu Thr
305                 310                 315                 320
```

```
Val Met Asn Met Val Ser Gly Leu Phe Lys Asp Gly Thr Ile Gly Ser
            325                 330                 335

Asp Ile Asn Val Val Val Ser Leu Ile Leu Glu Gln Glu Pro
            340                 345             350

Gly Gly Leu Leu Ile Asn His His Ala Asp Gln Ser Leu Asn Ser Phe
            355                 360                 365

Cys Gln Trp Gln Ser Ala Leu Ile Gly Lys Asn Gly Lys Arg His Asp
370                 375                 380

His Ala Ile Leu Leu Thr Gly Phe Asp Ile Cys Ser Trp Lys Asn Glu
385                 390                 395                 400

Pro Cys Asp Thr Leu Gly Phe Ala Pro Ile Ser Gly Met Cys Ser Lys
            405                 410                 415

Tyr Arg Ser Cys Thr Ile Asn Glu Asp Thr Gly Leu Gly Leu Ala Phe
            420                 425                 430

Thr Ile Ala His Glu Ser Gly His Asn Phe Gly Met Ile His Asp Gly
            435                 440                 445

Glu Gly Asn Pro Cys Arg Lys Ala Glu Gly Asn Ile Met Ser Pro Thr
450                 455                 460

Leu Thr Gly Asn Asn Gly Val Phe Ser Trp Ser Ser Cys Ser Arg Gln
465                 470                 475                 480

Tyr Leu Lys Lys Phe Leu Ser Thr Pro Gln Ala Gly Cys Leu Val Asp
            485                 490                 495

Glu Pro Lys Gln Ala Gly Gln Tyr Lys Tyr Pro Asp Lys Leu Pro Gly
            500                 505                 510

Gln Ile Tyr Asp Ala Asp Thr Gln Cys Lys Trp Gln Phe Gly Ala Lys
            515                 520                 525

Ala Lys Leu Cys Ser Leu Gly Phe Val Lys Asp Ile Cys Lys Ser Leu
            530                 535                 540

Trp Cys His Arg Val Gly His Arg Cys Glu Thr Lys Phe Met Pro Ala
545                 550                 555                 560

Ala Glu Gly Thr Val Cys Gly Leu Ser Met Trp Cys Arg Gln Gly Gln
            565                 570                 575

Cys Val Lys Phe Gly Glu Leu Gly Pro Arg Pro Ile His Gly Gln Trp
            580                 585                 590

Ser Ala Trp Ser Lys Trp Ser Glu Cys Ser Arg Thr Cys Gly Gly Gly
            595                 600                 605

Val Lys Phe Gln Glu Arg His Cys Asn Asn Pro Lys Pro Gln Tyr Gly
            610                 615                 620

Gly Ile Phe Cys Pro Gly Ser Ser Arg Ile Tyr Gln Leu Cys Asn Ile
625                 630                 635                 640

Asn Pro Cys Asn Glu Asn Ser Leu Asp Phe Gly Ser Ala Trp Ser His
            645                 650                 655

Pro Gln Phe Glu Lys
            660

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 9
taaatcgaat tcccaccatg tcaccttttc tcttgcaggc g                    41
```

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
cagcttcacc agtcttacaa gggcc                                         25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 11
ctgcctctgc tgtgcgtcgg tcgc                                          24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
ctattgaaag ggtctcgctt ctacg                                         25

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      pre-pro signal peptide sequence

<400> SEQUENCE: 13

Leu Leu Gln Ala Leu Gln Leu Cys Cys Leu Cys Cys Ala
 1               5                  10

<210> SEQ ID NO 14
<211> LENGTH: 50
<212> TYPE: PRT
<213> ORGANISM: Artificial Sequence
<220> FEATURE:
<223> OTHER INFORMATION: Description of Artificial Sequence: Synthetic
      pre-pro signal peptide sequence

<400> SEQUENCE: 14

Ser Val Ala Ala Ala Leu Ala Ser Asp Ser Ser Gly Ala Ser Gly
 1               5                  10                  15

Leu Asn Asp Asp Tyr Val Phe Val Thr Pro Val Glu Val Asp Ser Ala
                20                  25                  30

Gly Ser Tyr Ile Ser His Asp Ile Leu His Asn Gly Arg Lys Lys Arg
            35                  40                  45

Ser Ala
    50

<210> SEQ ID NO 15
<211> LENGTH: 7
<212> TYPE: PRT
<213> ORGANISM: Artificial Sequence
<220> FEATURE:

-continued

<223> OTHER INFORMATION: Description of Artificial Sequence: Synthetic
      CD36-binding motif

<400> SEQUENCE: 15

Cys Ser Arg Thr Cys Gly Gly
  1               5

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16
tggtatgatt cacgacggag aaggg 25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
cgggtcacca tcctcacgta ctgta 25

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
aaccctcgtg gtggcagaca ag 22

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
tcattccagc tggcgcccga agcat 25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 20
gataactttc ccagagcgaa gatgc 25

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
aattcccacc atggagtgcg ccctcctgct cgcgtgtgcc t                    41
```

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
cccaccatgg agtgcgccct cctgctcgcg tgtgccttcc cggctgcg             48
```

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
tcccggctgc gggttcgggc cgccgaggg gcctggcggg actggggcgc gtggccaag   59
```

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
ggttcgggcc cgccgagggg cctggcggga ctggggcgcg tggccaaggc gctccagct  59
```

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
gcgctccagc tgtgctgcct ctgctgtgcg tcggtcgccc c                    41
```

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
gtgctgcctc tgctgtgcgt cggtcgcc                                   28
```

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 27

```
ctcgcggttg aggacaaact cttcg                                      25
```

```
<210> SEQ ID NO 28
<211> LENGTH: 79
<212> TYPE: DNA
<213> ORGANISM: Artificial Sequence
<220> FEATURE:
<223> OTHER INFORMATION: Description of Artificial Sequence: Primer

<400> SEQUENCE: 28
cccttgcaat gaaaatagct tggattttgg aagcgcttgg agccacccgc agttcgaaaa      60
ataaggcggc cgccgcaaa                                                  79

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 29

Gly Ser Ala Trp Ser His Pro Gln Phe Glu Lys
 1               5                  10

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 30
catgggcagc tcgag                                                      15

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 31
ctgcaggcga gcctgaattc ctcgagccat catg                                 34

<210> SEQ ID NO 32
<211> LENGTH: 68
<212> TYPE: DNA
<213> ORGANISM: Artificial Sequence
<220> FEATURE:
<223> OTHER INFORMATION: Description of Artificial Sequence: Primer

<400> SEQUENCE: 32
cgaggttaaa aaacgtctag gccccccgaa ccacggggac gtggttttcc tttgaaaaac     60
acgattgc                                                              68
```